(12) United States Patent
Rogelj et al.

(10) Patent No.: US 9,834,514 B2
(45) Date of Patent: Dec. 5, 2017

(54) ANTIBIOTIC SENSITIVITY-RESTORING AND PHOTOSENSITIVE AGENTS

(71) Applicant: New Mexico Tech Research Foundation, Socorro, NM (US)

(72) Inventors: Snezna Rogelj, Socorro, NM (US); Liliya Frolova, Socorro, NM (US); Alexander Kornienko, San Marcos, TX (US); Leslie D. Edwards, Socorro, NM (US); Cody Champion, Las Cruces, NM (US); Kailee Zingler, Tomah, WI (US); Danielle Nicole Turner, Socorro, NM (US)

(73) Assignee: NEW MEXICO TECH RESEARCH FOUNDATION, Socorro, NM (US)

( * ) Notice: Subject to any disclaimer, the term of this patent is extended or adjusted under 35 U.S.C. 154(b) by 0 days.

(21) Appl. No.: 15/133,430

(22) Filed: Apr. 20, 2016

(65) Prior Publication Data

US 2016/0304453 A1 Oct. 20, 2016

Related U.S. Application Data

(60) Provisional application No. 62/306,165, filed on Mar. 10, 2016, provisional application No. 62/149,738, filed on Apr. 20, 2015.

(51) Int. Cl.
| | | |
|---|---|---|
| *A61K 31/405* | (2006.01) | |
| *C07D 209/42* | (2006.01) | |
| *A61K 38/12* | (2006.01) | |
| *A61K 31/404* | (2006.01) | |
| *A61K 31/655* | (2006.01) | |
| *A61K 41/00* | (2006.01) | |
| *C07D 209/10* | (2006.01) | |
| *C07D 209/40* | (2006.01) | |
| *C07D 209/36* | (2006.01) | |
| *C07D 209/30* | (2006.01) | |
| *A61K 31/431* | (2006.01) | |
| *A61K 31/496* | (2006.01) | |
| *A61K 31/65* | (2006.01) | |
| *A61K 31/7036* | (2006.01) | |
| *A61K 38/14* | (2006.01) | |
| *A61K 31/7048* | (2006.01) | |
| *A61K 31/43* | (2006.01) | |

(52) U.S. Cl.
CPC .......... *C07D 209/42* (2013.01); *A61K 31/404* (2013.01); *A61K 31/43* (2013.01); *A61K 31/431* (2013.01); *A61K 31/496* (2013.01); *A61K 31/65* (2013.01); *A61K 31/655* (2013.01); *A61K 31/7036* (2013.01); *A61K 31/7048* (2013.01); *A61K 38/12* (2013.01); *A61K 38/14* (2013.01); *A61K 41/0057* (2013.01); *C07D 209/10* (2013.01); *C07D 209/30* (2013.01); *C07D 209/36* (2013.01); *C07D 209/40* (2013.01)

(58) Field of Classification Search
CPC .................................................. C07D 209/42
USPC ............................................................. 514/415
See application file for complete search history.

(56) References Cited

U.S. PATENT DOCUMENTS 9,282,738 B2 * 3/2016 Weibel .................. A01N 43/52
2013/0018079 A1 1/2013 Weibel et al.
2013/0331384 A1 12/2013 Gallo et al.

FOREIGN PATENT DOCUMENTS

WO WO-9410198 A1 5/1994

OTHER PUBLICATIONS

Daly et al. Bioorganic & Medicinal Chemistry Letters 21 (2011) 4720-4723.*
Alekshun, et al. Molecular mechanisms of antibacterial multidrug resistance. Cell. Mar. 23, 2007;128(6):1037-50.
Balganesh, et al. Efflux pumps of *Mycobacterium tuberculosis* play a significant role in antituberculosis activity of potential drug candidates. Antimicrob Agents Chemother. May 2012;56(5):2643-51. doi: 10.1128/AAC.06003-11. Epub Feb. 6, 2012.
Bjorland, et al. Novel plasmid-borne gene qacJ mediates resistance to quaternary ammonium compounds in equine *Staphylococcus aureus, Staphylococcus simulans*, and *Staphylococcus intermedius*. Antimicrob Agents Chemother. Oct. 2003;47(10):3046-52.
Brown, et al. *Staphylococcal* multidrug efflux protein QacA. J Mol Microbiol Biotechnol. Apr. 2001;3(2):163-70. Review.
Cannon, et al. Efflux-mediated antifungal drug resistance. Clin Microbiol Rev. Apr. 2009;22(2):291-321, Table of Contents. doi: 10.1128/CMR.00051-08.
Dai, et al. Photodynamic therapy for localized infections—state of the art. Photodiagnosis Photodyn Ther. Sep.-Dec. 2009;6(3-4):170-88. doi: 10.1016/j.pdpdt.2009.10.008.
Daly, et al. Unprecedented C-2 arylation of indole with diazonium salts: Syntheses of 2,3-disubstituted indoles and their antimicrobial activity. Bioorg Med Chem Lett. Aug. 15, 2011;21(16):4720-3. doi: 10.1016/j.bmcl.2011.06.081. Epub Jun. 25, 2011.
Floyd, et al. LmrS is a multidrug efflux pump of the major facilitator superfamily from *Staphylococcus aureus*. Antimicrob Agents Chemother. Dec. 2010;54(12):5406-12. doi: 10.1128/AAC.00580-10. Epub Sep. 20, 2010.
Grimster, et al. Palladium-catalyzed intermolecular alkenylation of indoles by solvent-controlled regioselective C-H functionalization. Angew Chem Int Ed Engl. May 13, 2005;44(20):3125-9.
Grinius, et al. Bacterial multidrug resistance is due to a single membrane protein which functions as a drug pump. J Biol Chem. Nov. 25, 1994;269(47):29998-30004.

(Continued)

*Primary Examiner* — Nizal Chandrakumar
(74) *Attorney, Agent, or Firm* — Wilson Sonsini Goodrich & Rosati

(57) ABSTRACT

The present disclosure describes a method to treat conditions, including bacterial infections and cancer, using a photosensitive compound that, upon exposure to white light, can be activated. The photosensitive compound can also interact synergistically with antibiotics used concomitantly to kill drug-resistant bacteria. The photosensitive compounds can also be used to inhibit the proliferation of cancer cells.

41 Claims, 58 Drawing Sheets

(56) References Cited

OTHER PUBLICATIONS

Heir, et al. The qacG gene on plasmid pST94 confers resistance to quaternary ammonium compounds in staphylococci isolated from the food industry. J Appl Microbiol. Mar. 1999;86(3):378-88.
Heir, et al. The *Staphylococcus* qacH gene product: a new member of the SMR family encoding multidrug resistance. FEMS Microbiol Lett. Jun. 1, 1998;163(1):49-56.
Huang, et al. Novel chromosomally encoded multidrug efflux transporter MdeA in *Staphylococcus aureus*. Antimicrob Agents Chemother. Mar. 2004;48(3):909-17.
Kaatz, et al. Efflux-mediated fluoroquinolone resistance in *Staphylococcus aureus*. Antimicrob Agents Chemother. May 1993;37(5):1086-94.
Kaatz, et al. Multidrug resistance in *Staphylococcus aureus* due to overexpression of a novel multidrug and toxin extrusion (MATE) transport protein. Antimicrob Agents Chemother. May 2005;49(5):1857-64.
Knappe, et al. Oncocin (VDKPPYLPRPRPPRRIYNR-NH2): a novel antibacterial peptide optimized against gram-negative human pathogens. J Med Chem. Jul. 22, 2010;53(14):5240-7. doi: 10.1021/jm100378b.
Lauro, et al. Photoinactivation of bacterial strains involved in periodontal diseases sensitized by porphycene-polylysine conjugates. Photochem Photobiol Sci. Jul. 2002;1(7):468-70.
Lewis. In search of natural substrates and inhibitors of MDR pumps. J Mol Microbiol Biotechnol. Apr. 2001;3(2):247-54. Review.
Littlejohn, et al. Structure and evolution of a family of genes encoding antiseptic and disinfectant resistance in *Staphylococcus aureus*. Gene. May 15, 1991;101(1):59-66.
McAleese, et al. A novel MATE family efflux pump contributes to the reduced susceptibility of laboratory-derived *Staphylococcus aureus* mutants to tigecycline. Antimicrob Agents Chemother. May 2005;49(5):1865-71.
Narui, et al. Cloning and characterization of a novel chromosomal drug efflux gene in *Staphylococcus aureus*. Biol Pharm Bull. Dec. 2002;25(12):1533-6.
Nishino, et al. Analysis of a complete library of putative drug transporter genes in *Escherichia coli*. J Bacteriol. Oct. 2001;183(20):5803-12.
Paulsen, et al. Multidrug resistance proteins QacA and QacB from *Staphylococcus aureus*: membrane topology and identification of residues involved in substrate specificity. Proc Natl Acad Sci U S A. Apr. 16, 1996;93(8):3630-5.
Piddock. Clinically relevant chromosomally encoded multidrug resistance efflux pumps in bacteria. Clin Microbiol Rev. Apr. 2006;19(2):382-402.
Rajamohan, et al. Molecular and functional characterization of a novel efflux pump, AmvA, mediating antimicrobial and disinfectant resistance in Acinetobacter baumannii. J Antimicrob Chemother. Sep. 2010;65(9):1919-25. doi: 10.1093/jac/dkq195. Epub Jun. 23, 2010.
Rathnayake, et al. Antibiotic resistance and virulence traits in clinical and environmental Enterococcus faecalis and Enterococcus faecium isolates. Syst Appl Microbiol. Jul. 2012;35(5):326-33. doi: 10.1016/j.syapm.2012.05.004. Epub Jun. 26, 2012.
Rouch, et al. Efflux-mediated antiseptic resistance gene qacA from *Staphylococcus aureus*: common ancestry with tetracycline- and sugar-transport proteins. Mol Microbiol. Dec. 1990;4(12):2051-62.
Schwaber, et al. Carbapenem-resistant Enterobacteriaceae: a potential threat. JAMA. Dec. 24, 2008;300(24):2911-3. doi: 10.1001/jama.2008.896.
Tong, et al. *Staphylococcus aureus* infections: epidemiology, pathophysiology, clinical manifestations, and management. Clin Microbiol Rev. Jul. 2015;28(3):603-61. doi: 10.1128/CMR.00134-14. Review.

Truong-Bolduc, et al. MgrA is a multiple regulator of two new efflux pumps in *Staphylococcus aureus*. J Bacteriol. Apr. 2005;187(7):2395-405.
Truong-Bolduc, et al. NorC, a new efflux pump regulated by MgrA of *Staphylococcus aureus*. Antimicrob Agents Chemother. Mar. 2006;50(3):1104-7.
Truong-Bolduc, et al. Transcriptional profiling analysis of the global regulator NorG, a GntR-like protein of *Staphylococcus aureus*. J Bacteriol. Nov. 2011;193(22):6207-14. doi: 10.1128/JB.05847-11. Epub Sep. 9, 2011.
Wainwright, et al. Photobactericidal activity of phenothiazinium dyes against methicillin-resistant strains of *Staphylococcus aureus*. FEMS Microbiol Lett. Mar. 15, 1998;160(2):177-81.
Walkty, et al. In vitro activity of plazomicin against 5,015 gram-negative and gram-positive clinical isolates obtained from patients in canadian hospitals as part of the CANWARD study, 2011-2012. Antimicrob Agents Chemother. May 2014;58(5):2554-63. doi: 10.1128/AAC.02744-13. Epub Feb. 18, 2014.
Yamada, et al. Functional gene cloning and characterization of MdeA, a multidrug efflux pump from *Staphylococcus aureus*. Biol Pharm Bull. Apr. 2006;29(4):801-4.
Yamada, et al. Gene cloning and characterization of SdrM, a chromosomally-encoded multidrug efflux pump, from *Staphylococcus aureus*. Biol Pharm Bull. Mar. 2006;29(3):554-6.
International Search Report and Written Opinion dated Sep. 7, 2016 for International Application No. PCT/US2016/028418.
National Center for Biotechnology Information. PubChem Substance Database; SID=187559863, Available at: https://pubchem.ncbi.nlm.nih.gov/substance/187559863. Accessed on Dec. 7, 2016.
Chikvaidze, et al., 30. Synthesis of 2,5'-bi-1H-indole derivatives and study of their biocidal properties. Soobshcheniya Akademii Nauk Gruzii, vol. 152, Issue: 2, pp. 307-310, Journal, 1995, Coden: Sangef.
Chikvaidze, et al., Synthesis and Antimicrobial Activity of New Derivatives of 2-Phenylindone, Pharmaceutical Chemistry Journal, vol. 28, No. 10, 1994.
Jani, et al., Synthesis of 3-(p-diazobenzoyi-N -arylidinohydrazone) indoles. Journal of the Indian Chemical Society. 1990; 67(7): 601-602.
Joshi, et al., Syntheses of Some New Fluorine Containing Indole Derivatives and Their Antibacterial Activity. Agricultural and Biological Chemistry. Sep. 9, 2014; 43(1): 171-173.
Kumar, et al., Synthesis, in vitro antimicrobial, antiproliferative, and QSAR studies of N-(substituted phenyl)-2/4-(1H-indol-3-ylazo)-benzamides. Med Chem Res (2013) 22:1957-1971.
Magedov, et al., Antiproliferative activity of 2,3-disubstituted indoles toward apoptosis-resistant cancers cells. Bioorg. Med. Chem. Lett. 23 (2013) 3277-3282.
Ozturk, et al., Toxicological effect of indole and its azo dye derivatives on some microorganisms under aerobic conditions. Science of the Total Environment 358 (2006) 137-142.
Samsoniya, et al., Synthesis and Antimicrobial Activity of a Number of Pyrroloindole Derivatives. Pharmaceutical Chemistry Journal, vol. 45, No. 1, Apr. 2011 (Russian Original vol. 45, No. 1, Jan. 2011).
Seferoglu, et al., Synthesis, spectral characterisation and antimicrobal activity of new diazo dyes derived from heterocyclic coupling components. Coloration technology : the journal of the Society of Dyers and Colourists .2008; 124: 27-35.
Sharma, et al. A facile synthesis of N-phenyl-6-hydroxy-3-bromo-4-arylazo quinolin-2-ones under phase transfer catalytic conditions and studies on their antimicrobial activities. Indian Journal of Chemistry vol. 45B, Sep. 2006, pp. 2077-2082.

\* cited by examiner

ANTIBIOTIC SENSITIVITY-RESTORING AND PHOTOSENSITIVE AGENTS

CROSS REFERENCE

This application claims the benefit of U.S. Provisional Application No. 62/149,738, filed Apr. 20, 2015, and U.S. Provisional Application No. 62/306,165, filed Mar. 10, 2016, each of which is incorporated herein by reference in its entirety.

GOVERNMENT RIGHTS

The invention was made with government support under RR016480-12 by the National Center for Research Resources and under GM103451-12 by the National Institutes of Health. The government has certain rights in the invention.

BACKGROUND

Antibiotics have become a mainstay of anti-microbial therapy, especially in treatment of bacterial infections. However, overuse of antibiotics has led to the emergence of drug-resistant bacteria due to antibiotic effectiveness and ease of access. The pathogenic bacteria that were initially sensitive to specific antibiotics are rapidly evolving to evade targeting by antibiotics. The development of a therapy that can combat the emergence of drug-resistant bacteria can assist in controlling the widespread evolution of pathogenic microbes.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, the invention provides a method of treating a condition, the method comprising administering to a subject in need thereof a therapeutically-effective amount of a compound that binds a biological structure, thereby decreasing drug resistance in a cell, and a therapeutically-effective amount of a second agent.

In some embodiments, the invention provides a compound of the formula:

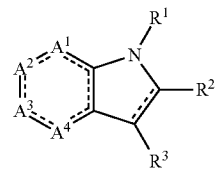

wherein:
R$^1$ is hydrogen or an ester group;
R$^2$ is hydrogen, halogen, or L$^1$-Ar$^1$;
R$^3$ is hydrogen, halogen, or L$^2$-Ar$^2$;
or R$^2$ and R$^3$ together with the atoms to which R$^2$ and R$^3$ are bound form a substituted or unsubstituted ring;
each L$^1$ and L$^2$ is independently a linking group or a bond;
each Ar$^1$ is a substituted or unsubstituted aryl group;
each Ar$^2$ is a substituted or unsubstituted aryl group wherein Ar$^2$ is not substituted with an amide, amine, nitro, imine, or ester group;
each A$^1$, A$^2$, A$^3$, and A$^4$ is independently C(R$^{1a}$), C(R$^{1a}$)(R$^{1b}$), N, or N(R$^{1a}$);
each R$^{1a}$ and R$^{1b}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted; and
each ═══ is independently a single or double bond,
or a pharmaceutically-acceptable salt thereof, wherein the compound is not:

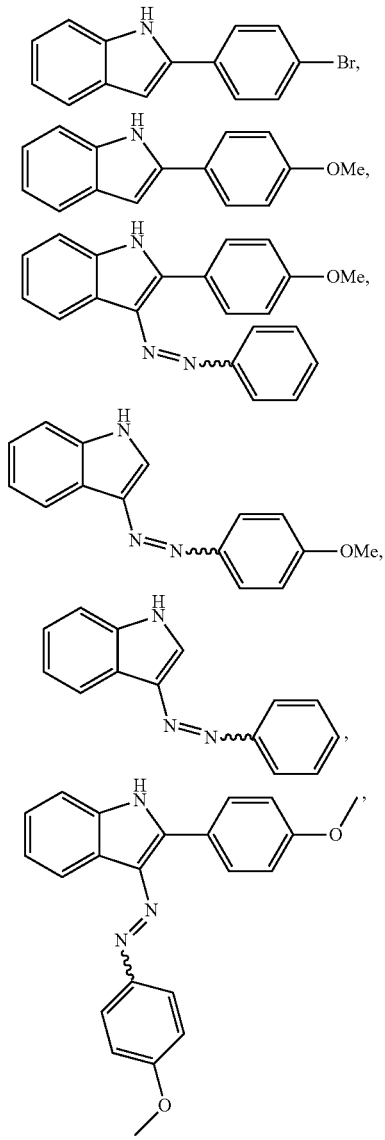

-continued

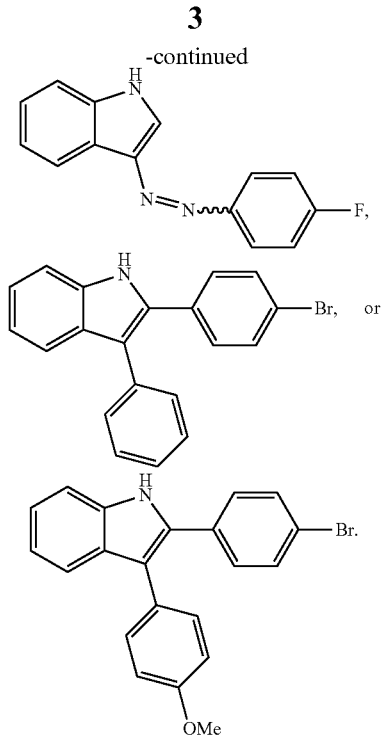

DETAILED DESCRIPTION

Figure 1:
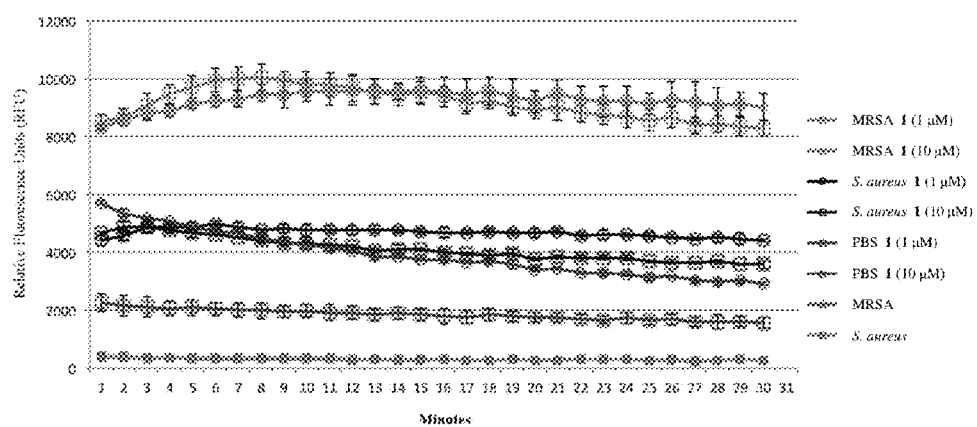
FIG. 1 depicts a fluorescent binding assay for a compound of the invention.

Antibiotics.

Antibiotics are used globally as therapy in the treatment of, for example, bacterial infections. Antibiotics can also be effective against some fungi and protozoa. Antibiotics can be classified as bacteriostatic, wherein the antibiotic inhibits reproduction of the bacteria, and bactericidal, wherein the antibiotic kills the bacteria. Antibiotics can be further classified by mechanism of action, which can include, for example, inhibition of bacterial cell wall synthesis, inhibition of bacterial cell membrane synthesis, inhibition of essential bacterial enzymes, inhibition of cell division, inhibition of peptidoglycan synthesis, inhibition of protein synthesis via binding to a 30S or 50S subunit of bacterial ribosome, inhibition of isoprenyl pyrophosphate, inhibition of folate synthesis, and production of toxic free radicals.

Antibiotics can be used to treat bacterial infections. Antibiotics can also be used prophylactically for a subject, for example, having a wound that is likely to become infected, a subject about to undergo surgery, a subject about to receive dental treatment, or a subject who suffers from recurring infections including, for example, cellulitis, urinary tract infections, and rheumatic fever.

Overuse of antibiotics in the healthcare and agricultural industries, and misuse of antibiotics, including use of antibiotics in the treatment of viral infections, cessation of antibiotic therapy prior to end of prescribed period, and prophylactic use of antibiotics by travelers, has led to the emergence of drug-resistant bacteria. Mutations that can help bacteria survive treatment with an antibiotic can quickly become prevalent throughout a bacterial population, and genetic elements encoding resistance mechanisms can be transferred between bacterial species.

Mechanisms of Bacterial Resistance to Antibiotics.

Bacteria can use various mechanisms to avoid killing by an antibiotic. Bacteria can, for example, modify the protein targeted by the antibiotic, enzymatically inactivate the antibiotic, decrease the ability of the antibiotic to enter the cell, transfer resistance genes between organisms via conjugation, transduction, or transformation, or increase the exit of the antibiotic from the cell using efflux pumps.

Efflux pumps are transport proteins found in both Gram-positive and Gram-negative bacteria. Five major classes of efflux pumps can exist in prokaryotes including, for example, major facilitator (MF), multidrug and toxic efflux (MATE), resistance-nodulation-division (RND), small multidrug resistance (SMR), and ATP binding cassette (ABC). Efflux pumps can be specific for a single substrate or transport a range of structurally-similar or -dissimilar compounds, including antibiotics. Increased expression of efflux pumps can be correlated with resistance to associated substrates. Efflux pumps can also be used to transport, for example, toxins, metabolites, drugs, lipophilic cationic drugs, bile acids, fatty acids, and lipids.

One mechanism that can be employed by drug-resistant bacteria is multi-drug efflux via membrane transporter proteins known as multidrug efflux systems (MES), which can recognize more than one substrate. The MES can be classified as, for example, ABC, MATE, RND, SMR, and the multiantimicrobial extrusion protein family. In Gram-positive bacteria, the major efflux systems are the chromosomally encoded Major Facilitator Superfamily (MFS), Nor-family (NorA, NorB, NorC), and the MdeA the MATE mepRAB (multidrug export protein and the SMR SepA) family. The Gram-positive efflux systems can have overlapping specificities and can accept a large variety of structurally unrelated antibiotics including, for example, quinolones, tetracyclines, and monovalent and divalent antimicrobial cations, which can include intercalating dyes, quaternary ammonium compounds, diamidines, biguanidines, and plant secondary metabolites.

Non-limiting examples of efflux systems in Gram-negative bacteria include CraA and AmvA, which mediate antimicrobial and disinfectant resistance in *A. baumannii*, and MdfA of *E. coli*. The MFS and ABC efflux system super families can be commonly found among resistant strains of mycobacteria, including *Mycobacterium tuberculosis*.

The development of new strategies to target drug-resistant bacteria can be applied to especially-virulent strains of bacteria, which can cause severe and widespread infection in nursing homes and hospitals, and are not susceptible to standard antibiotic treatment. For example, *Staphylococcus aureus* can be a dangerous and versatile opportunistic pathogen. *S. aureus* can cause, for example, superficial skin infections resulting from cuts, abrasions, turf burns, and severe invasive diseases. Originally responsive to penicillin, a number of *S. aureus* strains are now resistant to various classes of antibiotics including, for example, β-lactams, macrolides, and vancomycin.

Methicillin-resistant (MRSA) and vancomycin-resistant *S. aureus* (VRSA) are a significant health threat and constitute a major cause of mortality from bacterial infections. Several chromosomally-encoded efflux systems can be present in MRSA including, for example, NorA, NorB, NorC, MepA, MdeA, SepA, SdrM, and LmrS. LmrS can expel, for example, ampicillin. Some of the plasmid-mediated efflux systems found in MRSA can include, for example, QacA, QacB, Smr, QacG, QacH, and QacJ. Some strains of MRSA can carry more than one efflux system.

Compounds of the Invention.

The present compounds can potentiate the effects of many functionally- and mechanistically-diverse antibiotics against, for example, MRSA, which displays efflux-mediated resistance to antibiotics. The present compounds can display synergy with antibiotics including, for example, polymyxin B (PMB) against Gram-negative bacterial strains.

Compounds of the invention can increase the potency of antibiotics. For example, the mean inhibitory concentrations (MIC) for a compound of the invention and ampicillin were determined to be about 200 µM and about 4579 µM, respectively. When the compound was used in combination with ampicillin, the concentration of the compound needed for full killing was 3 µM, a 127-fold decrease in concentration, and the concentration of ampicillin needed was reduced to about 572 µM, an 8-fold decrease in concentration. The ability of compounds of the invention to synergize with structurally and mechanistically unrelated antibiotics can be a result of the inhibition of bacterial efflux. Thus, the discovered potentiation of antibiotic activity with 2,3-di-((E)-2-arylethenyl)indoles can restore the activity of antibiotics rendered inactive against MRSA, or other bacterial strains, due to the increased presence of bacterial efflux pumps.

Non-limiting examples of compounds of the invention include compounds of any of the following formulae:

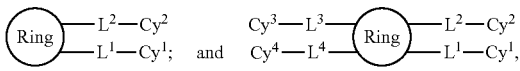

or a pharmaceutically-acceptable salt thereof, wherein: RING is a ring system; each of $Cy^1$, $Cy^2$, $Cy^3$, and $Cy^4$ is independently a cyclic group; and each of $L^1$, $L^2$, $L^3$, and $L^4$ is independently a linking group.

Non-limiting examples of cyclic groups or of a ring system include aromatic, non-aromatic, heterocyclic, carbocyclic, monocyclic, and polycyclic groups. A polycyclic group can be, for example, bicyclic, tricyclic, or tetracyclic. A polycyclic group can be, for example, fused, bridged, or spiro, or any combination thereof. Non-limiting examples of aromatic groups include heterocyclic, carbocyclic, monocyclic, and polycyclic rings. Any such group can be substituted or unsubstituted at any position, with any number of substituents. Non-limiting examples of substituents include: halogens, hydroxyl groups, sulfhydryl groups, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, epoxides, ester groups, and any other substituent described herein.

A linking group can be any chemical group that attaches groups of the structure together. A linking group can comprise, for example, an alkylene group, an alkenylene group, an alkynylene group, a polyether, such as polyethylene glycol (PEG), a polyester, a polyamide, or a polyamine, any of which being unsubstituted or substituted with any number of substituents, such as halogens, hydroxyl groups, sulfhydryl groups, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, epoxides, ester groups, and any other substituent described herein.

Non-limiting examples of compounds of the invention include compounds of any of the following formulae:

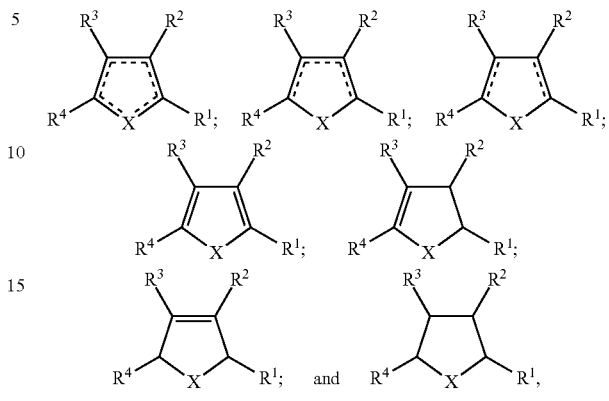

or a pharmaceutically-acceptable salt thereof, wherein: X is N, NH, $NR^N$, S, or O; each ═══ is independently a single bond or a double bond; $R^N$ is hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted, or H; $R^1$ is H or $-L^1-Cy^1$; $R^2$ is H or $-L^2-Cy^2$; $R^3$ is H or $-L^3-Cy^3$; $R^4$ is H or $-L^4-Cy^4$; or $R^1$ and $R^2$ together with the atoms to which $R^1$ and $R^2$ are bound form a ring; $R^2$ and $R^3$ together with the atoms to which $R^2$ and $R^3$ are bound form a ring; or $R^3$ and $R^4$ together with the atoms to which $R^3$ and $R^4$ are bound form a ring; or $R^1$ and $R^2$ together with the atoms to which $R^1$ and $R^2$ are bound form a first ring and $R^3$ and $R^4$ together with the atoms to which $R^3$ and $R^4$ are bound form a second ring; each of $L^1$, $L^2$, $L^3$, and $L^4$ is independently a linking group; and each of $Cy^1$, $Cy^2$, $Cy^3$, and $Cy^4$ is independently a cyclic group.

Non-limiting examples of compounds of the invention include compounds of any of the following formulae:

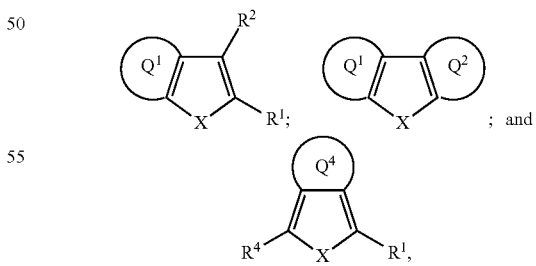

or a pharmaceutically-acceptable salt thereof, wherein: X is N, NH, $NR^N$, S, or O; each of $Q^1$, $Q^2$, $Q^3$, and $Q^4$ is independently a ring system; $R^1$ is H or $-L^1-Cy^1$; $R^2$ is H or $-L^2-Cy^2$; and $R^4$ is H or $-L^4-Cy^4$.

Non-limiting examples of compounds of the invention include compounds of any of the following formulae:

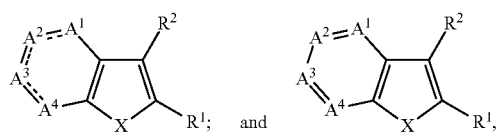

or a pharmaceutically-acceptable salt thereof, wherein: X is N, NH, HR$^N$, S, or O; each ═══ is independently a single bond or a double bond; R$^N$ is hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted, or H; R$^1$ is H or -L$^1$-Cy$^1$; R$^2$ is H or -L$^2$-Cy$^2$; A$^1$ is C(R$^{1a}$), C(R$^{1a}$)(R$^{1b}$), N, or N(R$^{1a}$); A$^2$ is C(R$^{2a}$), C(R$^{2a}$)(R$^{2b}$), N, or N(R$^{2a}$); A$^3$ is C(R$^{3a}$), C(R$^{3a}$)(R$^{3b}$), N, or N(R$^{3a}$); A$^4$ is C(R$^{4a}$); C(R$^{4a}$)(R$^{4b}$), N, or N(R$^{4a}$); each R$^{1a}$, R$^{1b}$, R$^{2a}$, R$^{2b}$, R$^{3a}$, R$^{3b}$, R$^{4a}$, and R$^{4b}$ is independently: halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted, or H, or absent, or R$^{1a}$ and R$^{1b}$ together form a carbonyl, a thiocarbonyl, an imine, or an olefin, or R$^{2a}$ and R$^{2b}$ together form a carbonyl, a thiocarbonyl, an imine, or an olefin, or R$^{3a}$ and R$^{3b}$ together form a carbonyl, a thiocarbonyl, an imine, or an olefin, or R$^{4a}$ and R$^{4b}$ together form a carbonyl, a thiocarbonyl, an imine, or an olefin; each of L$^1$ and L$^2$ is independently a linking group; and each of Cy$^1$ and Cy$^2$ is independently a cyclic group.

In some embodiments, a bond of the compound, such as the bond connecting A$^1$ and A$^2$, the bond connecting A$^2$ and A$^3$, or the bond connecting A$^3$ and A$^4$, is fused to an additional ring system.

Non-limiting examples of compounds of the invention include compounds of any of the following formulae:

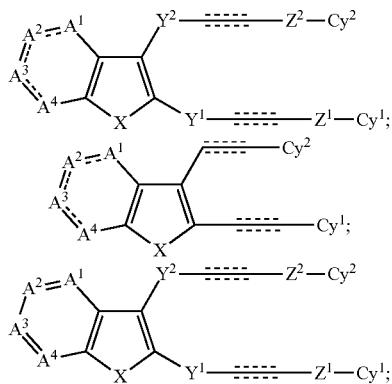

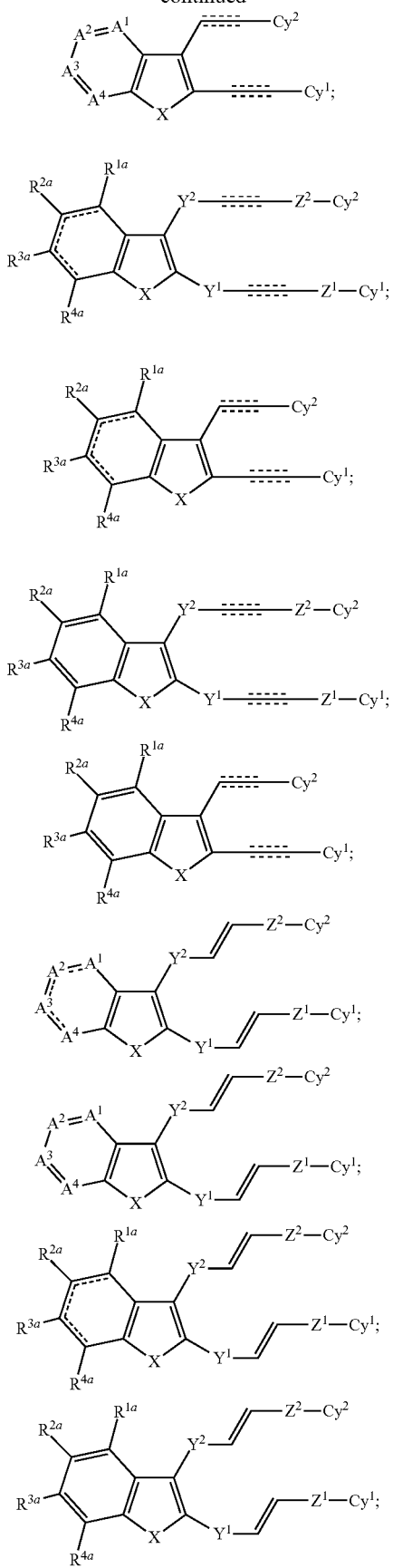

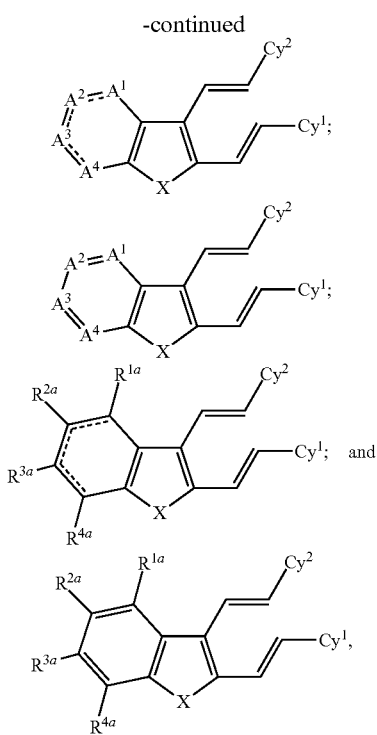

or a pharmaceutically-acceptable salt thereof, wherein: each $Y^1$, $Y^2$, $Z^1$, and $Z^2$ is independently: a bond, an alkylene group, an alkenylene group, an alkynylene group, an amino linkage, and ether linkage, a thioether linkage, an ester linkage, a thioester linkage, an amide linkage, a carbamate linkage, a carbonate linkage, a ureido linkage, a sulfoxide linkage, a sulfone linkage, a sulfonamide linkage, or an imine linkage; each ==== is independently a single, double, or triple bond; and all other variables are as described previously.

Non-limiting examples of a cyclic group, such as $Cy^1$ or $Cy^2$, include groups of any of the following formulae:

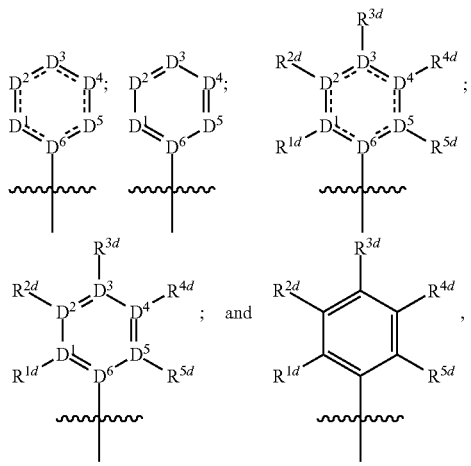

wherein: each ==== is independently a single bond or a double bond; each $D^1$ is independently $C(R^{D1a})$, $C(R^{D1a})(R^{D1b})$, N, or $N(R^{D1a})$; each $D^2$ is independently $C(R^{D2a})$, $C(R^{D2a})(R^{D2b})$, N, or $N(R^{D2a})$; each $D^3$ is independently $C(R^{D3a})$, $C(R^{D3a})(R^{D3b})$, N, or $N(R^{D3a})$; each $D^4$ is independently $C(R^{D4a})$, $C(R^{D4a})(R^{D4b})$, N, or $N(R^{D4a})$; each $D^5$ is independently $C(R^{D5a})$, $C(R^{D5a})(R^{D5b})$, N, or $N(R^{D5a})$; each $D^6$ is independently $C(R^{D6a})$, C, or N; each $R^{D1a}$, $R^{D1b}$, $R^{D2a}$, $R^{D2b}$, $R^{D3a}$, $R^{D3b}$, $R^{D4a}$, $R^{D4b}$, $R^{D5a}$, $R^{D5b}$, and $R^{D6a}$ is independently: halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted, or H, or absent, or $R^{D1a}$ and $R^{D1b}$ together form a carbonyl, a thiocarbonyl, an imine, or an olefin, or $R^{D2a}$ and $R^{D2b}$ together form a carbonyl, a thiocarbonyl, an imine, or an olefin, or $R^{D3a}$ and $R^{D3b}$ together form a carbonyl, a thiocarbonyl, an imine, or an olefin, or $R^{D4a}$ and $R^{D4b}$ together form a carbonyl, a thiocarbonyl, an imine, or an olefin, or $R^{D5a}$ and $R^{D5b}$ together form a carbonyl, a thiocarbonyl, an imine, or an olefin.

In some embodiments, a bond of the compound, such as the bond connecting $D^1$ and $D^2$, the bond connecting $D^2$ and $D^3$, the bond connecting $D^3$ and $D^4$, or the bond connecting $D^4$ and $D^5$, is fused to an additional ring system.

Non-limiting examples of a cyclic group, such as $Cy^1$ or $Cy^2$, include groups of any of the following formulae:

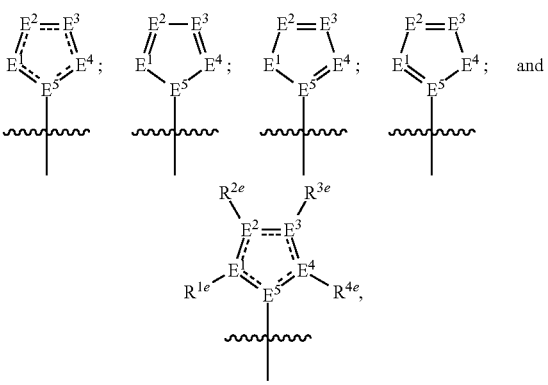

wherein: each ==== is independently a single bond or a double bond; each $E^1$ is independently $C(R^{E1a})$, $C(R^{E1a})(R^{E1b})$, N, $N(R^{E1a})$, S, or O; each $E^2$ is independently $C(R^{E2a})$, $C(R^{E2a})(R^{E2b})$, N, $N(R^{E2a})$, S, or O; each $E^3$ is independently $C(R^{E3a})$, $C(R^{E3a})(R^{E3b})$, N, $N(R^{E3a})$, S, or O; each $E^4$ is independently $C(R^{E4a})$, $C(R^{E4a})(R^{E4b})$, N, $N(R^{E4a})$, S, or O; each $E^5$ is independently $C(R^{E5a})$, C, or N; each $R^{E1a}$, $R^{E1b}$, $R^{E2a}$, $R^{E2b}$, $R^{E3a}$, $R^{E3b}$, $R^{E4a}$, $R^{E4b}$, and $R^{E5a}$ is independently: halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted, or H, or $R^{E1a}$ and $R^{E1b}$ together form a carbonyl, a thiocarbonyl, an imine, or an olefin, or $R^{E2a}$ and $R^{E2b}$ together form a carbonyl, a thiocarbonyl, an imine, or an olefin, or $R^{E3a}$ and $R^{E3b}$ together form a carbonyl, a thiocarbonyl, an imine, or an olefin, or $R^{E4a}$ and $R^{E4b}$ together form a carbonyl, a thiocarbonyl, an imine, or an olefin.

In some embodiments, a bond of the compound, such as the bond connecting $E^1$ and $E^2$, the bond connecting $E^2$ and $E^3$, or the bond connecting $E^3$ and $E^4$, is fused to an additional ring system.

Non-limiting examples of a cyclic group, such as $Cy^1$ or $Cy^2$, include groups of the following moieties, any of which is unsubstituted or substituted with any substituent described herein: cyclopropyl, cyclobutyl, cyclopentyl, cyclopentenyl, cyclohexyl, cyclohexenyl, cycloheptyl, cycloheptenyl, cyclooctyl, cyclooctenyl, cyclopenta-1,3-dienyl, cyclohexa-1,3-dienyl, cyclohexa-1,4-dienyl, cyclohepta-1,3-dienyl, cyclohepta-1,4-dienyl, bicyclo[3.2.0]heptanyl, octahydropentalenyl, octahydro-1H-indenyl, decahydroazulenyl, bicyclo[4.2.0]octanyl, decahydronaphthalenyl, decahydro-1H-benzo[7]annulenyl, dodecahydro-1H-fluorenyl, tetradecahydroanthracenyl, tetradecahydrophenanthrenyl, dodecahydros-indacenyl, dodecahydro-as-indacenyl, dodecahydro-1H-cyclopenta[b]napthalenyl, dodecahydro-1H-cyclopenta[a]napthalenyl, 1,2,3,4-tetrahydronaphthalenyl, 4,5,6,7-tetrahydro-1H-indenyl, 2,3-dihydro-1H-indenyl, spiro[4.5]decanyl, spiro[5.5]undecanyl, spiro[4.4]nonanyl, spiro[2.5]octanyl, 9,10-dihydroanthracenyl, 4,9-dihydro-1H-cyclopenta[b]napthalenyl, 9H-fluorenyl, (1Z,3Z,5Z)-cyclohepta-1,3,5-triene, benzimidazolyl, indolyl, indolinyl, indazolyl, isoxazolyl, 4-azaindolyl, 7-azaindolyl, imidazopyrimidinyl, benzofuranyl, benzothiophenyl, quinolinyl, isoquinolinyl, quinazolinyl, quinoxalinyl, purinyl, quinolizinyl, cinnolinyl, indolizinyl, phthalazinyl, isoindolyl, pteridinyl, benzofurazanyl, benzothiazolyl, benzoxazolyl, naphthyridinyl, furopyridinyl, benzoquinonyl, anthraquinonyl, 1,4-napthoquinonyl, acridinyl, azulenyl, indenyl, decalinyl, xanthenyl, 2H-chromenyl, dibenzofuranyl, dibenzopyrrolyl, phenoxazinyl, phenazinyl, phenoxathiinyl, phenyl, naphthalenyl, anthracenyl, phenanthrenyl, chrysenyl, pyrenyl, indanyl, tetralinyl, fluorenyl, acenaphthylenyl, acenaphthrene, fluoranthenyl, triphenylenyl, norbornanyl, 3-azabicyclo[3.1.0]hexanyl, 3-azabicyclo[4.1.0]heptanyl, 1,4-dihydro-1,4-ethanoanthracenyl, 1,4,5,8-tetrahydro-1,4,5,8-dimethanoanthracenyl, bicyclo[2.2.1]heptanyl, bicyclo[2.2.1]hept-2-enyl, bicyclo[2.2.2]octanyl, bicyclo[2.2.2]oct-2-enyl, bicyclo[2.2.1]heptanyl, bicyclo[3.1.1]heptanyl, bicyclo[4.4.0]decanyl, adamantanyl, quinuclidinyl, oxiranyl, oxetanyl, 2-tetrahydrofuranyl, 3-tetrahydrofuranyl, 2-tetrahydropyranyl, 3-tetrahydropyranyl, 4-tetrahydropyranyl, oxepanyl, oxocanyl, furanyl, 4H-pyranyl, (2Z,4Z,6Z)-oxepinyl, furfuralyl, dihydrofuranyl, dihydropyranyl, 1,3-dioxolanyl, 1,4-dioxanyl, 1,3-dioxanyl, 1,2-dioxanyl, aziridinyl, azetidinyl, pyrrolidinyl, 1-pyrrolidinyl, 2-pyrrolidinyl, 3-pyrrolidinyl, 1-piperidinyl, 2-piperidinyl, 3-piperidinyl, 4-piperidinyl, azepanyl, azocanyl, piperidino, homopiperidinyl, 2-pyrrolinyl, 3-pyrrolinyl, 2H-pyranyl, 4H-pyranyl, pyrazolidinyl, furazanyl, piperidinyl-N-oxide, morpholinyl-N-oxide, 1-oxo-1-thiomorpholinyl, 1,1-dioxo-1-thiomorpholinyl, pyrrolyl, (2Z,4Z,6Z)-1H-azepinyl, imidazolyl, pyrazolyl, 1,2,3-triazolyl, 1,2,4-triazolyl, 1,3,4-oxadiazolyl, 1,2,5-oxadiazolyl, 1,3,4-thiadiazolyl, tetrazolyl, isothiazolyl, pyridinyl, pyrimidinyl, pyridazinyl, pyrazinyl, triazinyl, 1-piperazinyl, 2-piperazinyl, 1,4-dihydropyrazinyl, 2-morpholinyl, 3-morpholinyl, 4-morpholinyl, morpholino, oxazolyl, thiazolyl, pyrrolidonyl, azetidinonyl, piperidinonyl, 4-thiazolidinyl, 2H-imidazol-2-one, phthalimidine, benzoxanyl, benzo[1,3]dioxinyl, benzo[1,4]dionyl, benzopyrrolidinyl, benzopiperidinl, benzoxolanyl, benzothiolanyl, 4,5,6,7-tetrahydropyrazol[1,5-a]pyridinyl, benzothianyl, oxazepinyl, diazepinyl, thiazepinyl, 1,2,3,6-tetrahydropyridinyl, pyrazolinyl, imidazolinyl, imidazolidinyl, thiiranyl, thietanyl, 2-tetrahydrothiophenyl, 3-tetrahydrothiophenyl, tetrahydrothiopyranyl, thiepanyl, thiocanyl, thiepinyl, thiophenyl, 4H-thiopyranyl, 1,4-dithiinyl, 1,4-dithianyl, 2-thiomorpholinyl, 3-thiomorpholinyl, 4-thiomorpholinyl, thiomorpholino, 1,3-dithiolanyl, dihydrothienyl, thienyl, silolyl, 3,4,5,6-tetrahydro-2H-azepinyl, 1,4-thiazepinyl, azocinyl, azonanyl, thioninyl, azecinyl, dihydrofuran-2(3H)-onyl, 2,3-dioxolan-2-onyl, pyrrolidin-2-onyl, imidazolidin-2-onyl, piperidin-2-onyl, 1,3-oxazinan-2-onyl, phthalic anhydridyl, oxindolyl, indoline-2,3-dionyl, and 2,5-dihydrofuranyl.

Non-limiting examples of compounds of the invention include compounds of the following formula:

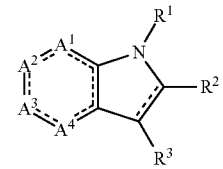

wherein: $R^1$ is hydrogen or an ester group; $R^2$ is hydrogen, halogen, or $L^1$-$Ar^1$; $R^3$ is hydrogen, halogen, or $L^2$-$Ar^2$; or $R^2$ and $R^3$ together with the atoms to which $R^2$ and $R^3$ are bound form a substituted or unsubstituted ring; each $L^1$ and $L^2$ is independently a linking group or a bond; each $Ar^1$ is independently a substituted or unsubstituted aryl group wherein $Ar^2$ is not substituted with an amide, amine, nitro, imine, or an ester; each $Ar^2$ is independently a substituted or unsubstituted aryl group wherein $Ar^2$ is not substituted with an amide, amine, nitro, imine, or an ester; each $A^1$, $A^2$, $A^3$, and $A^4$ is independently $C(R^{1a})$, $C(R^{1a})(R^{1b})$, N, or $N(R^{1a})$; each $R^{1a}$ and $R^{1b}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted; each === is independently a single or double bond, and pharmaceutically-acceptable salts thereof.

In some embodiments, when $Ar^1$ is phenyl brominated at one position, then $Ar^2$ is substituted on at least one position. In some embodiments, when $Ar^1$ is phenyl substituted with one methoxy group, then $Ar^2$ is substituted on at least one position.

In some embodiments, when $Ar^1$ is substituted, $Ar^2$ is also substituted. In some embodiments, when $Ar^1$ is unsubstituted, $Ar^2$ is substituted.

In some embodiments, both $L^1$ and $L^2$ are independently

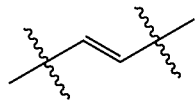

In some embodiments, both Ar$^1$ and Ar$^2$ are independently substituted with hydrogen, halogen, or aryloxy. In some embodiments, each linking group is independently alkylene, alkenylene, O, S, SO$_2$, CO, N$_2$, or a bond.

In some embodiments, each ==== is independently chosen to provide an aromatic system.

In some embodiments, non-limiting examples of compounds of the invention include compounds of the following formula:

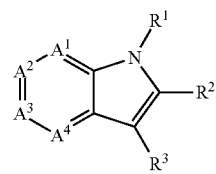

wherein: R$^1$ is hydrogen or an ester group; R$^2$ is hydrogen, halogen, or L$^1$-Ar$^1$; R$^3$ is hydrogen, halogen, or L$^2$-Ar$^2$; or R$^2$ and R$^3$ together with the atoms to which R$^2$ and R$^3$ are bound form a substituted or unsubstituted ring; each L$^1$ and L$^2$ is independently a linking group or a bond; each Ar$^1$ is independently a substituted or unsubstituted aryl group wherein Ar$^2$ is not substituted with an amide, amine, nitro, imine, or an ester; each Ar$^2$ is independently a substituted or unsubstituted aryl group wherein Ar$^2$ is not substituted with an amide, amine, nitro, imine, or an ester; each A$^1$, A$^2$, A$^3$, and A$^4$ is independently C(R$^{1a}$), C(R$^{1a}$)(R$^{1b}$), N, or N(R$^{1a}$); each R$^{1a}$ and R$^{1b}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted; and pharmaceutically-acceptable salts thereof.

In some embodiments, when Ar$^1$ is phenyl brominated at one position, then Ar$^2$ is substituted on at least one position. In some embodiments, when Ar$^1$ is phenyl substituted with one methoxy group, then Ar$^2$ is substituted on at least one position.

In some embodiments, when Ar$^1$ is substituted, Ar$^2$ is also substituted. In some embodiments, when Ar$^1$ is unsubstituted, Ar$^2$ is substituted.

In some embodiments, both L$^1$ and L$^2$ are independently

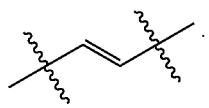 [SMILES: */C=C/*]

In some embodiments, both Ar$^1$ and Ar$^2$ are independently substituted with hydrogen, halogen, or aryloxy. In some embodiments, each linking group is independently alkylene, alkenylene, O, S, SO$_2$, CO, N$_2$, or a bond.

Non-limiting examples of compounds of the invention include the following:

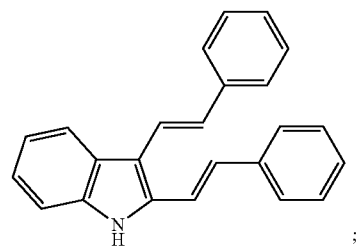

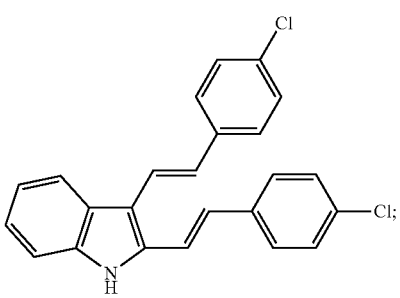

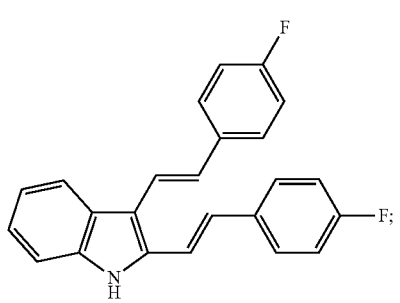

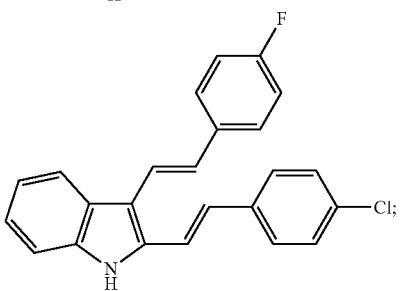

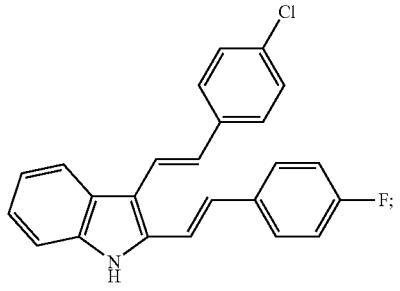

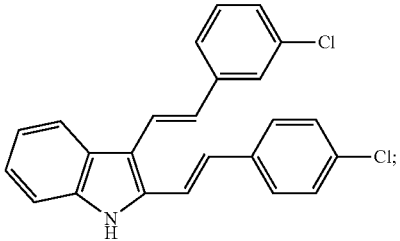

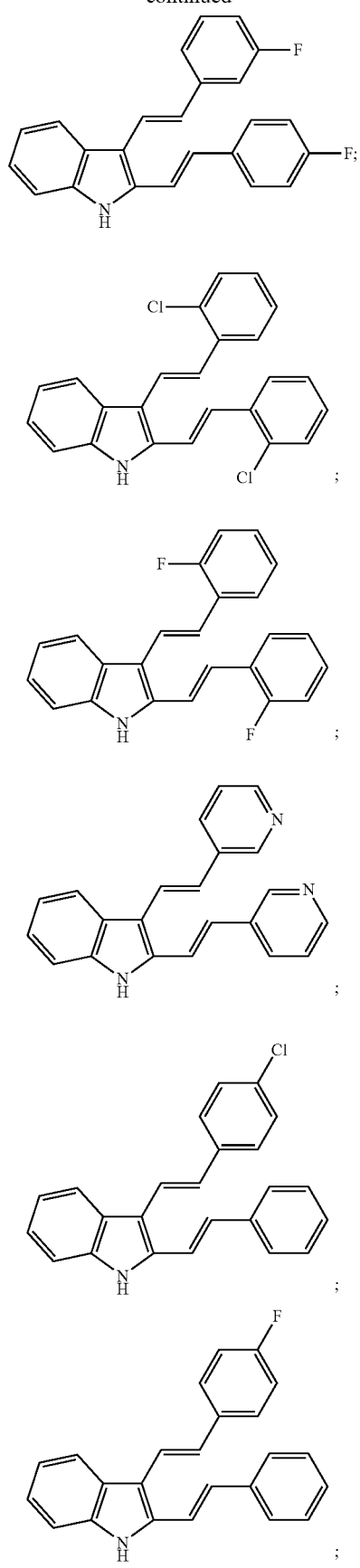
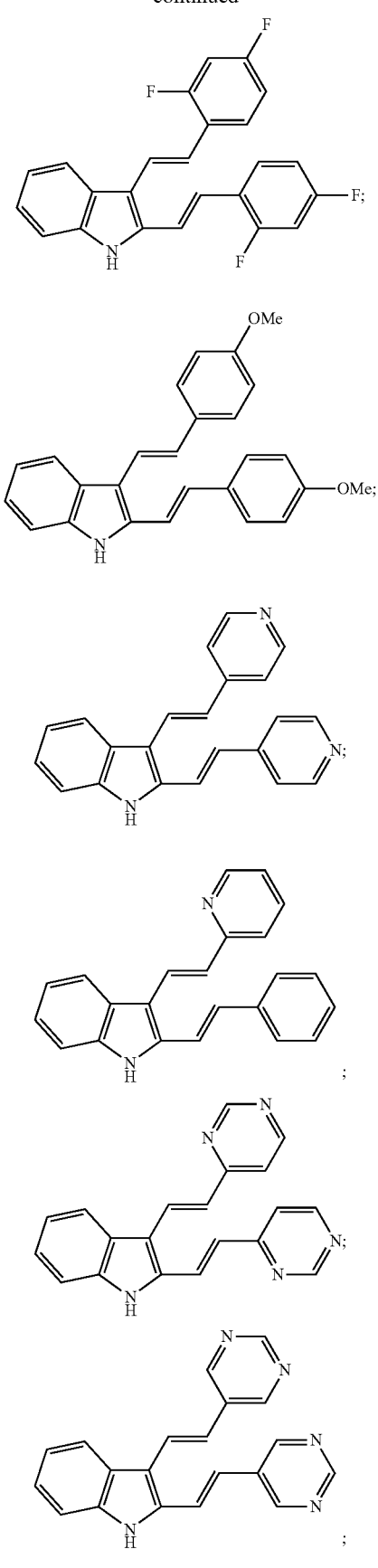

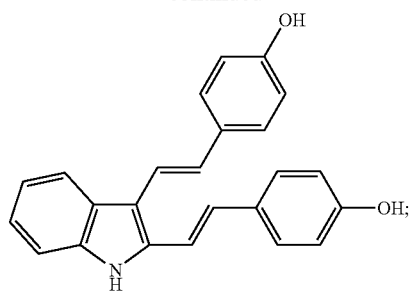
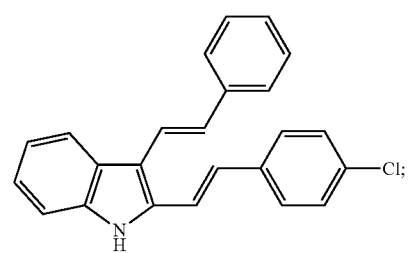
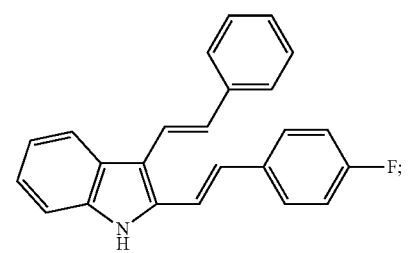
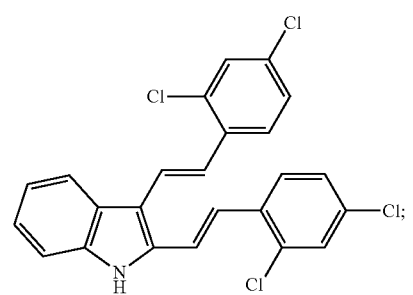
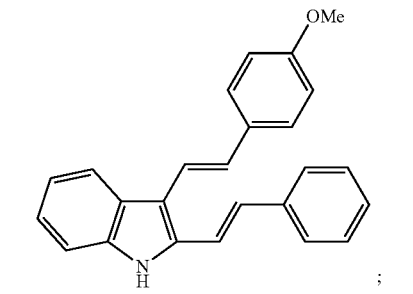
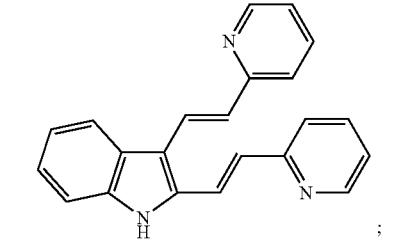
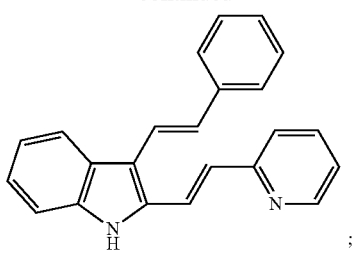
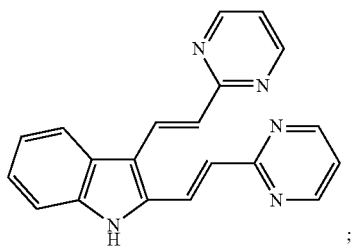
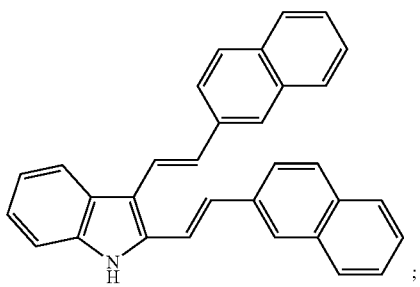
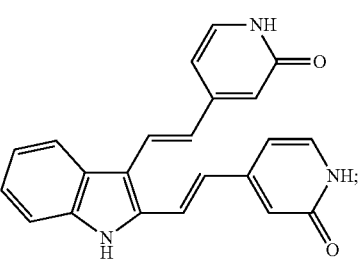
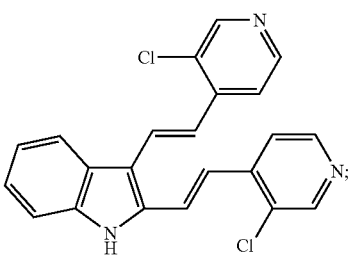
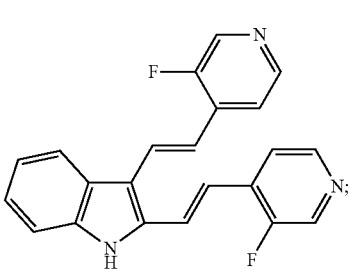

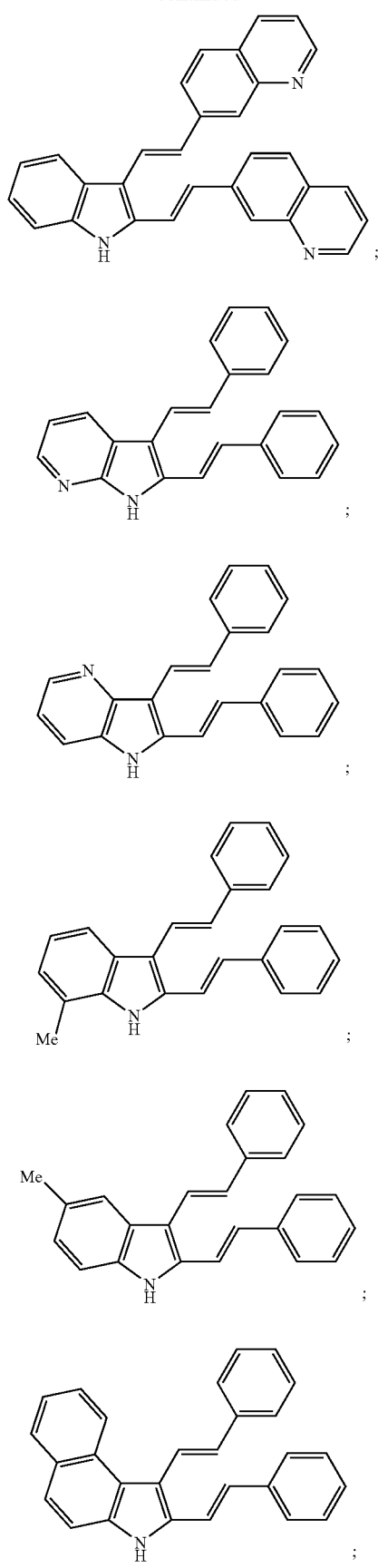 [SMILES: C(=C\c1[nH]c2ccccc2c1/C=C/c1ccc2cccnc2c1)/c1ccc2cccnc2c1 ; C(=C\c1[nH]c2ncccc2c1/C=C/c1ccccc1)/c1ccccc1 ; C(=C\c1[nH]c2cccnc2c1/C=C/c1ccccc1)/c1ccccc1 ; Cc1cccc2c(/C=C/c3ccccc3)c(/C=C/c3ccccc3)[nH]c12 ; Cc1ccc2[nH]c(/C=C/c3ccccc3)c(/C=C/c3ccccc3)c2c1 ; C(=C\c1[nH]c2ccc3ccccc3c2c1/C=C/c1ccccc1)/c1ccccc1]
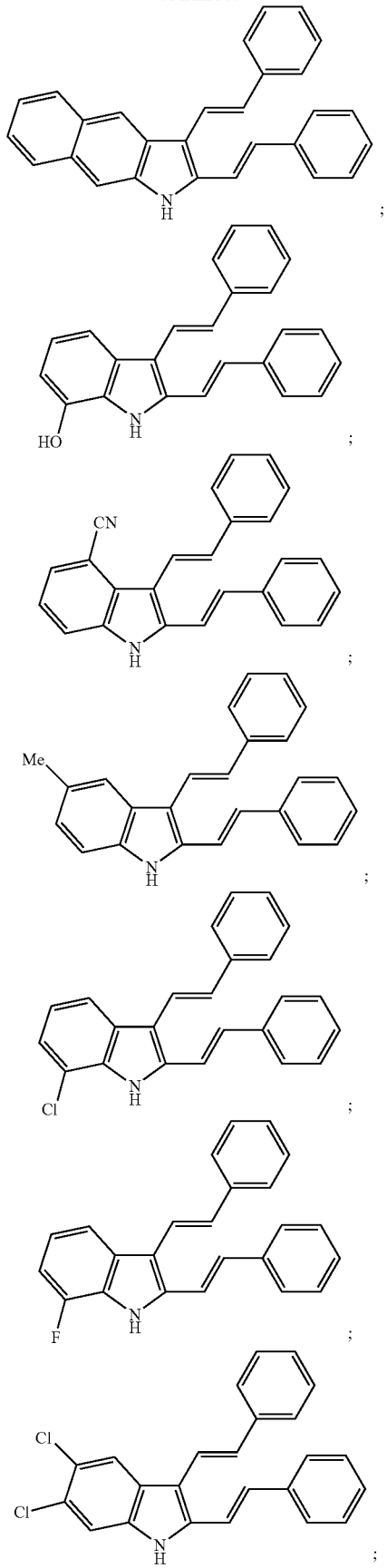

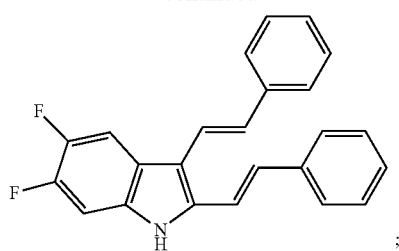
;
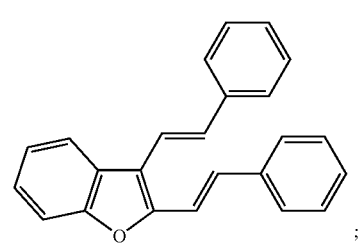
;
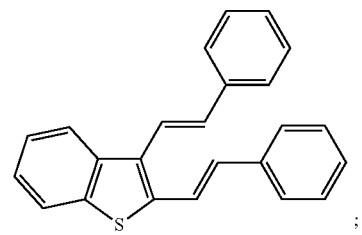
;
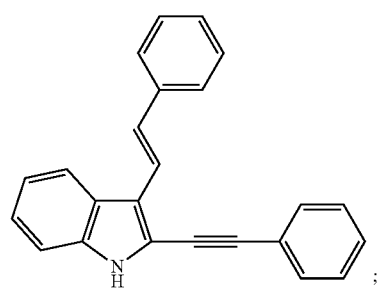
;
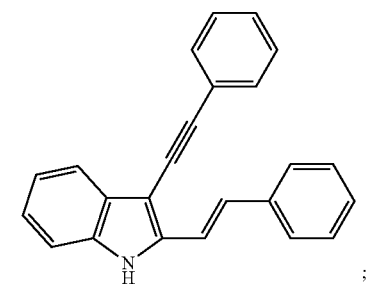
;
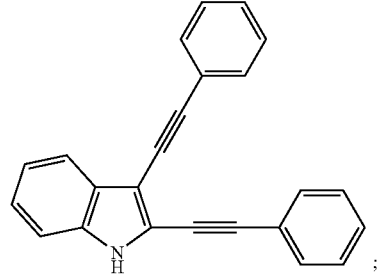
;
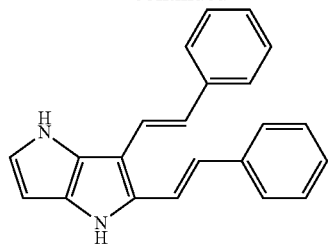
;
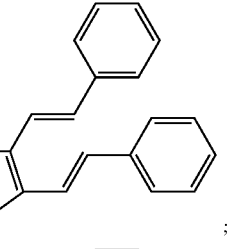
;
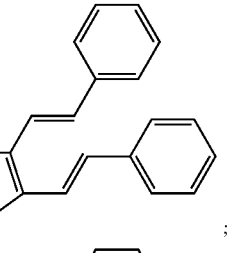
;
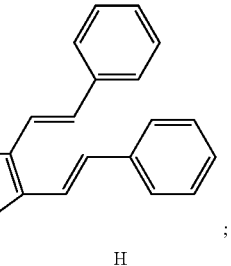
;
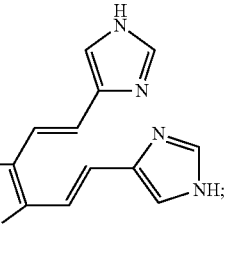
;
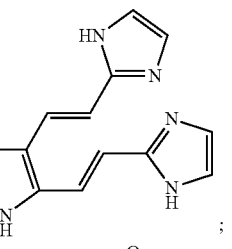
;
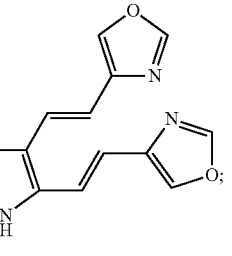
;

-continued
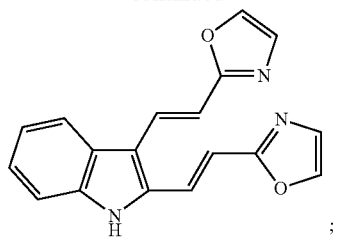
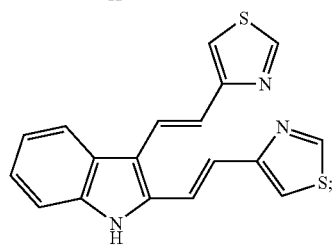
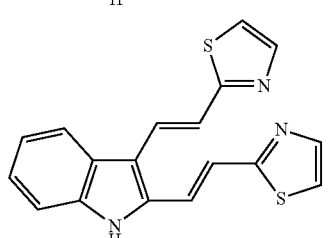
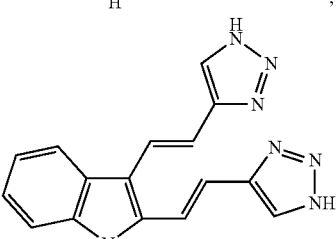
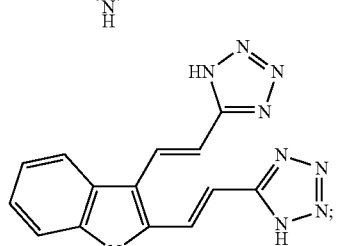
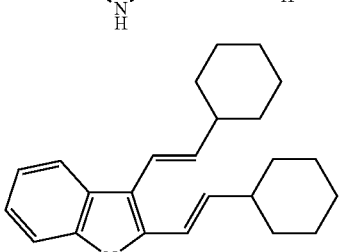
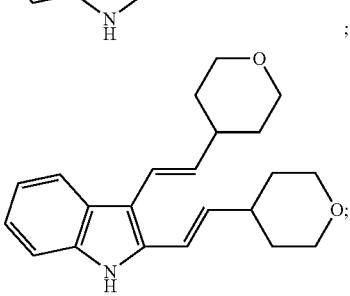
-continued
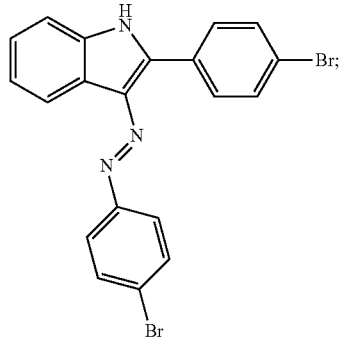
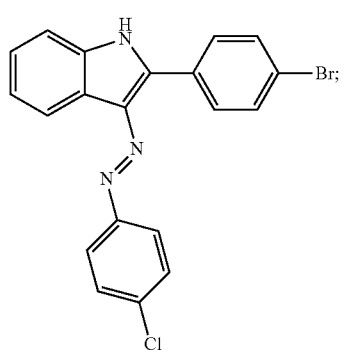
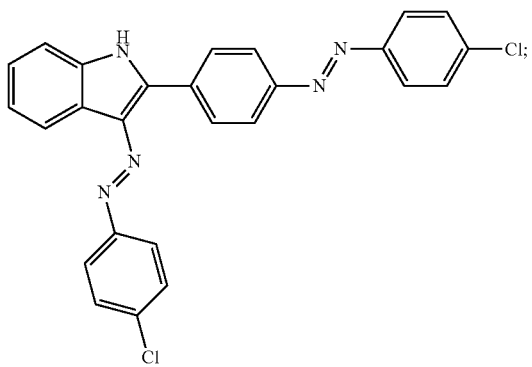
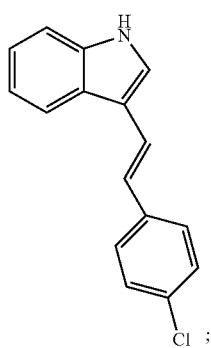

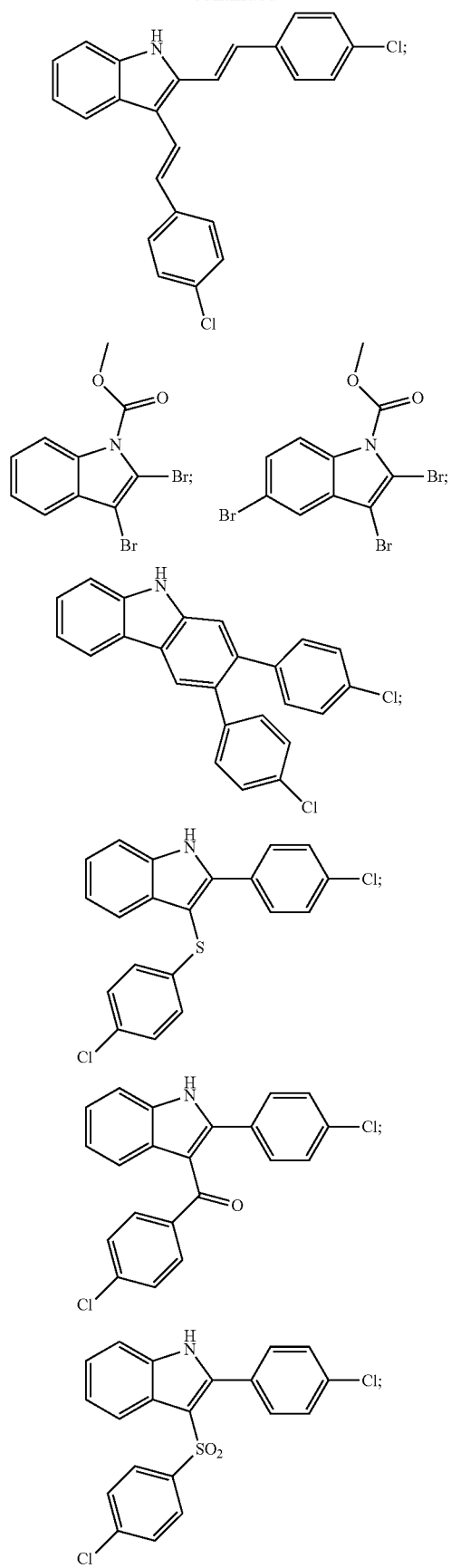
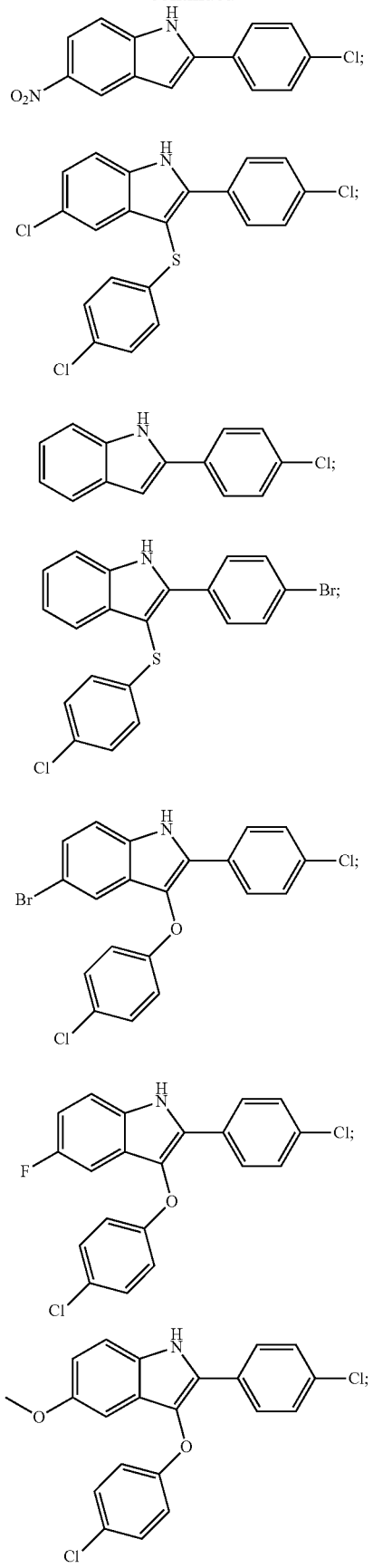

and pharmaceutically-acceptable salts thereof.

Any compound herein can be any or all stereoisomers, enantiomers, diastereomers, mixtures, racemates, atropisomers, and tautomers thereof.

A compound herein can bind a cellular target that is associated with a drug resistance mechanism, for example, an efflux pump. The binding can cause a decrease in the efficacy of the drug resistance mechanism, thereby increasing the efficacy of the compound within the cell. A compound herein can cause a decrease in efficacy of a drug resistance mechanism that is, for example, about 2-fold, about 3-fold, about 4-fold, about 5-fold, about 6-fold, about 7-fold, about 8-fold, about 9-fold, about 10-fold, about 11-fold, about 12-fold, about 13-fold, about 14-fold, about 15-fold, about 16-fold, about 17-fold, about 18-fold, about 19-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, about 100-fold, about 110-fold, about 120-fold, about 130-fold, about 140-fold, about 150-fold, about 160-fold, about 170-fold, about 180-fold, about 190-fold, about 200-fold, about 250-fold, about 300-fold, about 350-fold, about 400-fold, about 450-fold, about 500-fold, about 550-fold, about 600-fold, about 650-fold, about 700-fold, about 750-fold, about 800-fold, about 850-fold, about 900-fold, about 950-fold, about 1000-fold, about 1500-fold, or about 2000-fold in comparison to the efficacy of the drug resistance mechanism in a cell that has not been treated with the compound.

Optional Substituents for Chemical Groups.

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, urethane groups, and ester groups.

Non-limiting examples of alkyl and alkylene groups include straight, branched, and cyclic alkyl and alkylene groups. An alkyl or alkylene group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of cyclic alkyl groups include cyclopropyl, cyclobutyl, cyclopentyl, cyclohexyl, cycloheptyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl.

An aryloxy group can be, for example, an oxygen atom substituted with any aryl group, such as phenoxy.

An aralkyl group can be, for example, any alkyl group substituted with any aryl group, such as benzyl.

An arylalkoxy group can be, for example, an oxygen atom substituted with any aralkyl group, such as benzyloxy.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

An acyl group can be, for example, a carbonyl group substituted with hydrocarbyl, alkyl, hydrocarbyloxy, alkoxy, aryl, aryloxy, aralkyl, arylalkoxy, or a heterocycle. Non-limiting examples of acyl include acetyl, benzoyl, benzyloxycarbonyl, phenoxycarbonyl, methoxycarbonyl, and ethoxycarbonyl.

An acyloxy group can be an oxygen atom substituted with an acyl group. An ester or an ester group comprises an acyloxy group. A non-limiting example of an acyloxy group, or an ester group, is acetate.

A carbamate group can be an oxygen atom substituted with a carbamoyl group, wherein the nitrogen atom of the carbamoyl group is unsubstituted, monosubstituted, or disubstituted with one or more of hydrocarbyl, alkyl, aryl, heterocyclyl, or aralkyl. When the nitrogen atom is disubstituted, the two substituents together with the nitrogen atom can form a heterocycle.

Pharmaceutically-Acceptable Salts.

The invention provides the use of pharmaceutically-acceptable salts of any therapeutic compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Purity of Compounds of the Invention.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

Light-Activation of Compounds of the Invention.

Compounds disclosed herein can be effective as efflux pump inhibitors (EPIs). The compounds can inhibit efflux pumps by direct binding. The binding of the efflux pumps by the compounds can prevent expulsion of antibiotics that have been administered for treatment of microbial infections. Compounds of the invention can compete with commonly-used EPIs.

The present disclosure describes compounds that can act as bacterial efflux inhibitors. Non-limiting examples of illustrative compounds can be based on the 2,3-di-((E)-2-arylethenyl)indole structural scaffold.

Inactive 2,3-di-((E)-2-arylethenyl)indoles, which have low bactericidal activity unless used in combination with known antibiotics, can be converted to potent antibacterial agents as single agents via light-activation. Low doses of compounds of the invention irradiated with white light for 2 minutes can kill Gram-positive organisms including, for example, hospital-acquired MRSA, community-acquired MRSA, *Staphylococcus aureus*, vancomycin-resistant *Enterococcus* (VRE), *Streptococcus pyogenes*, and *Streptococcus mutans* (Ward's 85W). Gram-negative bacteria, for example, *Acinetobacter baumannii, Escherichia coli, Klebsiella pneumoniae*, and Carbapenem-resistant enterobacteriaceae, can also be susceptible to treatment with compounds of the invention in the presence of non-toxic doses of PMB. Light-induced killing of bacteria with 2,3-di-((E)-2-arylethenyl)indoles can represent a therapeutic strategy in the treatment of localized infections involving resistant microorganisms.

In some embodiments, compounds of the invention can be photoactive, photosensitive, photodynamic, or photoresponsive. The compound can be used for photodynamic therapy, wherein the compound can be a photo sensitizer and lead to the generation of, for example, singlet oxygen and reactive oxygen species (ROS).

Wavelengths of light that can be used in a method of the invention include, for example, about 200 nm, about 210 nm, about 220 nm, about 230 nm, about 240 nm, about 250 nm, about 260 nm, about 270 nm, about 280 nm, about 290 nm, about 300 nm, about 310 nm, about 320 nm, about 330 nm, about 340 nm, about 350 nm, about 360 nm, about 370 nm, about 380 nm, about 390 nm, about 400 nm, about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550 nm, about 560 nm, about 570 nm, about 580 nm, about 590 nm, about 600 nm, about 610 nm, about 620 nm, about 630 nm, about 640 nm, about 650 nm, about 660 nm, about 670 nm, about 680 nm, about 690 nm, about 700 nm, about 710 nm, about 720 nm, about 730 nm, about 740 nm, about 750 nm, about 760 nm, about 770 nm, about 780 nm, about 790 nm, and about 800 nm.

In some embodiments, compounds of the invention can be applied topically to the skin, or a body cavity, for example, oral, vaginal, bladder, cranial, spinal, thoracic, or pelvic cavity of a subject. In some embodiments, the compounds of the invention can be applied to an accessible body cavity. The compound can be then be activated via exposure of the skin to natural or artificial light. The skin can be exposed to light, for example, for about 1 second, about 2 seconds, about 3 seconds, about 4 seconds, about 5 seconds, about 6 seconds, about 7 seconds, about 8 seconds, about 9 seconds, about 10 seconds, about 15 seconds, about 20 seconds, about 25 seconds, about 30 seconds, about 35 seconds, about 40 seconds, about 45 seconds, about 50 seconds, about 55 seconds, about 1 minute, about 1.5 minutes, about 2 minutes, about 2.5 minutes, about 3 minutes, about 3.5 minutes, about 4 minutes, about 4.5 minutes, about 5 minutes, about 6 minutes, about 7 minutes, about 8 minutes, about 9 minutes, about 10 minutes, about 15 minutes, or about 20 minutes.

The depth of administration of the compounds in the skin can be, for example, about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, about 4.1 mm, about 4.2 mm, about 4.3 mm, about 4.4 mm, about 4.5 mm, about 4.6 mm, about 4.7 mm, about 4.8 mm, about 4.9 mm, and about 5 mm.

Activation of the compound can occur via exposure to light wherein the administration of the light is continuous or pulsed. Pulses of light can be separated by, for example, about 1 second, about 2 seconds, about 3 seconds, about 4 seconds, about 5 seconds, about 6 seconds, about 7 seconds, about 8 seconds, about 9 seconds, about 10 seconds, about 15 seconds, about 20 seconds, about 25 seconds, about 30 seconds, about 35 seconds, about 40 seconds, about 45 seconds, about 50 seconds, about 55 seconds, about 1 minute, about 1.5 minutes, about 2 minutes, about 2.5 minutes, about 3 minutes, about 3.5 minutes, about 4 minutes, about 4.5 minutes, about 5 minutes, about 6 minutes, about 7 minutes, about 8 minutes, about 9 minutes, about 10 minutes, about 15 minutes, or about 20 minutes.

In some embodiments, activation of the compound via light can occur concurrently with, or subsequent to, administration of the compound to a subject. Light can then be administered to the subject, for example, every 1 minute, 2 minutes, 3 minutes, 4 minutes, 5 minutes, 6 minutes, 7 minutes, 8 minutes, 9 minutes, 10 minutes, 15 minutes, 20 minutes, 25 minutes, 30 minutes, 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 18 hours, 1 day, 2 days, 3 days, 4 days, 5 days, 6 days, or 1 week to improve efficacy of the compound.

The energy of light used to activate the compound can be, for example, about 10 $J/cm^2$, about 15 $J/cm^2$, about 20 $J/cm^2$, about 25 $J/cm^2$, about 30 $J/cm^2$, about 35 $J/cm^2$, about 40 $J/cm^2$, about 45 $J/cm^2$, about 50 $J/cm^2$, about 55 $J/cm^2$, about 60 $J/cm^2$, about 65 $J/cm^2$, about 66 $J/cm^2$, about 67 $J/cm^2$, about 68 $J/cm^2$, about 69 $J/cm^2$, about 70 $J/cm^2$, about 71 $J/cm^2$, about 72 $J/cm^2$, about 73 $J/cm^2$, about 74 $J/cm^2$, about 75 $J/cm^2$, about 76 $J/cm^2$, about 77 $J/cm^2$, about 78 $J/cm^2$, about 79 $J/cm^2$, about 80 $J/cm^2$, about 81 $J/cm^2$, about 82 $J/cm^2$, about 83 $J/cm^2$, about 84 $J/cm^2$, about 85 $J/cm^2$, about 86 $J/cm^2$, about 87 $J/cm^2$, about 88 $J/cm^2$, about 89 $J/cm^2$, about 90 $J/cm^2$, about 95 $J/cm^2$, or about 100 $J/cm^2$.

The brightness of light used to activate the compound can be, for example, about 100 lm, about 110 lm, about 120 lm, about 130 lm, about 140 lm, about 150 lm, about 160 lm, about 170 lm, about 180 lm, about 190 lm, about 200 lm, about 250 lm, about 300 lm, about 350 lm, about 450 lm, about 500 lm, about 550 lm, about 600 lm, about 650 lm, about 700 lm, about 750 lm, about 800 lm, about 850 lm, about 900 lm, about 950 lm, about 1000 lm, about 1100 lm, about 1200 lm, about 1300 lm, about 1400 lm, about 1500 lm, about 1600 lm, about 1700 lm, about 1800 lm, about 1900 lm, about 2000 lm, about 2500 lm, about 3000 lm, about 3500 lm, or about 4000 lm.

When exposed to continuous light, compounds of the invention can have an increase in activity that is, for example, about 2-fold, about 3-fold, about 4-fold, about 5-fold, about 6-fold, about 7-fold, about 8-fold, about 9-fold, about 10-fold, about 11-fold, about 12-fold, about 13-fold, about 14-fold, about 15-fold, about 16-fold, about 17-fold, about 18-fold, about 19-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, about 100-fold, about 110-fold, about 120-fold, about 130-fold, about 140-fold, about 150-fold, about 160-fold, about 170-fold, about 180-fold, about 190-fold, about 200-fold, about 250-fold, about 300-fold, about 350-fold, about 400-fold, about 450-fold, about 500-fold, about 550-fold, about 600-fold, about 650-fold, about 700-fold, about 750-fold, about 800-fold, about 850-fold, about 900-fold, about 950-fold, about 1000-fold, about 1500-fold, or about 2000-fold greater than when the compound is not exposed to continuous light.

When exposed to pulsed light, compounds of the invention can have an increase in activity that is, for example, about 2-fold, about 3-fold, about 4-fold, about 5-fold, about 6-fold, about 7-fold, about 8-fold, about 9-fold, about 10-fold, about 11-fold, about 12-fold, about 13-fold, about 14-fold, about 15-fold, about 16-fold, about 17-fold, about 18-fold, about 19-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, about 100-fold, about 110-fold, about 120-fold, about 130-fold, about 140-fold, about 150-fold, about 160-fold, about 170-fold, about 180-fold, about 190-fold, about 200-fold, about 250-fold, about 300-fold, about 350-fold, about 400-fold, about 450-fold, about 500-fold, about 550-fold, about 600-fold, about 650-fold, about 700-fold, about 750-fold, about 800-fold, about 850-fold, about 900-fold, about 950-fold, about 1000-fold, about 1500-fold, or about 2000-fold greater than when the compound is not exposed to constant light.

Bacterial strains that can be treated by a method of the invention can be gram-negative or gram-positive. Non-limiting examples of microbes that can be treated by a method of the invention include *Acinetobacter baumannii*, carbapenem-resistant Enterobacteriaceae (CRE), clindamycin-resistant Group B *Streptococcus, Clostridium difficile*, drug-resistant *Campylobacter*, drug-resistant *Neisseria gonorrhoeae*, drug-resistant non-typhoidal *Salmonella*, drug-resistant *Salmonella Typhi*, drug-resistant *Shigella*, drug-resistant *Streptococcus pneumoniae*, drug-resistant tuberculosis, erythromycin-resistant Group A *Streptococcus, Escherichia coli*, extended spectrum β-lactamase producing Enterobacteriaceae (ESBLs), fluconazole-resistant *Candida*, methicillin-resistant *S. aureus* (MRSA), multidrug-resistant *Acinetobacter*, multidrug-resistant *Pseudomonas aeruginosa, S. aureus*, VRE, and vancomycin-resistant *S. aureus* (VRSA). In some embodiments, the methods of the invention can be applied to agricultural pathogens.

In some embodiments, a therapy of the disclosure has synergistic activity in combination with an antibiotic. Synergy can refer to the observation that the combination of two therapeutic agents can have an overall effect that is greater than the sum of the two individual effects. Synergy can also refer to the observation that a single drug produces no effect but, when administered with a second drug produces an effect that is greater than the effect produced by the second therapeutic agent alone.

Classes of antibiotics that can be used in a method of invention include, for example, aminoglycosides, ansamycins, β-lactams, carbapenems, cephalosporins, glycopeptides, lincosamides, lipopeptides, macrolides, monobactams, nitrofurans, oxazolidinones, penicillins, polypeptides, quinolones, fluroquinolones, sulfonamides, and tetracyclines.

Non-limiting examples of antibiotics that can be used in a method of the invention include ampicillin, amoxicillin, azithromycin, carbenicillin, clarithromycin, dicloxicillin, doxycycline, erythromycin, gentamicin, kanamycin, methicillin, neomycin, norfloxacin, oxacillin, PMB, colisitin, penicillin, penicillin G, penicillin V, streptomycin, tetracycline, tobramycin, polyethyleneimine, lactic acid, benzoic acid bacitracin, imipenem, and vancomycin.

In some embodiments, compounds of the invention can be used to treat a condition caused by a microbe in a subject. In some embodiments, the microbe can be a bacterium, fungus, or protozoa.

In some embodiments, compounds of the invention can be used to treat cancer in a subject. A compound of the invention can, for example, slow the proliferation of cancer cell lines, or kill cancer cells. Non-limiting examples of cancer that can be treated by a compound of the invention include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyo sarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

Subjects can be, for example, elderly adults, adults, adolescents, pre-adolescents, children, toddlers, infants, and non-human animals. In some embodiments, a subject is a patient. Non-human animal subjects can be, for example, a mouse, rat, a chicken, a rabbit, a dog, a cat, or a cow. Compounds of the invention can be employed in places where the spread of drug-resistant bacteria can be more likely, for example, hospitals, nursing homes, dormitories, homeless shelters, military barracks, schools, locker rooms, gymnasiums, and prisons. The methods of the invention can be applied to, for example, fomites, surgical instruments, tables, chairs, doors, eating utensils, bedding, beds, and keyboards.

In some embodiments, the methods of the invention can be applied to, for example, a plant, a fungus, or a parasite. Administration can, for example, kill or inhibit the Plant, fungus, or parasite, or kill or inhibit an agent that harms or presents a risk of harm to a plant or fungus, or lessen a likelihood of such risk. For example, agricultural applications to inhibit the spread of and damage by agriculturally-detrimental microbes are possible.

Pharmaceutical Compositions of the Invention.

A pharmaceutical composition of the invention can be used, for example, before, during, or after treatment of a subject with light, antibiotics, or another pharmaceutical agent.

A pharmaceutical composition of the invention can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration.

A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining the active compounds with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N,N'-bis(2-ethanesulfonic acid) buffer (PIPES), and saline sodium citrate buffer (SSC). Non-limiting examples of co-solvents used in an oral dissolvable formulation can include sucrose, urea, cremaphor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, can be melted.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include liquid, powder, gel, nanosuspension, nanoparticle, microgel, aqueous or oily suspensions, emulsion, and any combination thereof.

Non-limiting examples of pharmaceutically-acceptable excipients suitable for use in the invention include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Multiple therapeutic agents can be administered in any order or simultaneously. In some embodiments, a compound of the invention is administered in combination with, before, or after an antibiotic. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A therapeutic agent can be administered as soon as is practicable after the onset of a disease or condition is detected or suspected, and for a length of time necessary for the treatment of the disease, such as, for example, from about 1 month to about 3 months. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anticholinergics/antispasmotics, antidiabetic agents, antihypertensive agents, antineoplastics, cardiovascular agents, central nervous system agents, coagulation modifiers, hormones, immunologic agents, immunosuppressive agents, and ophthalmic preparations.

Compounds can be delivered via liposomal technology. The use of liposomes as drug carriers can increase the therapeutic index of the compounds. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Dosing.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a dose can be expressed in terms of an amount of the drug divided by the mass of the subject, for example, milligrams of drug per kilograms of subject body mass. In some embodiments, a compound is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg.

EXAMPLES

Example 1: Synthesis of
2,3-di-((E)-2-arylethenyl)indoles 2,3-di-((E)-2-Arylethenyl)indoles (compounds 1-6) were prepared using oxidative Heck coupling as detailed in Scheme 1.

Scheme 1

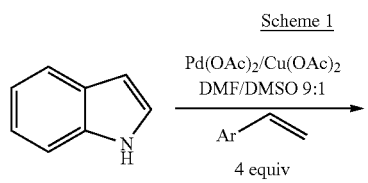

Palladium acetate (0.1 eq) was added to a mixture of a selected styrene (4 eq), copper (II) acetate (4 eq), and indole (1 eq) in DMF/DMSO (9:1). The reaction mixture was stirred at 70-80° C. for 18-24 hours with thin-layer chromatography (TLC) monitoring of the reaction progress (20% EtOAc/hexanes). The reaction was cooled to room temperature and partitioned between minimal amounts of water and EtOAc, which was filtered through a plug of celite. The layers were then separated and the organic layer was washed with saturated brine solution, dried over $MgSO_4$, filtered, and concentrated under reduced pressure. Flash chromatography afforded the desired 2,3-di-((E)-2-arylethenyl)indoles as depicted below:

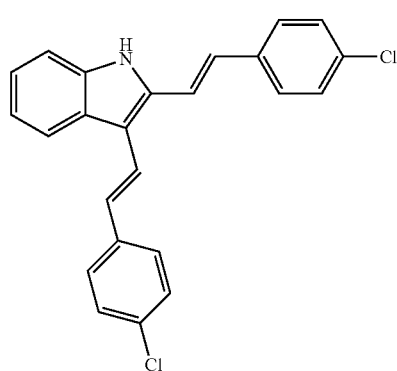

Yield 41%; $^1$H NMR (400 MHz, DMSO-$d_6$) δ 11.60 (s, 1H), 8.09 (d, J=8.0 Hz, 1H), 7.80 (ddd, J=16.5, 7.8, 4.6 Hz, 6H), 7.49 (d, J=8.3 Hz, 2H), 7.42 (dd, J=8.3, 6.6 Hz, 3H), 7.31-7.19 (m, 3H), 7.13 (t, J=7.5 Hz, 1H); $^{13}$C NMR (100 MHz, DMSO-$d_6$) δ: 138.9, 138.8, 137.1, 136.7, 133.6, 132.3, 129.7, 129.4, 129.0, 128.3, 127.7, 127.3, 125.9, 124.4, 123.0, 121.7, 121.3, 118.2, 115.4, 112.1; HRMS calculated for $C_{24}H_{18}Cl_2N$ (M+H)$^+$: 390.0816, actual HRMS 390.0787.

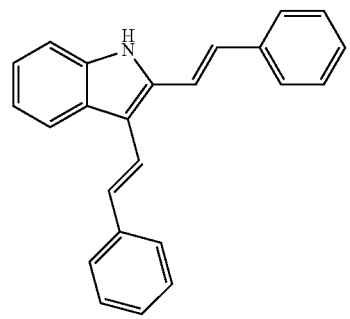

Yield 60%; $^1$H NMR (400 MHz, DMSO-$d_6$) δ 11.56 (s, 1H), 8.07 (d, J=8.6 Hz, 1H), 7.77 (q, J=10.6 Hz, 7H), 7.48-7.18 (m, 14H), 7.12 (s, 1H); $^{13}$C NMR (100 MHz, DMSO-$d_6$) δ: 139.0, 138.1, 137.4, 136.4, 129.2, 128.9, 128.8, 128.2, 127.1, 126.9, 126.4, 126.1, 125.8, 123.6, 121.8, 121.2, 120.5, 117.0, 113.9, 111.6; HRMS calculated for $C_{24}H_{20}N$ (M+H)$^+$: 322.1596, actual HRMS 322.1606.

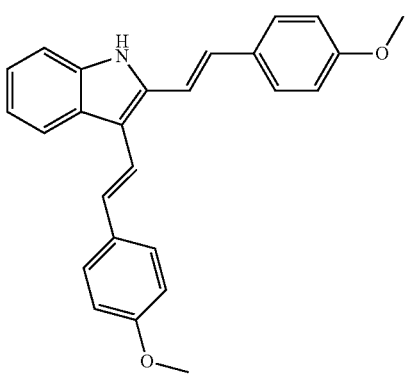

Yield 66%; $^1$H NMR (400 MHz, DMSO-$d_6$) δ 10.57 (s, 1H), 8.25-7.83 (m, 1H), 7.83-6.69 (m, 7H), 4.20-2.48 (m, 6H); $^{13}$C NMR (100 MHz, DMSO-$d_6$) δ: 158.8, 158.6, 131.6, 127.8, 127.6, 127.0, 126.6, 125.8, 124.6, 124.4, 123.9, 122.9, 121.8, 120.5, 120.2, 119.8, 119.6, 119.2, 114.1, 113.9, 111.6, 111.6, 54.6; HRMS calculated for $C_{26}H_{24}NO_2$ (M+H)$^+$: 382.1807, actual HRMS 382.1800.

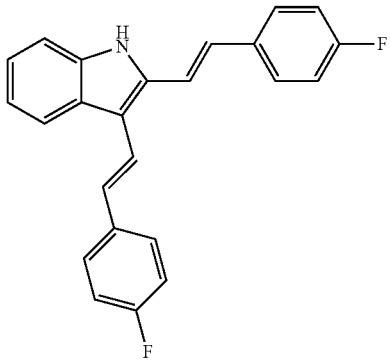

Yield 49%; $^1$H NMR (400 MHz, DMSO-$d_6$) δ 10.68 (s, 1H), 8.09 (d, J=7.9 Hz, 1H), 7.81 7.69 (m, 6H), 7.46-7.39

(m, 1H), 7.37-7.10 (m, 8H); $^{13}$C NMR (100 MHz, DMSO-d$_6$) δ: 137.7, 135.5, 135.4, 133.8, 128.4, 128.3, 127.5, 127.5, 126.8, 125.0, 123.3, 121.2, 121.1, 120.7, 120.2, 116.4, 115.6, 115.4, 115.3, 115.0, 111.1, 111.0; HRMS calculated for C$_{24}$H$_{18}$F$_2$N (M+H)$^+$: 358.1407, actual HRMS 358.1407.

5

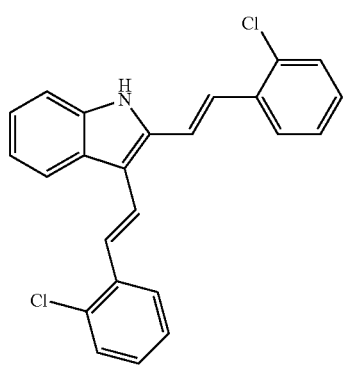

Yield 40%; $^1$H NMR (400 MHz, DMSO-d$_6$) δ 11.07 (s, 1H), 8.07 (q, J=8.9, 8.4 Hz, 3H), 7.87 (td, J=15.7, 2.1 Hz, 2H), 7.72-7.58 (m, 2H), 7.51-7.18 (m, 10H); $^{13}$C NMR (100 MHz, DMSO-d$_6$) δ: 137.1, 136.5, 134.7, 134.6, 133.3, 133.0, 130.0, 129.8, 128.8, 127.8, 127.1, 126.9, 126.7, 126.2, 125.8, 124.3, 124.2, 123.5, 122.7, 121.1, 120.8, 120.2, 118.6, 115.7, 110.9; HRMS calculated for C$_{24}$H$_{18}$Cl$_2$N (M+H)$^+$: 390.0816, actual HRMS 390.0815.

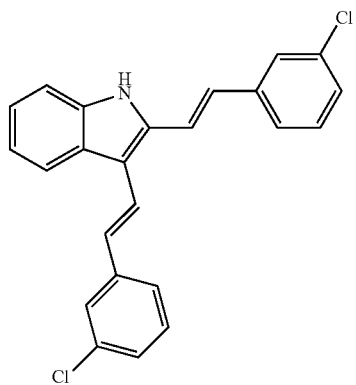
6

Yield 40%; $^1$H NMR (400 MHz, acetone-d$_6$) δ 10.79 (s, 1H), 8.14 (dd, J=7.9, 3.2 Hz, 1H), 7.99-7.87 (m, 2H), 7.76 (dd, J=13.1, 2.6 Hz, 2H), 7.69-7.55 (m, $^{3H}$), 7.48-7.14 (m, 11H); $^{13}$C NMR (100 MHz, acetone-d$_6$) δ: 135.8, 134.2, 134.1, 130.3, 130.0, 127.3, 126.7, 126.1, 125.8, 125.4, 125.3, 124.9, 124.5, 123.6, 122.8, 120.9, 120.4, 118.0, 114.6, 111.2; HRMS calculated for C$_{24}$H$_{18}$Cl$_2$N (M+H)$^+$: 390.0816, actual HRMS 390.0807.

7

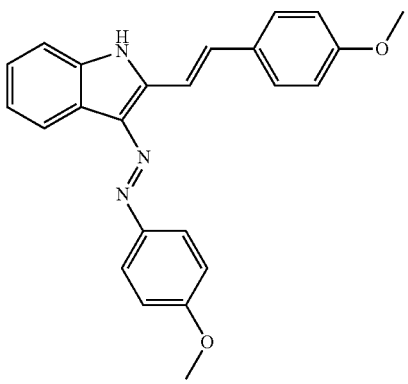

$^1$H NMR (400 MHz, acetone-d$_6$) δ 11.09 (s, 1H), 8.66-8.64 (d, J=7.28 Hz, 1H), 8.22-8.20 (d, J=8.0 Hz, 2H), 7.91-7.90 (d, J=7.28 Hz, 2H), 7.50-7.48 (d, J=6.8 Hz, 1H), 7.28-7.08 (m, 5H); $^{13}$C NMR (100 MHz, acetone-d$_6$) δ: 161.5, 161.3, 149.6, 142.3, 137.0, 132.4, 131.6, 124.7, 124.6, 124.1, 124.0, 123.3, 121.0, 115.1, 115.0, 112.1. HRMS calculated for C$_{22}$H$_{20}$N$_3$O$_2$ (M+H)$^+$: 358.1556, actual HRMS 358.1556.

8

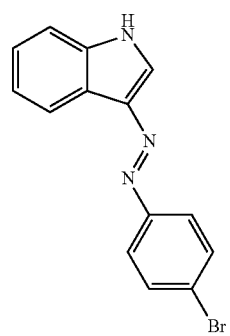

$^1$H NMR (400 MHz, acetone-d$_6$) δ 11.20 (s, 1H), 8.53-8.51 (d, J=6.60 Hz, 1H), 8.31 (s, 1H), 7.84-7.70 (m, 4H), 7.56-7.54 (d, J=7.24 Hz, 1H), 7.31-7.30 (m, 2H); $^{13}$C NMR (100 MHz, acetone-d$_6$) δ: 152.9, 137.1, 136.4, 133.4, 132.1, 124.1, 123.3, 122.7, 121.9, 118.6, 112.0. HRMS calculated for C$_{14}$H$_{11}$BrN$_3$(M+H)$^+$: 300.0136, actual HRMS 300.0135.

9

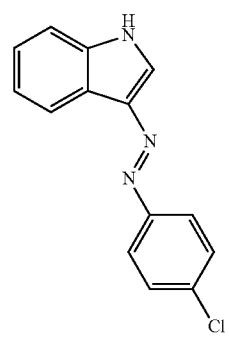

$^1$H NMR (400 MHz, acetone-d$_6$) δ 11.17 (s, 1H), 8.54-8.52 (d, J=7.6 Hz, 1H), 8.30 (s, 1H), 7.91-7.89 (d, J=8.64

Hz, 1H), 7.56-7.54 (m, 3H), 7.34-7.27 (m, 2H); $^{13}$C NMR (100 MHz, acetone-d$_6$) δ: 153.5, 138.0, 137.3, 134.6, 134.2, 130.0, 125.0, 123.9, 123.6, 123.5, 119.6, 112.9. HRMS calculated for C$_{14}$H$_{11}$ClN$_3$(M+H)$^+$: 256.0642, actual HRMS 256.0642.

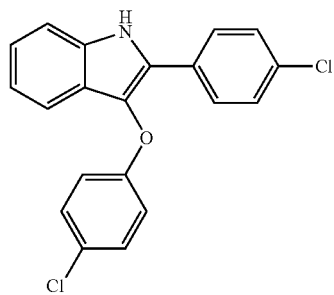

$^1$H NMR (400 MHz, acetone-d$_6$) δ 10.66 (s, 1H), 7.92-7.90 (d, J=8.52 Hz, 2H), m, 1H), 7.49-6.85 (m, 10H); $^{13}$C NMR (100 MHz, acetone-d$_6$) δ: 157.4, 132.6, 129.7, 129.6, 129.5, 129.3, 129.2, 129.0, 127.3, 127.2, 126.5, 123.6, 123.2, 121.5, 119.9, 117.5, 117.2, 117.1, 116.8, 111.9. HRMS calculated for C$_{20}$H$_{14}$Cl$_2$NO (M+H)$^+$: 354.0452, actual HRMS 354.0459.

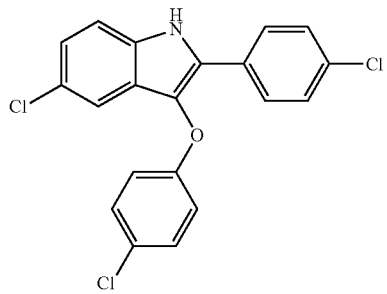

$^1$H NMR (400 MHz, acetone-d$_6$) δ 10.85 (s, 1H), 7.91-7.89 (d, J=7.8 Hz, 2H), m, 1H), 7.50-7.05 (m, 9H); $^{13}$C NMR (100 MHz, acetone-d$_6$) δ: 158.0, 134.0, 133.6, 130.8, 130.5, 130.1, 130.0, 128.3, 127.8, 127.7, 126.1, 124.2, 123.4, 118.0, 117.5, 114.4. HRMS calculated for C$_{20}$H$_{13}$Cl$_3$NO (M+H)$^+$: 388.0063, actual HRMS 388.0067.

Non-limiting examples of compounds of the invention include the following:

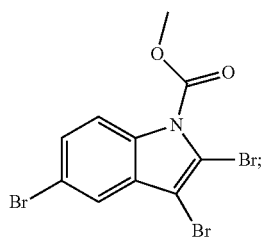

12

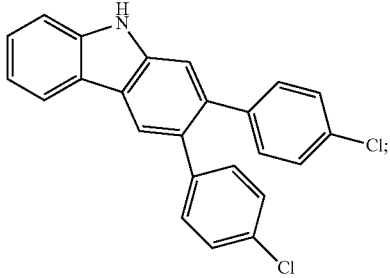

13

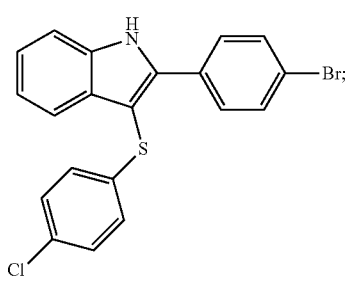

14

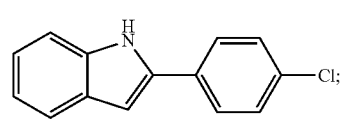

15

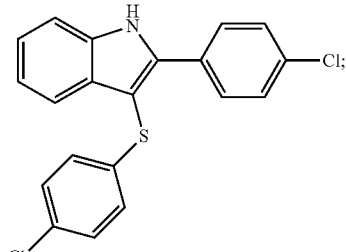

16

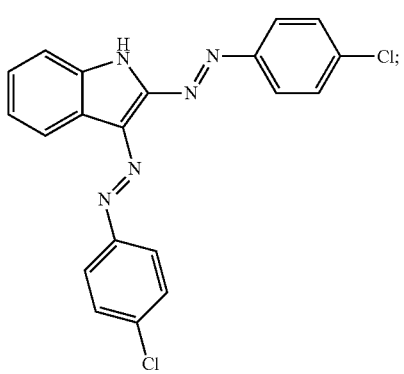

17

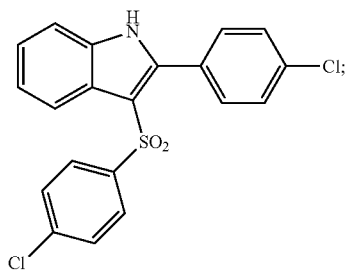

18

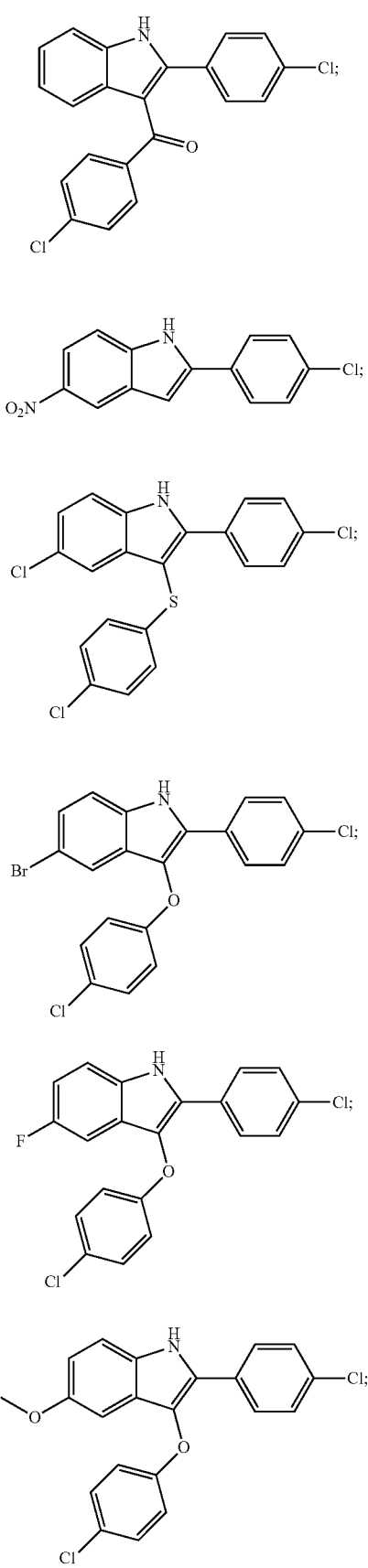
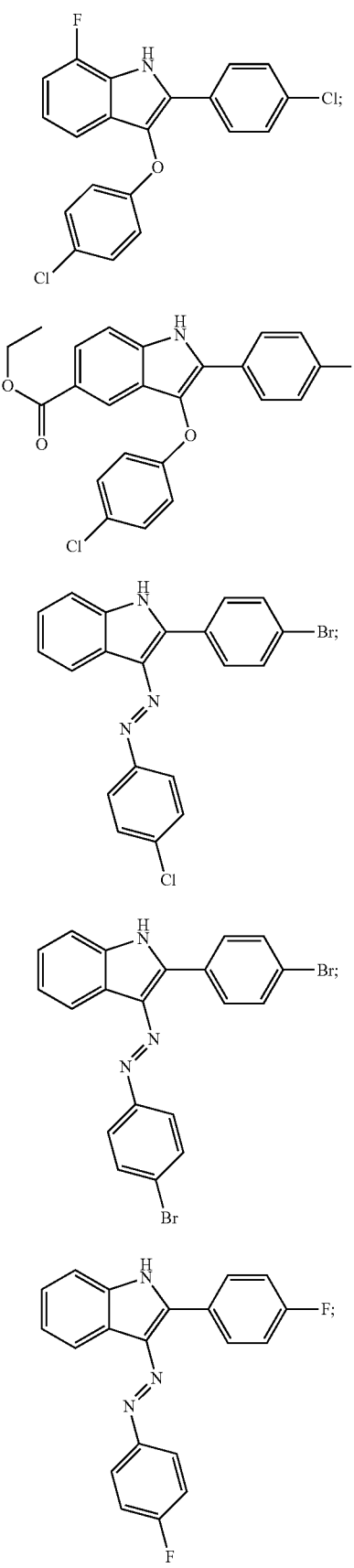

-continued

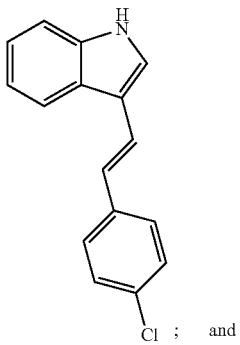

and

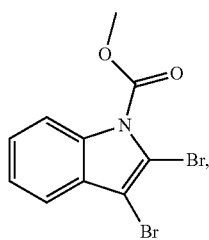

and pharmaceutically-acceptable salts thereof.

Example 2: Toxicity of Compounds of the Invention on HeLa and WI38 Cells

The toxicities of the compounds of the invention were determined for human cancerous cervical epithelium HeLa and normal lung fibroblast WI38 cells. The toxicities of EPIs INF-55 and INF-55Cl were quantified as controls.

TABLE 1 shows the measured toxicities ($IC_{50}$; μM) of the compounds of the invention and the EPIs INF-55 and INF-55Cl against HeLa cells. TABLE 2 compares the toxicity of compounds 7-11 on HeLa cells and normal WI38 cells. The results indicated that compounds 7, 9, and 10 killed cancerous HeLa cells at concentrations that were not toxic to normal WI38 cells in culture.

TABLE 1

| Compound | $IC_{50}$ HeLa | Compound | $IC_{50}$ HeLa |
|---|---|---|---|
| 1 | 68.9 ± 4.8 | 20 | Non-Toxic |
| 7 | 38.55 +/− 2.52 | 21 | 8.2 ± 1.0 |
| 8 | 31.56 +/− 1.74 | 22 | 3.2 ± 0.4 |
| 9 | 34.37 +/− 0.85 | 23 | 12.9 ± 3.2 |
| 10 | 36.82 +/− 1.53 | 24 | 23.9 ± 1.8 |
| 11 | 25.85 +/− 2.47 | 25 | 13 ± 3.5 |
| 13 | 16.4 ± 1.1 | 26 | 18.6 ± 1.1 |
| 14 | 12.2 ± 1.6 | 27 | 12.5 ± 0.2 |
| 15 | Non-Toxic | 28 | 8.6 ± 1.4 |
| 16 | 6.4 ± 1.0 | 29 | 11.6 ± 0.7 |
| 18 | 14.3 ± 0.7 | 30 | 34.4 ± 5.0 |
| 19 | 35.8 ± 6 | 31 | Non-Toxic |
| INF-55 | Non-Toxic | INF-55Cl | Non-Toxic |

TABLE 2

| Compound | $IC_{50}$ "cancer" HeLa (μM) | $IC_{50}$ "normal" WI38 (μM) |
|---|---|---|
| 7 | 38.55 +/− 2.52 | 53.03 +/− 9.84 |
| 8 | 31.56 +/− 1.74 | 11.67 +/− 0.82 |
| 9 | 34.37 +/− 0.85 | 61.89 +/− 6.63 |
| 10 | 36.82 +/− 1.53 | 54.81 +/− 12.99 |
| 11 | 25.85 +/− 2.47 | 9.62 +/− 0.24 |

Example 3: Minimum Inhibitory Concentrations (MICs) of Compounds of the Invention and Antibiotics Against MRSA Isolates The MICs of *S. aureus* ATCC 33591, BAA-44, BAA-1707, BAA-1717, BAA-1720, BAA-1747, BAA-1754, BAA-1761, BAA-1763, BAA-1764, and BAA-1766 were measured using a cell concentration of about $5 \times 10^5$ colony forming units (CFU)/mL. In a 96-well microtiter plate, two-fold dilutions were made of each drug (starting with 100 μM) in 100 μL of a cell suspension in trypticase soy broth (TSB). The samples were incubated overnight at 37° C. on a rotary shaking incubator set at 100 revolutions per minute (rpm) and were visually inspected for turbidity. A 20% well-volume of 3-(4,5-dimethylthiazol-2-yl)-2,5-diphenyltetrazolium bromide (MTT reagent, 5 mg/mL) was added, and the samples were incubated for about 20 minutes. The MICs were determined as the lowest concentration at which full visual inhibition was observed by the unaided eye.

TABLE 3 shows the MICs of compound 1 and compounds 7-9 against various MRSA isolates. TABLE 4 shows the MICs of antibiotics, including oxacillin, norfloxacin, tetracycline, gentamycin, vancomycin, erythromycin, and penicillin, against various MRSA isolates. The results in TABLE 4 indicated that several of the MRSA isolates developed resistance against the antibiotics, which are indicated with *.

TABLE 3

| MRSA Isolate (ATCC) | 1 (μM) | 7 (μM) | 8 (μM) | 9 (μM) | 10 (μM) | 11 (μM) |
|---|---|---|---|---|---|---|
| 33591 | TBD | 50-100 | 3.1-6.3 | 12.5 | 12.5 | 6.3-12.5 |
| BAA-44 | 400 | 100 | 15 | 16 | 8 | 4 |
| BAA-1707 | TBD | 6.3-12.5 | 6.3 | 12.5 | 12.5 | 12.5 |
| BAA-1717 | TBD | 12.5 | 6.3 | 6.3-12.5 | 6.3 | 3.1-6.3 |
| BAA-1720 | TBD | 12.5-25 | 6.3 | 12.5 | 6.3 | 3.1-6.3 |
| BAA-1747 | TBD | 50-100 | 6.3 | 12.5 | 12.5-25 | 6.3-12.5 |
| BAA-1754 | TBD | >100 | 12.5 | 12.5 | 50 | 50-100 |
| BAA-1761 | TBD | 50 | 12.5 | 12.5 | >100 | 50-100 |
| BAA-1763 | TBD | >100 | 6.3 | 12.5 | 50-100 | 50 |
| BAA-1764 | TBD | >100 | 12.5 | 12.5 | >100 | 50 |
| BAA-1766 | TBD | >100 | 12.5 | 12.5 | 25-50 | 50-100 |

TABLE 4

| MRSA Isolate (ATCC) | Oxacillin (µg/mL) | Norfloxacin (µg/mL) | Tetracycline (µg/mL) | Gentamycin (µg/mL) | Vancomycin (µg/mL) | Erythromycin (µg/mL) | Penicillin (mg/mL) |
|---|---|---|---|---|---|---|---|
| 33591 | >100* | 25* | 100* | >100* | <3.1 | TBD | TBD |
| BAA-44 | 400* | 100* | 3.1 | >200* | 3.1 | >1000* | 1.6* |
| BAA-1707 | <3.1 | <3.1 | 25* | <3.1 | <3.1 | TBD | TBD |
| BAA-1717 | 200* | TBD | <1.6 | 3.1 | <1.6 | 30* | 1* |
| BAA-1720 | >100* | >100* | <3.1 | <3.1 | <3.1 | TBD | TBD |
| BAA-1747 | 6.3 | 6.3 | <3.1 | 6.3 | <3.1 | TBD | TBD |
| BAA-1754 | 50* | <3.1 | <3.1 | <3.1 | <3.1 | TBD | TBD |
| BAA-1761 | 6.3 | >100* | 12.5 | <3.1 | <3.1 | TBD | TBD |
| BAA-1763 | 50* | >100* | <3.1 | 3-6 | <3.1 | TBD | TBD |
| BAA-1764 | 25* | <3.1 | <3.1 | <3.1 | <3.1 | TBD | TBD |
| BAA-1766 | <6.3 | <3.1 | <3.1 | 12.5* | <3.1 | TBD | TBD |

*indicates development of resistance

Example 4: Fluorescent Competition Assay with Compound 1 with MRSA and *S. aureus*

A fluorescent binding assay was performed to demonstrate that MRSA has more binding sites for compound 1 than *S. aureus* due to the overexpression of NorA efflux pumps in MRSA (FIG. 1). The error bars represent data from three independent measurements.

*S. aureus* and MRSA cells (about $10^8$ CFU/mL) were treated with two doses of compound 1 (1 µM and 10 µM), and the cells were incubated at 37° C. for 15 minutes on a rotary shaker set at 150 rpm. After the incubation, the cells were transferred to a 96-well fluorescent plate reader and read every minute for 30 minutes at excitation wavelengths of 334 nm, 380 nm, and 407 nm, and an emission wavelength of 508 nm. The controls were: 1×PBS, compound 1 (1 µM and 10 µM) in 1×PBS, *S. aureus* in 1×PBS, and MRSA in 1×PBS.

The results in FIG. 1 indicated that MRSA was able to bind more of compound 1, as shown by the overall higher level of fluorescence when compared to the binding of compound 1 by *S. aureus*.

Example 5: Fluorescent Binding Assay of Compound 1 Versus INF-55 and Reserpine

INF-55 and reserpine, NorA EPIs, were used to compete with compound 1 for binding sites on MRSA. Since compound 1 is highly fluorescent, binding could be assessed by measuring the fluorescence at excitation wavelengths of 345 nm, 380 nm, 407 nm, and an emission wavelength of 508 nm. Fluorescent readings were taken every minute for 30 minutes at a lamp energy of 20,000 CW. MRSA cells (about $10^8$ CFU/mL) were pelleted at 7500 rpm and resuspended in 1×PBS. The MRSA cells were then pretreated with the appropriate EPI at varying concentrations and incubated for 30 minutes at 37° C. at 150 rpm on a rotary shaker.

INF-55 (FIG. 2) and reserpine (FIG. 3) were added at 1 µM, 10 µM, 50 µM, and 100 µM. After incubation with the appropriate EPI, compound 1 was added at 5 µM and the samples were incubated for 10 minutes. The samples were then placed in a fluorescent plate reader for analysis. The controls used were as follows: 1×PBS, compound 1 (5 µM) in 1×PBS, each respective concentration of the EPI in 1×PBS, compound 1 (5 µM) added to MRSA cells, and each respective EPI added to MRSA cells. The instrument baseline fluorescence drift was corrected by subtracting the fluorescence measured at each time point for the 1×PBS control sample. The error bars represent data from three independent measurements.

Figure 2:
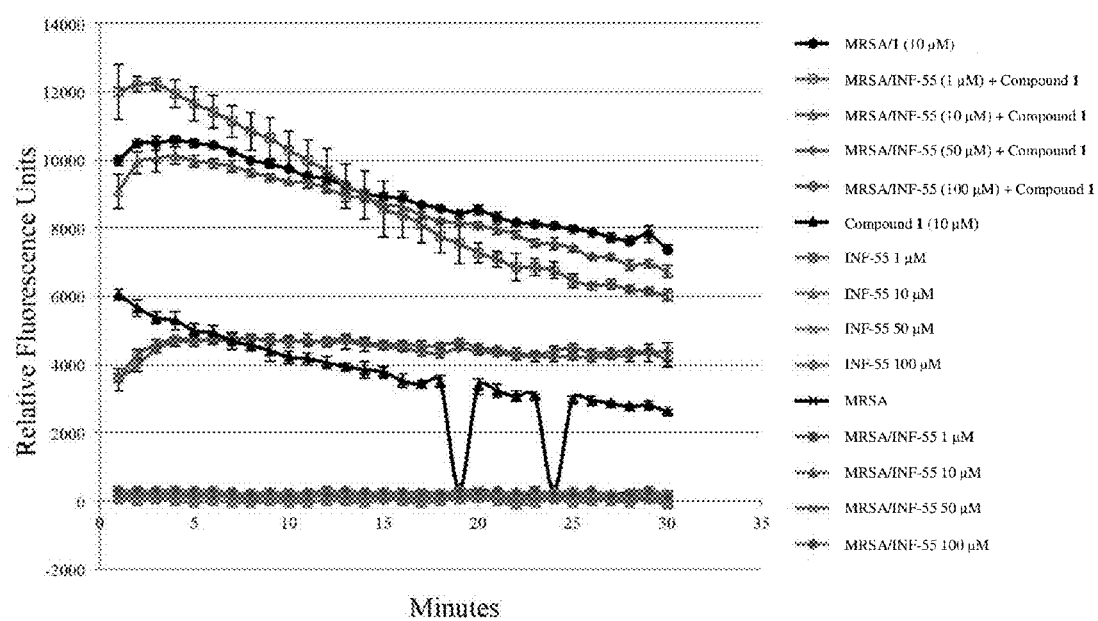
FIG. 2 shows a competition assay between compound 1 and INF-55.

The results from FIG. 2 indicated that compound 1 was able to compete with INF-55 for binding to the efflux pumps of MRSA, as shown by the fluorescence of compound 1.

Figure 3:
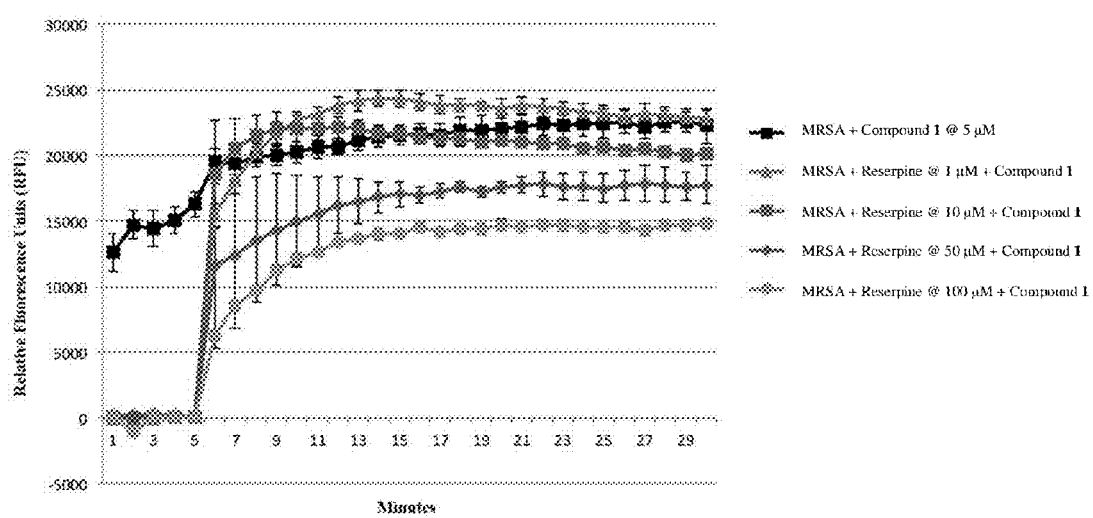
FIG. 3 shows a competition assay between compound 1 and reserpine.

The results from FIG. 3 indicated that compound 1 was able to compete with reserpine for binding to the efflux pumps of MRSA, as shown by the fluorescence of compound 1.

Example 6: Light-Activated Killing of Bacteria Using Compounds of the Invention Using Photodynamic Therapy Some compounds herein exhibited antibacterial activity upon exposure to light and showed toxicity to a large number drug-resistant bacterial species. Photodynamic therapy (PDT) with compound 1 reduced 100,000,000 viable MRSA cells to 0 viability upon receiving 2 minutes of white light irradiation. The compounds of the invention were effective at killing a wide variety of human, animal and agricultural pathogens, including CRE (gut, urinary tract and wound infections), *S. pyogenes* (flesh-eating bacteria), *S. mutans* (dental caries), *Clavibacter* (a major agricultural pathogen), and antibiotic-sensitive organisms. Gram-negative bacteria (e.g., *A. baumannii*) were sensitized to these PDT actions using non-toxic concentrations of PMB.

Bacterial media was inoculated with bacteria and incubated overnight. The bacterial cultures were diluted to $5\times10^8$ CFU/mL using a McFarland latex turbidity standard (0.5). Compound 1 was diluted with sterile DMSO, which was added to the cell suspension in a glass culture tube. The cells were then incubated for 30 minutes at 37° C. on a rotary shaking incubator at 150 rpm. 500 µL of the treated cell suspension was added to a well on a sterile ceramic drop plate. Non-coherent white light from a Lumacare™ LC-122 unit was used to irradiate the samples. The end of the light probe was placed 3 cm above the sample well, perpendicular to the surface of the sample, and light was applied for 2 minutes (15 seconds light, 15 seconds dark). 200 µL of the irradiated sample was transferred to a 96-well plastic microtiter plate, and five ten-fold dilutions were made in the media. 10 µL of each dilution was dripped onto an agar media plate and streaked down the plate by tilting the plate down. The agar plates were incubated at 37° C. overnight, and colony counts were performed to calculate the CFU/mL.

Figure 4:
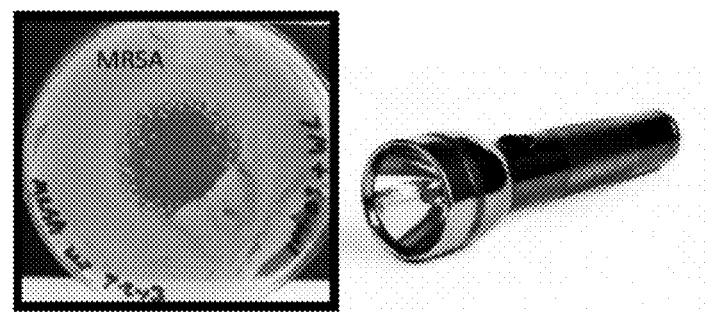
FIG. 4 shows an image of a culture dish (left) and a scanning electron microscope image (right) of MRSA upon receiving photodynamic therapy using a hand-held UV flashlight.
Figure 4:
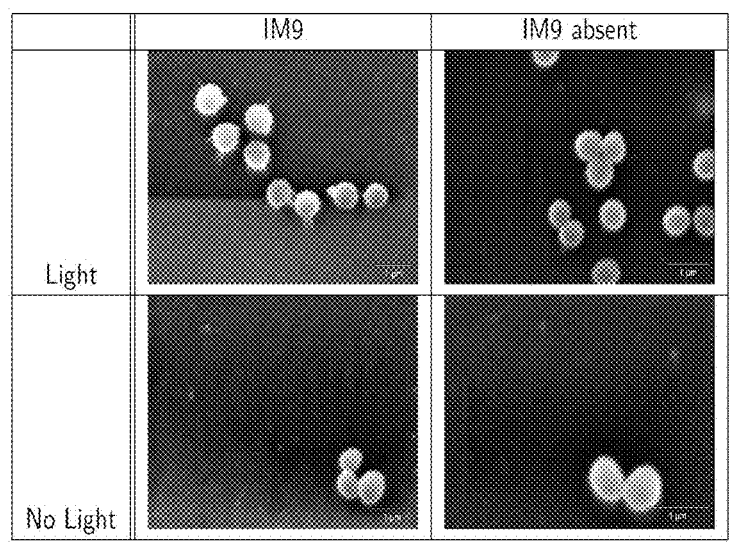

FIG. 4 depicts the effects of PDT on MRSA using a hand-held flashlight, which can either be UV or plain white-light emitted using a LumaCare™ instrument, a hand-held white-light emitting flashlight, or a hand-held Chauvet® LED mini strobe light. The image on the left shows the PDT-stimulated clearance of MRSA, and the image on the right shows a scanning electron microscope image of cells upon being treated with a compound of the invention and receiving PDT. The SEM image shows that while cells treated with the combination of compound 9 at 25 uM and light using a LumaCare™ instrument appear to have burst from the inside. The cells treated with either light or compound 9 alone were undamaged.

Example 7: Light-Activated Killing of Gram-Positive Organisms with Compound 1

Figure 5:
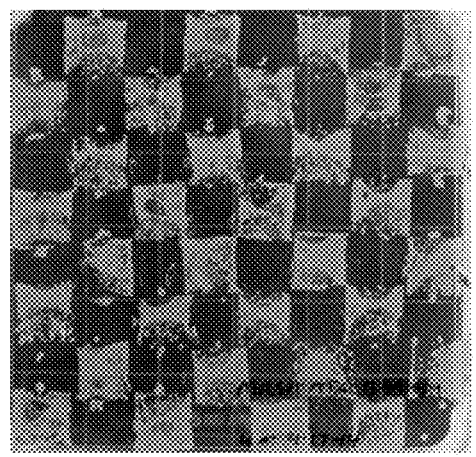
FIG. 5 depicts a chessboard bacterial patterning system for visualization of bacterial growth.

Bacterial patterning is a visually illustrative approach used to demonstrate control of bacterial growth with light and a photo-activated compound. To determine the light-activated killing of Gram-positive bacteria using light and compound 1, an agar plate was prepared containing 20 µM of inactive and non-irradiated compound 1. 20 µM of compound 1 was used to prevent the inhibition of bacterial growth because the 20 µM concentration was significantly lower than the MIC value (400 µM). A chessboard mask was then placed on top of the agar plate. The agar plate was then irradiated with white light to photo-activate compound 1 only in the exposed areas (dark squares of FIG. 5), which caused inhibition of bacterial growth in the illuminated parts of the agar plate, where compound 1 was photoactivated. The agar plate was then inoculated with bacteria and incubated overnight at 37° C. Bacterial colonies were observed only where the area of the plate was covered to prevent irradiation as seen in FIG. 5.

Dose-dependent effects of treating bacteria with compound 1 and irradiation with white light were assessed by treating $10^8$ CFU/mL of cells with compound 1, followed by irradiation with white light for 2 minutes. Compound 1 was added at a specific concentration to 1 mL of a $10^8$ CFU/mL suspension of the respective bacterial cells, and the cells were incubated at 37° C. for approximately 45 minutes on a rotary shaker at 150 rpm. 0.5 mL of the cell suspension was removed and placed into the wells of a sterile ceramic drop plate, and then the cells were irradiated with white light from a Lumacare™ LC 122A light source for 2 minutes at a distance of approximately 3 cm. The time and distance of the light application delivered about 85 J/cm² of 400-700 nm light to the sample. After being irradiated, ten-fold dilutions were made of each cell sample. The dilutions were drip-streaked onto a tryptic soy agar (TSA) plate and incubated at 37° C. for 18-24 hours. Enumeration of bacteria was determined from the dilution, which produced a drip-streak containing approximately 30-300 colonies. After counting the colonies, the CFU/mL was calculated by applying the respective dilution factor and a factor of 100 to account for the 10 µL of sample taken. Appropriate controls were prepared, including cells with no treatment, cells with only compound 1 added, and cells only treated with light.

Figure 6:
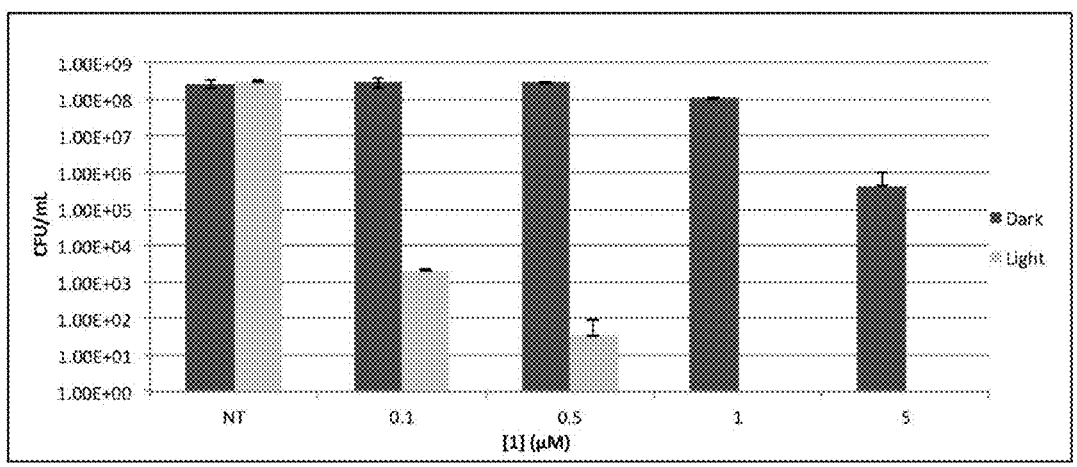
FIG. 6 depicts light-activated killing of hospital-acquired MRSA with compound 1.

TABLE 5 and FIG. 6 show the light-activated killing of MRSA (ATCC No. BAA-44; hospital-acquired MRSA). The error bars in FIG. 6 represent the variations between three replicate determinations. The results indicated that treatment with light led to greater cell toxicity than treatment of the cells with compound 1 alone.

TABLE 5

| Treatment | 1 - Dark Toxicity (CFU/mL) | 1 - Light Toxicity (CFU/mL) |
| --- | --- | --- |
| No treatment | $2.67 \times 10^8 \pm 6.76 \times 10^7$ | $2.94 \times 10^8 \pm 4.08 \times 10^7$ |
| 0.1 µM | $2.85 \times 10^8 \pm 8.05 \times 10^7$ | $2.00 \times 10^3 \pm 4.00 \times 10^2$ |

TABLE 5-continued

| Treatment | 1 - Dark Toxicity (CFU/mL) | 1 - Light Toxicity (CFU/mL) |
| --- | --- | --- |
| 0.5 µM | $2.93 \times 10^8 \pm 2.14 \times 10^7$ | $3.33 \times 10^1 \pm 5.77 \times 10^1$ |
| 1.0 µM | $1.05 \times 10^8 \pm 9.07 \times 10^6$ | None detected (<100 CFU/mL) |
| 5.1 µM | $4.34 \times 10^5 \pm 5.04 \times 10^5$ | None detected (<100 CFU/mL) |

Figure 7:
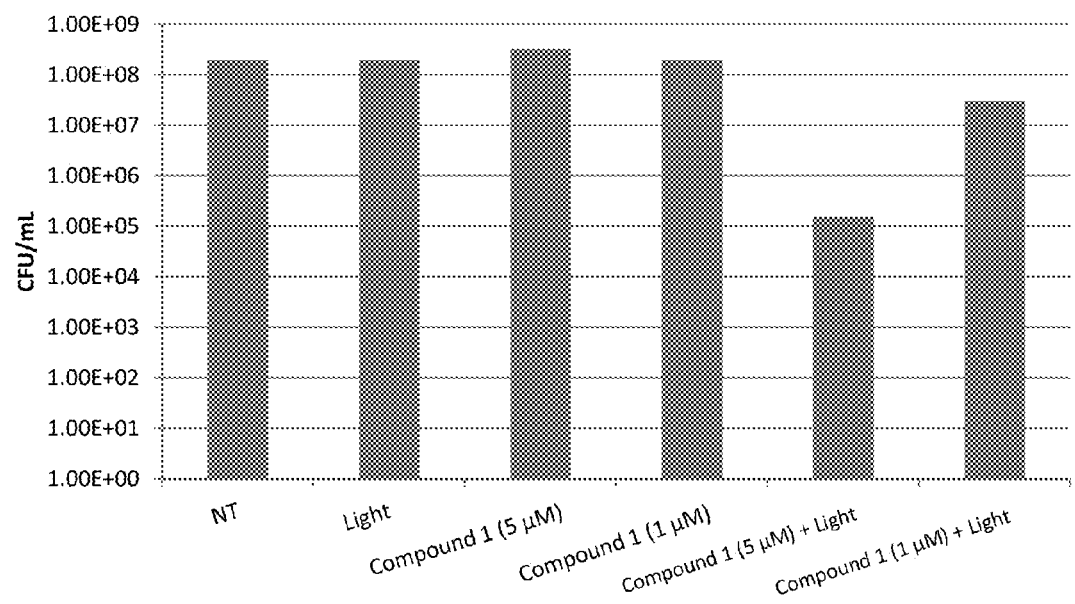
FIG. 7 depicts light-activated killing of hospital-acquired MRSA with compound 1.

FIG. 7 also shows the light-activated killing of MRSA. The results show that there was a 3-log reduction in the concentration of CFUs when the cells were treated with 5 µM of compound 1, and there was a 1-log reduction in the concentration of CFUs when the cells were treated with 1 µM of compound 1.

Figure 8:
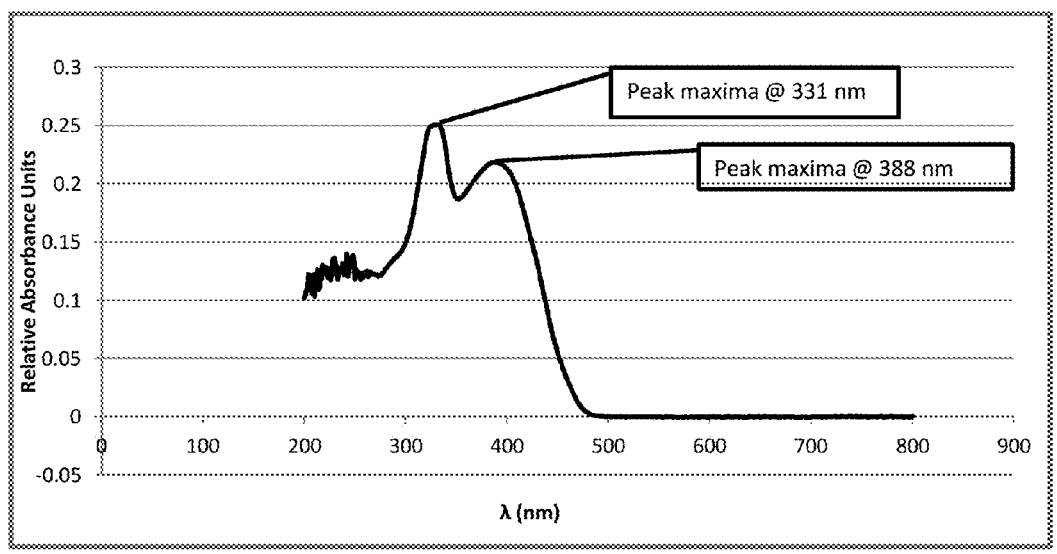
FIG. 8 depicts a UV/Vis spectrum of compound 1.

FIG. 8 shows the UV/Vis spectrum of compound 1. The results show that compound 1 had a primary peak maximum at 331 nm and a secondary peak maximum at 388 nm. These peaks are characteristic of and dependent on the specific structure of compound 1. Since the toxicity of compound 1 could be activated by white light alone (illustrated in FIG. 4), PDT activation was not confined to the compound's absorbance maxima.

TABLE 6 shows the synergy and photodynamic inactivation resulting from treatment with compounds 1, 10, and 11. The results show that compounds 1, 10, and 11 were more effective at killing cells when the compounds were used in conjunction with norfloxacin or oxacillin. When compounds 1, 10, and 11 were used to treat cells in conjunction with PDT, only compound 1 had an increased ability to kill cells.

TABLE 6

| Compound | Synergy with Norfloxacin | Synergy with Oxacillin | PDT |
| --- | --- | --- | --- |
| 1 | 5-log reduction | 5-log reduction | <1-log reduction |
| 10 | 5-log reduction | 4-log reduction | N/A |
| 11 | 8-log reduction | 5-log reduction | N/A |

Figure 9:
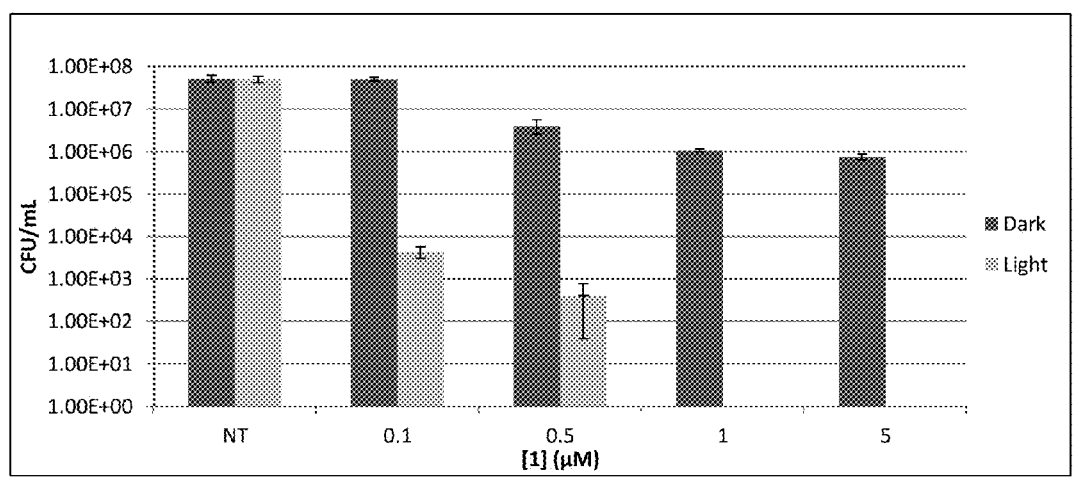
FIG. 9 depicts light-activated killing of community-acquired MRSA with compound 1.

TABLE 7 and FIG. 9 show the light-activated killing of MRSA (ATCC No. BAA-1717; community-acquired MRSA). The error bars in FIG. 9 represent the variations between three replicate determinations. The results indicated that treatment with light and compound 1 led to greater cell toxicity than treatment of the cells with compound 1 alone.

TABLE 7

| Treatment | 1 - Dark Toxicity (CFU/mL) | 1 - Light Toxicity (CFU/mL) |
| --- | --- | --- |
| No treatment | $6.30 \times 10^7 \pm 9.29 \times 10^6$ | $2.94 \times 10^7 \pm 8.89 \times 10^6$ |
| 0.1 µM | $5.10 \times 10^7 \pm 5.29 \times 10^6$ | $4.43 \times 10^3 \pm 1.33 \times 10^3$ |
| 0.5 µM | $4.03 \times 10^6 \pm 1.5 \times 10^6$ | $4.0 \times 10^2 \pm 3.61 \times 10^2$ |
| 1.0 µM | $1.06 \times 10^6 \pm 8.39 \times 10^4$ | None detected (<100 CFU/mL) |
| 5.1 µM | $7.53 \times 10^5 \pm 1.12 \times 10^5$ | None detected (<100 CFU/mL) |

Figure 10:
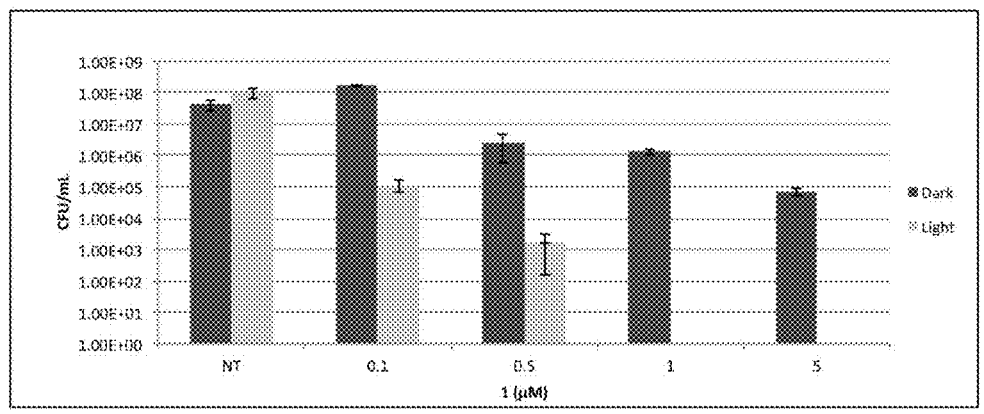
FIG. 10 depicts light-activated killing of S. aureus with compound 1.

TABLE 8 and FIG. 10 show the light-activated killing of S. aureus (ATCC No. 29213). The error bars in FIG. 10 represent the variations between three replicate determinations. The results indicated that treatment with light and compound 1 led to greater cell toxicity than treatment of the cells with compound 1 alone.

TABLE 8

| Treatment | 1 - Dark Toxicity (CFU/mL) | 1 - Light Toxicity (CFU/mL) |
|---|---|---|
| No treatment | $4.27 \times 10^7$  $1.62 \times 10^7$ | $9.93 \times 10^7 \pm 3.83 \times 10^7$ |
| 0.1 μM | $1.63 \times 10^8 \pm 1.72 \times 10^7$ | $1.20 \times 10^5 \pm 5.12 \times 10^4$ |
| 0.5 μM | $2.67 \times 10^6 \pm 2.10 \times 10^6$ | $1.60 \times 10^3 \pm 1.44 \times 10^3$ |
| 1.0 μM | $1.34 \times 10^6 \pm 3.04 \times 10^5$ | None detected (<100 CFU/mL) |
| 5.1 μM | $7.13 \times 10^4 \pm 1.80 \times 10^4$ | None detected (<100 CFU/mL) |

Figure 11:
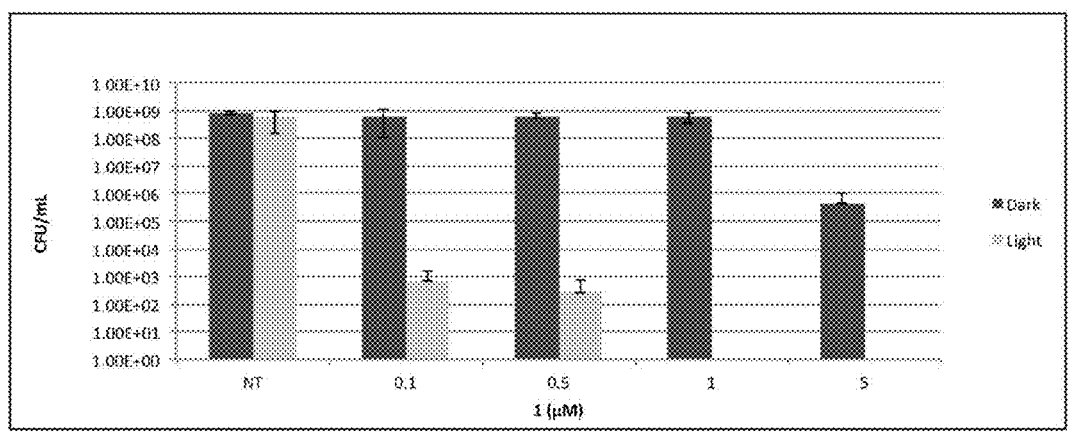
FIG. 11 depicts light-activated killing of VRE with compound 1.

TABLE 9 and FIG. 11 show the light-activated killing of VRE (ATCC No. 51299). The error bars in FIG. 11 represent the variations between three replicate determinations. The results indicated that treatment with light led to greater cell toxicity than treatment of the cells with compound 1 alone.

TABLE 9

| Treatment | 1 - Dark Toxicity (CFU/mL) | 1 - Light Toxicity (CFU/mL) |
|---|---|---|
| No treatment | $8.67 \times 10^8 \pm 1.40 \times 10^8$ | $5.78 \times 10^8 \pm 4.27 \times 10^8$ |
| 0.1 μM | $6.50 \times 10^8 \pm 5.40 \times 10^8$ | $7.00 \times 10^2 \pm 8.19 \times 10^2$ |
| 0.5 μM | $6.50 \times 10^8 \pm 1.32 \times 10^8$ | $2.67 \times 10^2 \pm 4.62 \times 10^2$ |
| 1.0 μM | $6.20 \times 10^8 \pm 2.62 \times 10^8$ | None detected (<100 CFU/mL) |
| 5.0 μM | $4.55 \times 10^5 \pm 8.87 \times 10^5$ | None detected (<100 CFU/mL) |

Figure 12:
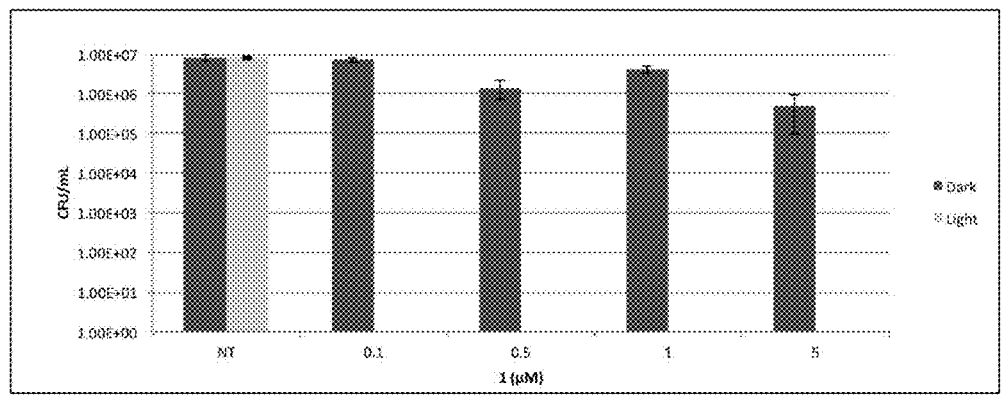
FIG. 12 depicts light-activated killing of S. pyogenes with compound 1.

TABLE 10, TABLE 11, and FIG. 12 show the light-activated killing of *S. pyogenes* (ATCC No. 8133). TABLE 10 depicts the MICs of compound 1 and light when used individually to treat *S. pyogenes*. The results in TABLE 11 indicated that treatment with light and compound 1 led to greater cell toxicity than treatment of the cells with compound 1 or light alone. The error bars in FIG. 12 represent the variations between three replicate determinations.

TABLE 10

| Drug | *S. pyogenes* MIC |
|---|---|
| Compound 1 | 100 μM |
| Light | No effect |

TABLE 11

| Treatment | 1 - Dark Toxicity (CFU/mL) | 1 - Light Toxicity (CFU/mL) |
|---|---|---|
| No Treatment | $8.00 \times 10^6 \pm 1.42 \times 10^6$ | $7.67 \times 10^6 \pm 7.51 \times 10^5$ |
| 0.1 μM | $7.13 \times 10^6 \pm 1.10 \times 10^6$ | None Detected (<100 CFU/mL) |
| 0.5 μM | $1.40 \times 10^6 \pm 7.05 \times 10^5$ | None Detected (<100 CFU/mL) |
| 1.0 μM | $4.13 \times 10^6 \pm 9.07 \times 10^5$ | None Detected (<100 CFU/mL) |
| 5.0 μM | $5.01 \times 10^5 \pm 4.07 \times 10^5$ | None Detected (<100 CFU/mL) |

Figure 13:
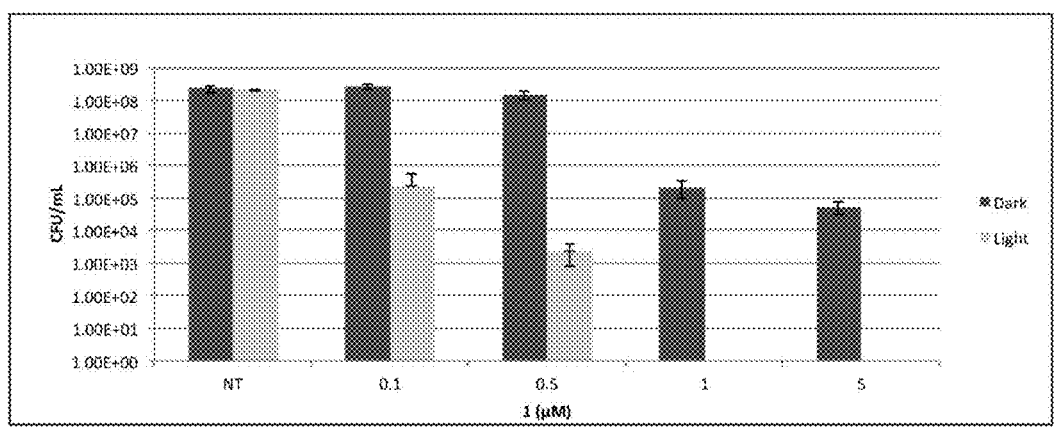
FIG. 13 depicts light-activated killing of S. mutans with compound 1.

TABLE 12, TABLE 13, and FIG. 13 show the light-activated killing of *S. mutans* (Ward's 85W 2357). TABLE 12 depicts the MICs of compound 1 and light when used individually to treat *S. mutans*. The results in TABLE 13 indicated that treatment with light and compound 1 led to greater cell toxicity than treatment of the cells with compound 1 or light alone. The error bars in FIG. 13 represent the variations between three replicate determinations.

TABLE 12

| Drug | *S. mutans* MIC |
|---|---|
| Compound 1 | 50-100 μM |
| Light | No effect |

TABLE 13

| Treatment | 1 - Dark Toxicity (CFU/mL) | 1 - Light Toxicity (CFU/mL) |
|---|---|---|
| No Treatment | $2.27 \times 10^8 \pm 6.35 \times 10^7$ | $2.03 \times 10^8 \pm 5.77 \times 10^6$ |
| 0.1 μM | $2.6 \times 10^8 \pm 5.57 \times 10^7$ | $2.35 \times 10^5 \pm 3.50 \times 10^5$ |
| 0.5 μM | $1.44 \times 10^8 \pm 4.46 \times 10^7$ | $2.33 \times 10^3 \pm 1.54 \times 10^3$ |
| 1.0 μM | $2.1 \times 10^5 \pm 1.13 \times 10^5$ | None Detected (<100 CFU/mL) |
| 5.0 μM | $5.5 \times 10^4 \pm 2.48 \times 10^4$ | None Detected (<100 CFU/mL) |

Example 8: Light-Activated Killing of Gram-Positive Organisms with Compound 1 and Structural Analogues of Compound 1

To illustrate the light-induced effects exhibited by structural analogues of compound 1, the minimum bactericidal concentration (MBC) was determined for each of the synthesized analogues. The MBC was defined as the minimum concentration of a compound at which the bacterial cell population is reduced to sterility ($10^6$ CFU/mL reduction after treatment).

The bacterial media was inoculated with bacteria and incubated overnight. The bacterial cultures were diluted to $5 \times 10^8$ CFU/mL using a McFarland latex turbidity standard (0.5). Compound 1 was diluted with sterile DMSO, which was added to the cell suspension in glass culture tubes. The cells were then incubated for 30 minutes at 37° C. on a rotary shaking incubator at 150 rpm. 500 μL of the treated cell suspension was added to a well on a sterile ceramic drop plate. Non-coherent white light from a Lumacare™ LC-122 unit was used to irradiate the samples. The end of the light probe was placed 3 cm above the sample well, perpendicular to the surface of the sample, and light was applied for 2 minutes (15 seconds light, 15 seconds dark). 200 μL of the irradiated sample was transferred to a 96-well plastic microtiter plate and five ten-fold dilutions were made in the media. 10 μL of each dilution was dripped onto an agar media plate and was allowed to streak down the plate by tilting the plate down. The agar plates were incubated at 37° C. overnight and colony counts were performed to calculate the CFU/mL.

TABLE 14 details the MBC values of compounds 1-6 against MRSA with and without irradiation with white light. Irradiation involved treatment with a LumaCare™ light source at 3 cm from media for 1 min.

TABLE 14

| Compound | MBC in the dark (μM) | MBC with irradiation (μM) |
|---|---|---|
| 1 | 200 | 1 |
| 2 | 100 | 0.5 |
| 3 | 200 | 0.5 |
| 4 | 100 | 0.5 |
| 5 | 200 | 0.5 |
| 6 | 200 | 1 |

Example 9: Light-Activated Killing of Human Cell Lines Using Compounds of the Invention TABLE 15 depicts the $IC_{50}$ of compounds in the presence or absence of light for human cell lines. The cell lines used were HeLa (human cervical adenocarcinoma), U-87 MG (human brain gliobastoma), MES-SA (human uterine sarcoma), MES-SA/Dx5 (human uterine sarcoma grown in presence of doxorubicin), NCI-H441 (human lung papillary adenocarcinoma), A549 (human lung carcinoma), WI-38

(human embryonic lung normal), MCF7 (human breast adenocarcinoma), SW1088 (human brain astrocytoma), B16F10 (mouse skin melanoma), NIH-3T3 (mouse fibroblast), and Jurkat (human lymphoblastoma).

"1-Sol" in TABLE 15 was generated by dissolving compound 1 and potassium hydroxide at a 1:1 ratio in a DMSO/water solution. The cells were irradiated with continuous white light using a LumaCare™ light source for 2 minutes at a distance of 6.5 cm from the cells. The results indicated that all the compounds tested became more toxic upon administration of light regardless of whether the compounds were administered with or without KOH, or with or without liposome encapsulation.

TABLE 15

| Compound | Cell Line | Compound IC$_{50}$ (µM) ± SD | Compound + light IC$_{50}$ (µM) ± SD |
|---|---|---|---|
| 1 | HeLa | 9.43 ± 0.40 | <0.4 |
| 1 | HeLa + 5% FBS | 2.9 ± 0.2 | <0.4 |
| 1 | HeLa | >0.8 | 0.125 ± 0.013 |
| 1 | HeLa + 5% FBS | >0.8 | 0.075 ± 0.003 |
| 1 | HeLa | 9.11 ± 0.94 | 0.29 ± 0.02 |
| 1 | U-87 MG | 44.56 ± 3.68 | 0.56 ± 0.02 |
| 1 | U-87 MG (spheroids) | >40 µM | 0.45 |
| 1 | MES-SA | 42.7 ± 3.4 | 0.36 ± 0.05 |
| 1 | MES-SA/Dx5 (no doxorubicin) | 67.2 ± 17.9 | 0.72 ± 0.07 |
| 1 | MES-SA/Dx5 (no doxorubicin) | 30.16 ± 2.12 | 0.62 ± 0.03 |
| 1 | MES-SA/Dx5 + doxorubicin | 38.78 ± 2.76 | 0.44 ± 0.1 |
| 1 | NCI-H441 | 50.69 ± 4.37 | 0.76 ± 0.07 |
| 1 | A549 | 17.35 ± 1.52 | 0.84 ± 0.32 |
| 1 | WI-38 | 63.35 ± 5.48 | 0.33 ± 0.08 |
| 1 | MCF7 | 17.82 ± 0.22 | 0.33 ± 0.04 |
| 1 | SW1088 | >50 | 0.47 ± 0.03 |
| 1 | B16F10 | 18.66 ± 0.99 | 0.41 ± 0.22 |
| 1 | MCF7 | 17.82 ± 0.22 | 0.33 ± 0.04 |
| 1 | MCF7A | 24.5 ± 0.2 | 0.40 ± 0.01 |
| 1 | SW1088 | >50 | 0.47 ± 0.03 |
| 1 | B16F10 | 18.66 ± 0.99 | 0.41 ± 0.22 |
| 1-Sol | HeLa | 55.6 ± 1.44 | 0.33 ± 0.04 |
| 1-Sol | U-87 MG | 71.23 ± 4.07 | 0.69 ± 0.41 |
| 4 | U-87 MG | 42.57 ± 5.53 | 1.01 ± 0.16 |
| 4 | MES-SA/Dx5 (no doxorubicin) | 57.2 ± 10.3 | 1.31 ± 0.51 |
| 4 | MES-SA/Dx5 + doxorubicin | 40.94 ± 1.36 | 0.67 ± 0.01 |
| 1 | Jurkat | >10 uM | 0.025 uM |
| 1 in liposomes | Jurkat | >10 uM | 0.050 uM |

Example 10: Light-Activated Killing of Parasites Using Compounds of the Invention The results in TABLE 16 indicate that the compounds of the invention became more potent upon being exposed to light when used to treat protozoa. Trypanosomes were cultured in LIT media+10% FBS. The compounds were added to create a dilution series and incubated with the trypanosomes for 1 hour. The trypanosomes were then irradiated with continuous white light for 2 minutes at a distance of 6.5 cm using a LumaCare™ light source. 24 hours later, an MTT assay was performed, which was confirmed by visual inspection, to determine the IC$_{50}$ values.

TABLE 16

| Compound | Protozoan parasite | IC$_{50}$ (µM) | Compound + light IC$_{50}$ (µM) |
|---|---|---|---|
| 1 | Trypanosoma cruzi | >100 µM | <0.5 µM |
| 1-Sol | Trypanosoma cruzi | >100 µM | <0.5 µM |
| 4-Sol | Trypanosoma cruzi | >100 µM | <0.5 µM |

Example 11: Synergy of Compound 1 with Antibiotics Against MRSA and Gram-Negative Bacteria Depicted Via an Isobologram The synergy of two compounds with varying relative potencies can be represented using an isobologram. An isobologram plots the normalized effective concentrations of each drug on each axis, where the sum of the two concentrations equals the line of additivity. Outside the line of additivity, when the sum>1, the effect of the two drugs is considered antagonistic; inside of the line of additivity, when the sum<1, the effect of the two drugs is considered super additive, or when the sum≤0.5, the effect of the two drugs is considered synergistic.

Figure 14:
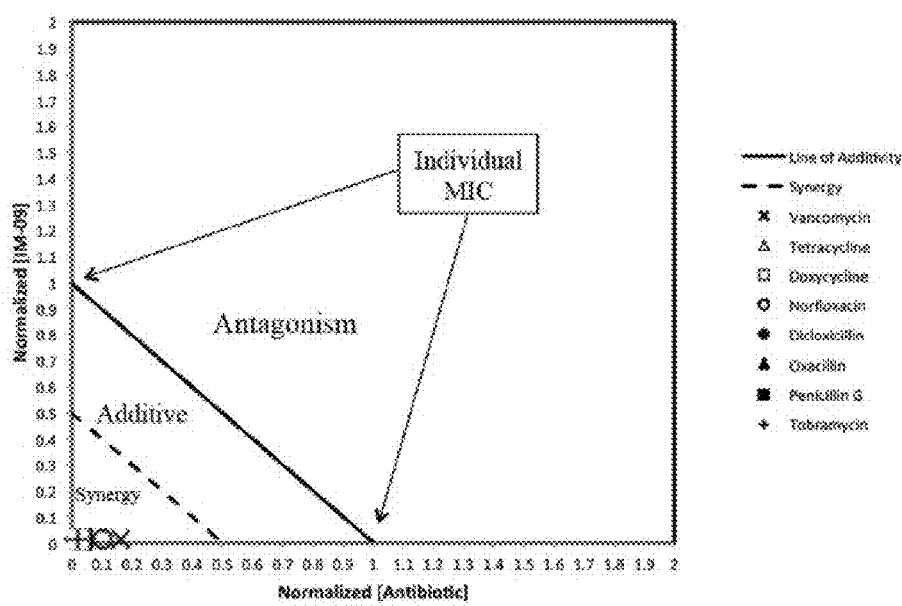
FIG. 14 represents an isobologram for synergy between compound 1 and various antibiotics.
Figure 15:
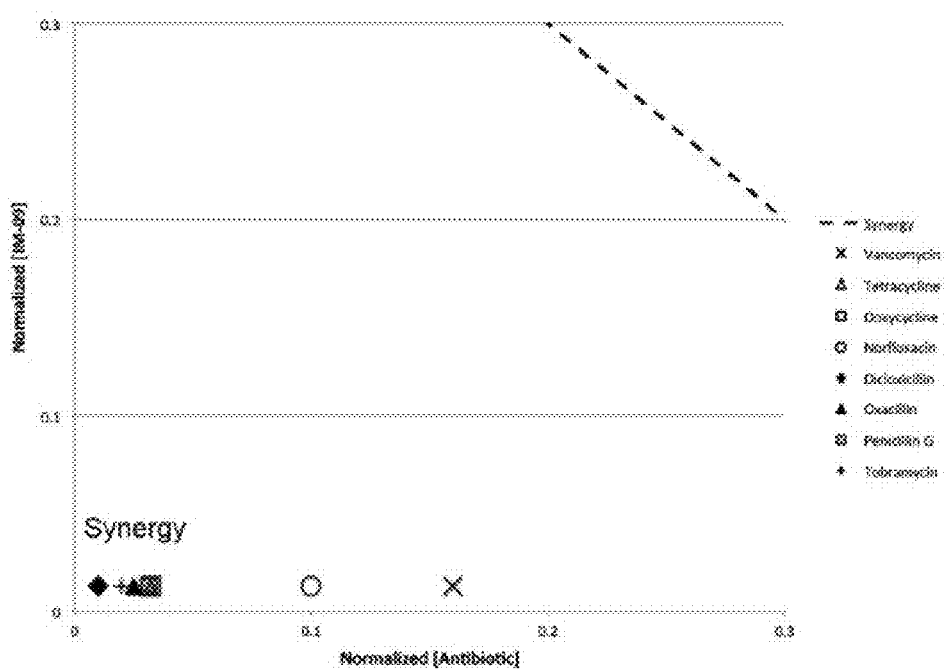
FIG. 15 represents a zoomed-in portion of the isobologram from FIG. 14.

The synergy of compound 1 with vancomycin, tetracycline, doxycycline, norfloxacin, dicloxicillin, oxacillin, penicillin G, and tobramycin was tested. An illustrative example based on a single data point for each antibiotic in combination with compound 1 against MRSA (ATCC No. BAA-44) is shown in FIG. 14. A zoomed-in isobologram for the same data as shown in FIG. 14 is depicted in FIG. 15 specifically for the synergistic area. The results indicated that compound 1 was able to synergize with every tested antibiotic.

Example 12: Synergy of Compound 1 with Antibiotics Against MRSA and Gram-Negative Bacteria Depicted Via a Checkerboard Assay Another method for determining synergy is a checkerboard assay. A checkerboard assay is performed whereby one of the test compounds is serially diluted horizontally across a plate, while the other test compound is serially diluted vertically down the plate. The perpendicular serial dilutions result in combinations of the compounds that range in concentrations from the highest to the lowest of each compound added. In the present study, the checkerboard assay method was adjusted by serially diluting one of the test compounds horizontally and adding the second drug to each well at a concentration of ¼ MIC. The 24-well microtiter plate was then incubated at 37° C. for 18-24 hours on a rotary shaker incubator at 150 rpm. After incubation, MTT reagent was added to each well at a 10% sample volume. Synergy was determined on the lowest concentration of the combined drugs, which produced no purple coloring. Calculation of synergy was determined by the Fractional Inhibitory Concentration Index (FICI): FICI=([Drug 1]$_{Synergy}$/[Drug1]$_{MIC}$)+([Drug 2]$_{Synergy}$/[Drug 2]$_{MIC}$). FICI≤0.5 is an indication of synergy. Several commercially available antibiotics from mechanistically varied families tested in combination with compound 1 were found to have FICI values ≤0.5.

TABLE 17 details the obtained FICI values for compound 1 in combination with varying antibiotics against MRSA, *A. baumannii*, and *E. coli*.

TABLE 17

| Bacteria | Compound | Antibiotic | FIC Index |
|---|---|---|---|
| MRSA | 1 | Ampicillin | 0.13 |
| MRSA | 1 | Amoxicillin | 0.3 |
| MRSA | 1 | Tetracycline | 0.4 |
| MRSA | 1 | Dicloxicillin | 0.04 |
| MRSA | 1 | Norfloxacin | 0.3 |
| A. baumannii | 1 | PMB | 0.1 |
| E. coli | 1 | PMB | 0.2 |

Figure 16:
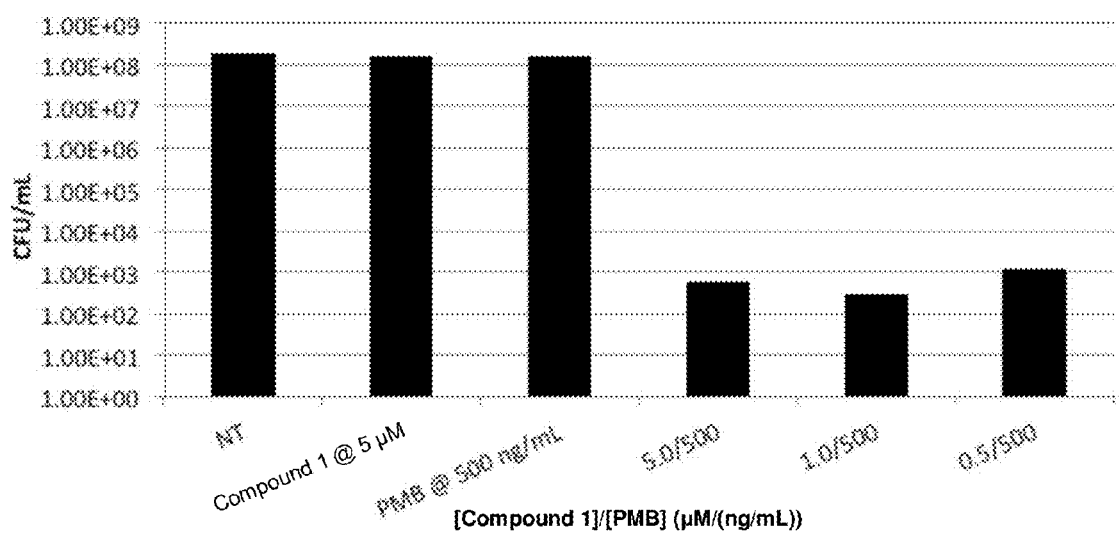
FIG. 16 illustrates the effect of treatment of A. baumannii with compound 1 and polymyxin B.

Example 13: Treatment of *A. baumannii* with Compound 1 and PMB at Fixed Concentrations FIG. 16 demonstrates that the combination of compound 1 and PMB was effective at killing *A. baumannii*, as indicated by a decrease in the concentration of CFU compared to when either agent was used alone.

Example 14: Treatment of *E. coli* with Compound 1, PMB, PME, and Light at Fixed Concentrations TABLE 18 details the obtained MIC values for cells treated with compound 1, light, PMB, and Polymyxin E (PME) against *E. coli*.

TABLE 18

| Drug | E. Coli MIC |
|---|---|
| Compound 1 | >200 μg/mL |
| Light | No effect |
| PMB | 2 μg/mL |
| PME | 2 μg/mL |

Figure 17:
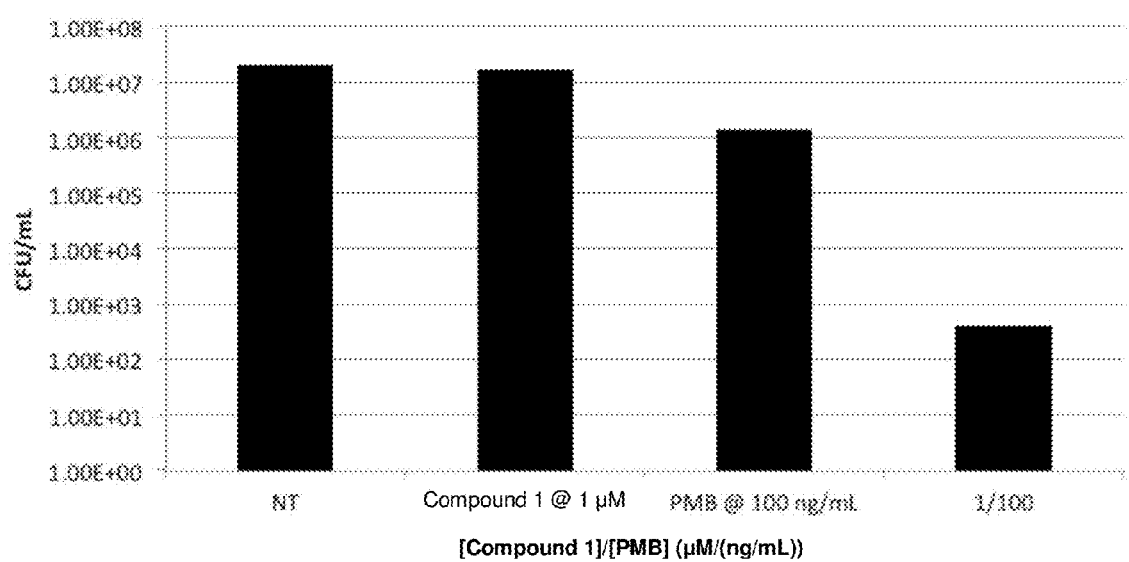
FIG. 17 illustrates the effect of treatment of E. coli with compound 1 and polymyxin B.

FIG. 17 demonstrates that the combination of compound 1 and PMB was effective at killing *E. coli*, as indicated by a decrease in CFU compared to when either agent was used alone.

Example 15: Potentiation of Activity of Compound 1 and Structurally and Mechanistically Unrelated Antibiotics Against Gram-Positive MRSA with a Low Non-Toxic Dose of MTT The potentiation of the antibiotic activity with compound 1 was demonstrated against MRSA (ATCC No. BAA-44) with a dose-dependent assay using 10 μM of compound 1 as an adjuvant. The MICs for the antibiotics in the absence of compound 1 were calculated by adjusting the cells to 5×10$^5$ CFU/mL with McFarland Turbidity Standard (0.5) followed by the addition of an antibiotic. The cells were then incubated at 37° C. for 18 hours on a rotary shaking incubator at 100 rpm. Finally, MTT was added to the cells to assess viability.

To assess the potentiation of antibiotic activity, the cells were adjusted to 5×10$^5$ CFU/mL with McFarland Turbidity Standard (0.5). Compound 1 was then added at 10 μM, and the cells were incubated at 37° C. for 45 minutes. The desired antibiotic was then added at three sub-inhibitory concentrations, and the cells were incubated at 37° C. for 18 hours on a rotary shaking incubator at 100 rpm. The samples were then diluted ten-fold, drip streaked onto a TSA plate, and incubated for 18 hours at 37° C. The resulting cell colonies were counted, and the CFU/mL values were calculated.

Figure 18:
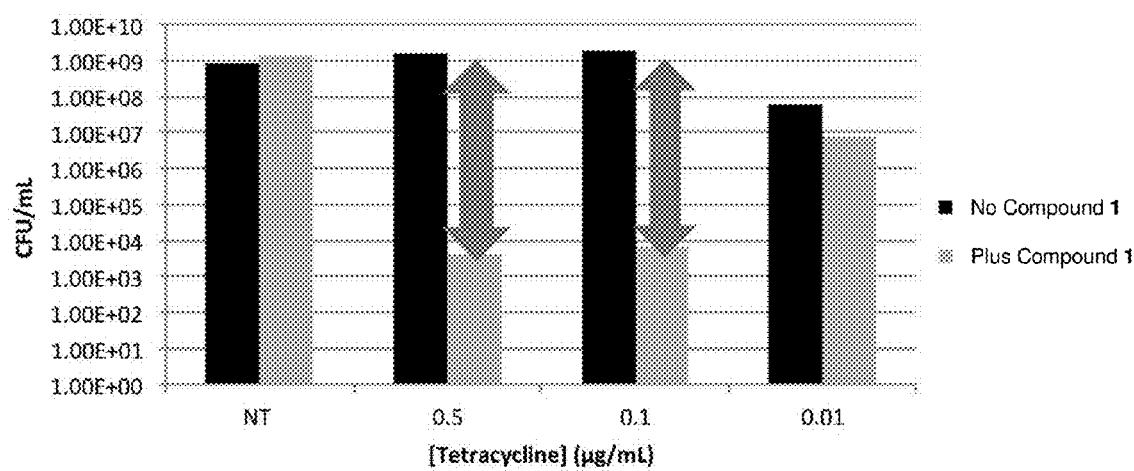
FIG. 18 illustrates the effect of treatment of MRSA with compound 1 and tetracycline.

FIG. 18 shows the MICs of tetracycline in the presence and absence of compound 1, which indicated that tetracycline was more efficacious in cell killing in the presence of compound 1. The arrows highlight the differences in CFU/mL in the presence and absence of compound 1.

Figure 19:
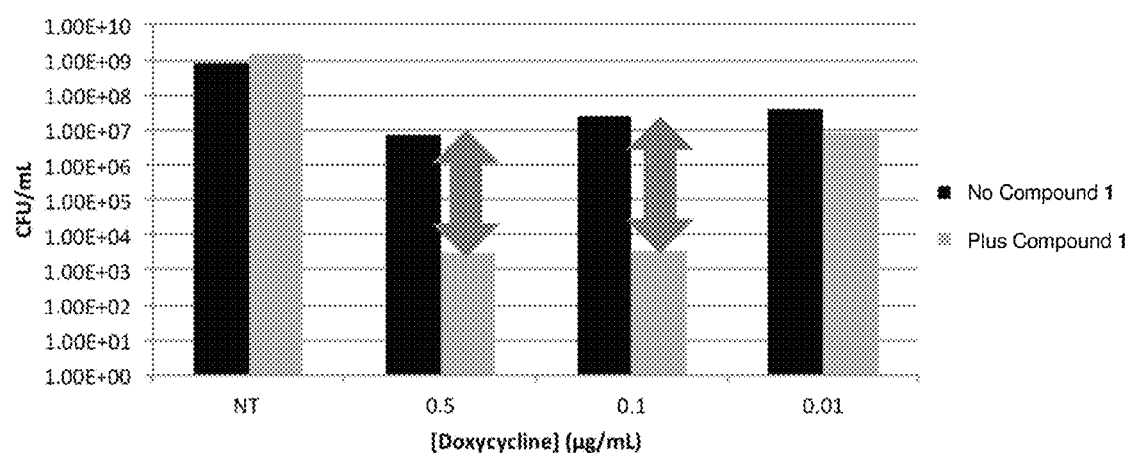
FIG. 19 illustrates the effect of treatment of MRSA with compound 1 and doxycycline.

FIG. 19 shows the MICs of doxycycline in the presence and absence of compound 1, which indicated that doxycycline was more efficacious in cell killing in the presence of compound 1. The arrows highlight the differences in CFU/mL in the presence and absence of compound 1.

Figure 20:
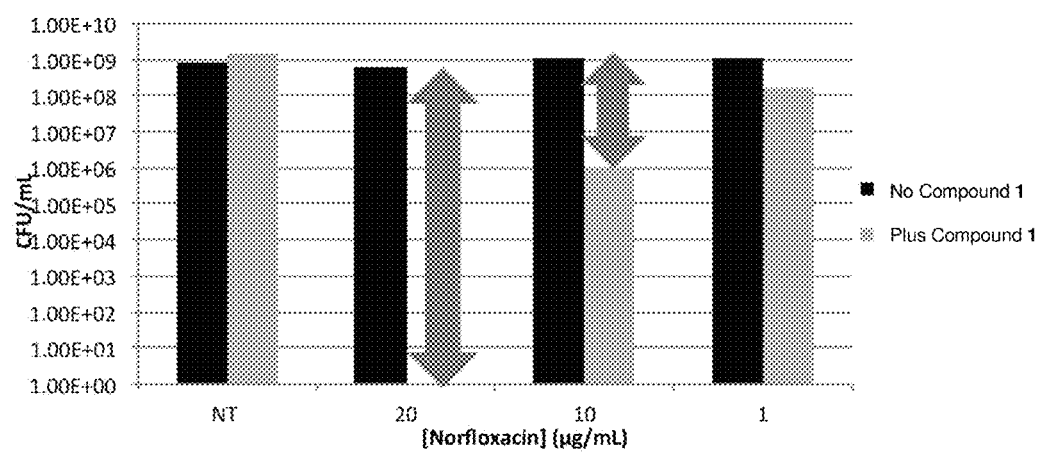
FIG. 20 illustrates the effect of treatment of MRSA with compound 1 and norfloxacin.

FIG. 20 shows the MICs of norfloxacin in the presence and absence of compound 1, which indicated that norfloxacin was more efficacious in cell killing in the presence of compound 1. The arrows highlight the differences in CFU/mL in the presence and absence of compound 1.

Figure 21:
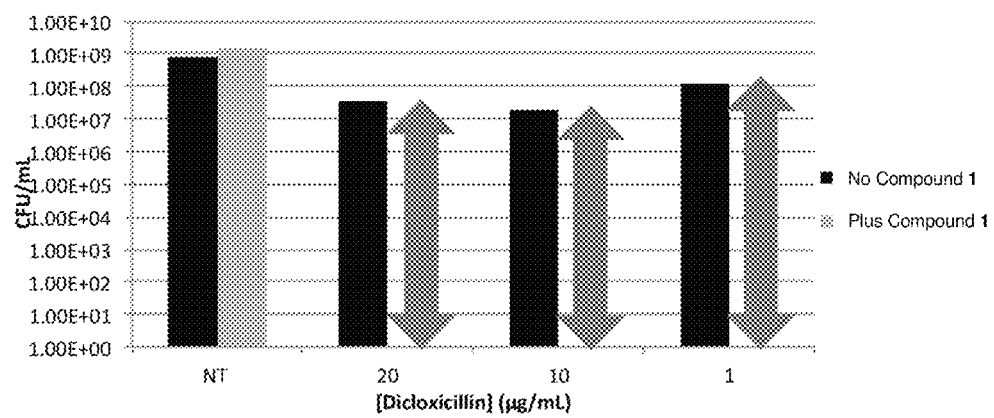
FIG. 21 illustrates the effect of treatment of MRSA with compound 1 and dicloxicillin.

FIG. 21 shows the MICs of dicloxicillin in the presence and absence of compound 1, which indicated that dicloxicillin was more efficacious in cell killing in the presence of compound 1. The arrows highlight the differences in CFU/mL in the presence and absence of compound 1.

Figure 22:
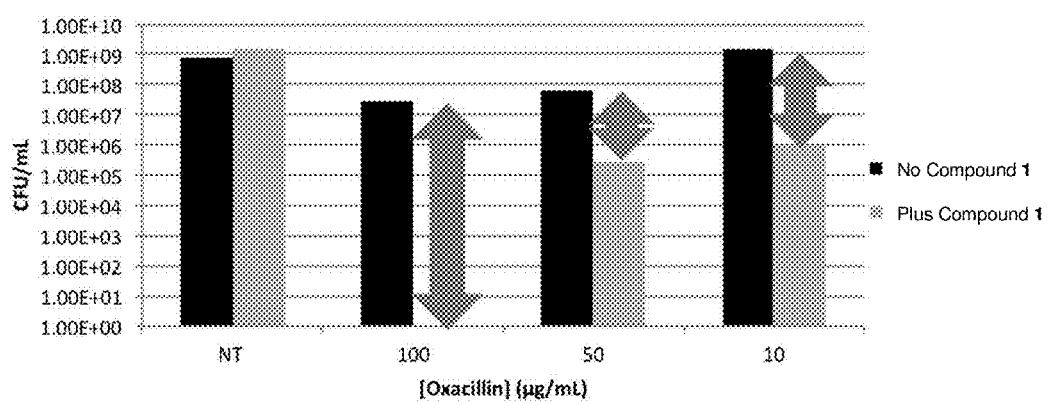
FIG. 22 illustrates the effect of treatment of MRSA with compound 1 and oxacillin.

FIG. 22 shows the MICs of oxacillin in the presence and absence of compound 1, which indicated that oxacillin was more efficacious in cell killing in the presence of compound 1. The arrows highlight the differences in CFU/mL in the presence and absence of compound 1.

Figure 23:
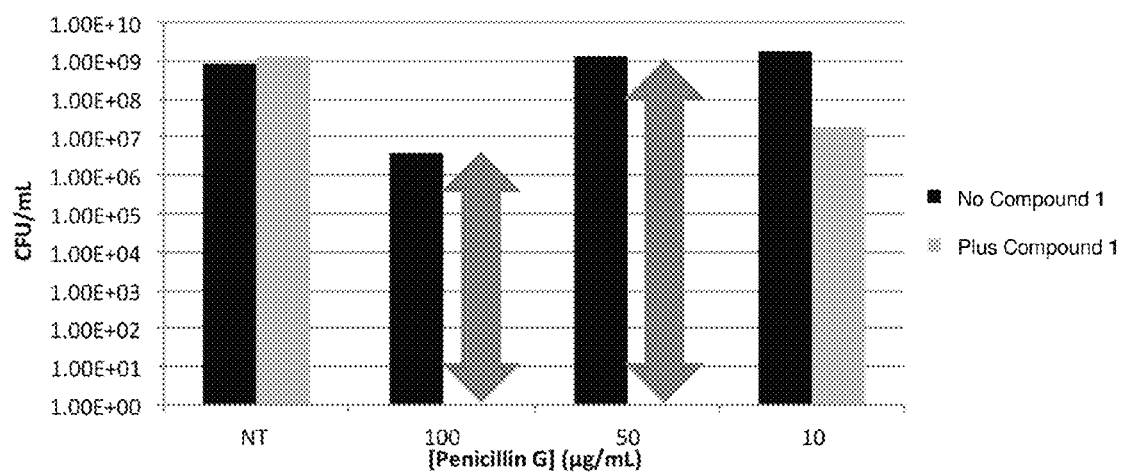
FIG. 23 illustrates the effect of treatment of MRSA with compound 1 and penicillin G.

FIG. 23 shows the MICs of penicillin G in the presence and absence of compound 1, which indicated that penicillin G was more efficacious in cell killing in the presence of compound 1. The arrows highlight the differences in CFU/mL in the presence and absence of compound 1.

Figure 24:
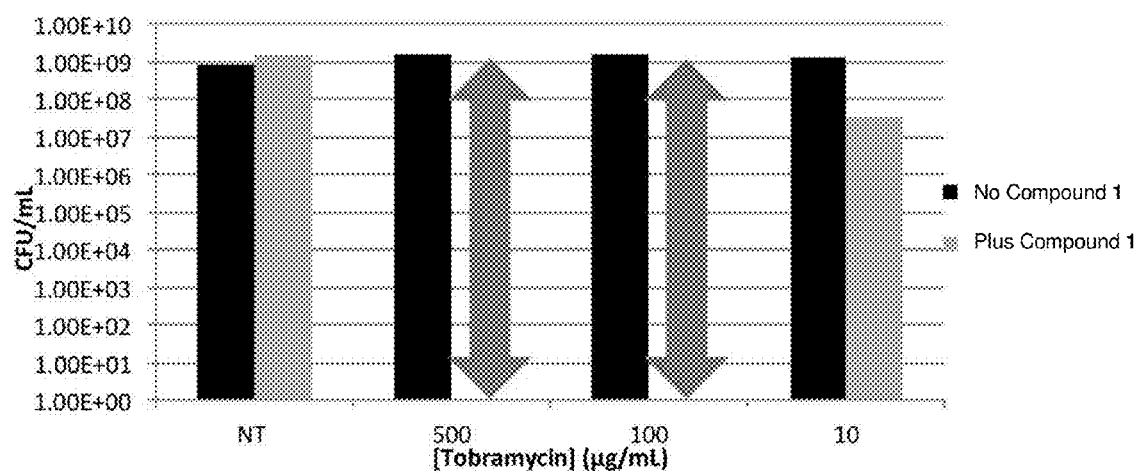
FIG. 24 illustrates the effect of treatment of MRSA with compound 1 and tobramycin.

FIG. 24 shows the MICs of tobramycin in the presence and absence of compound 1, which indicated that tobramycin was more efficacious in cell killing in the presence of compound 1. The arrows highlight the differences in CFU/mL in the presence and absence of compound 1.

Figure 25:
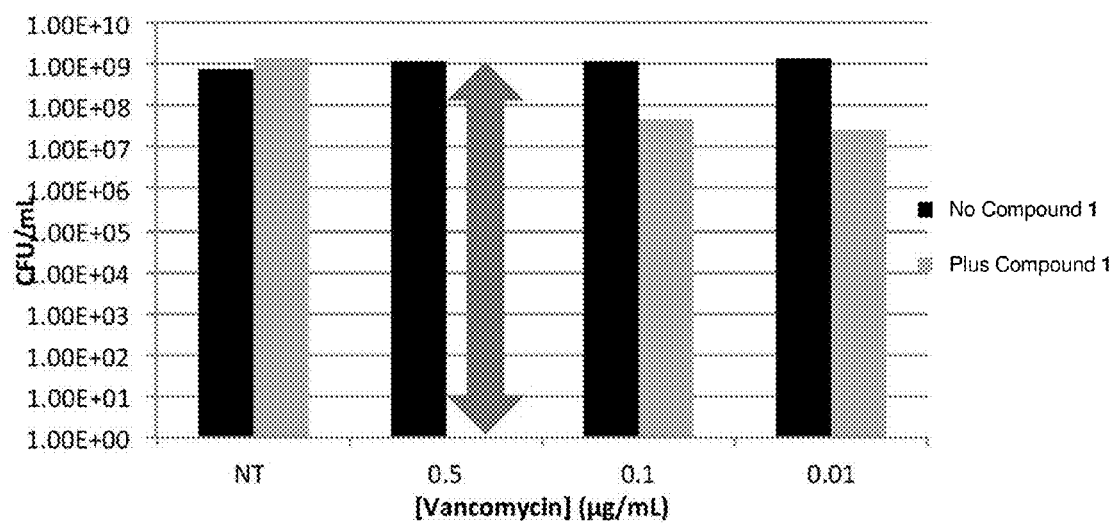
FIG. 25 represents the MIC of vancomycin in presence or absence of compound 1 against MRSA.

FIG. 25 shows the MICs of vancomycin in the presence and absence of compound 1, which indicated that vancomycin was more efficacious in cell killing in the presence of compound 1. The arrows highlight the differences in CFU/mL in the presence and absence of compound 1.

Figure 26:
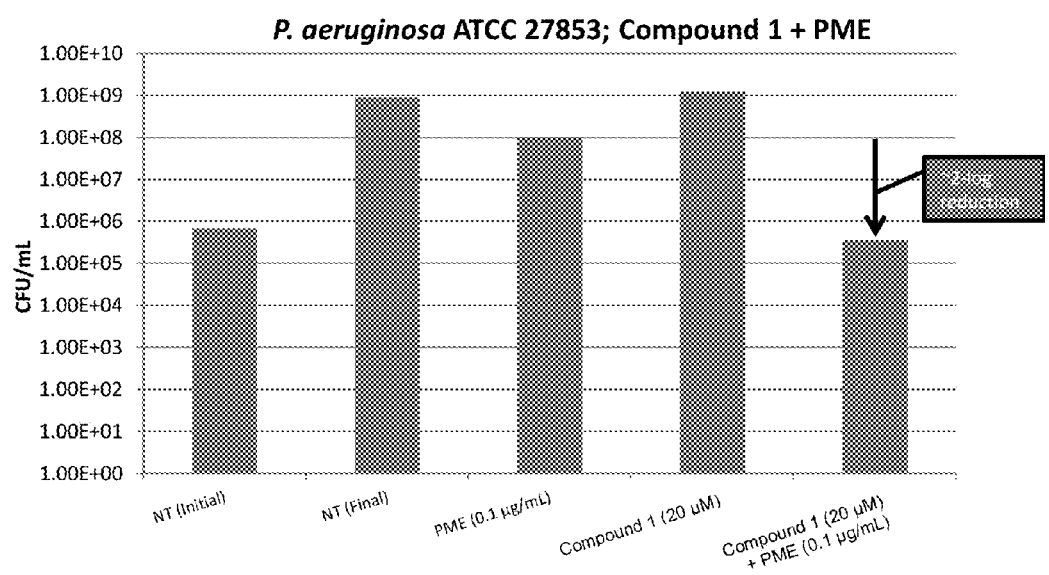
FIG. 26 illustrates the effect of treating P. aeruginosa with compound 1 and polymyxin E.

Example 16: Cell Killing of Gram-Negative *P. aeruginosa* with Compounds of the Invention in the Presence of a Non-Toxic Concentration of PME FIG. 26 is an example of the treatment of *P. aeruginosa* with compound 1 and PME at fixed concentrations. The results indicated that PME was more efficacious in cell killing when co-administered with compound 1. Treatment of cells with 20 µM of compound 1 and 0.1 µg/mL of PME resulted in about a 2-log reduction in the CFU/mL compared to cells that were treated with PME alone.

Figure 27:
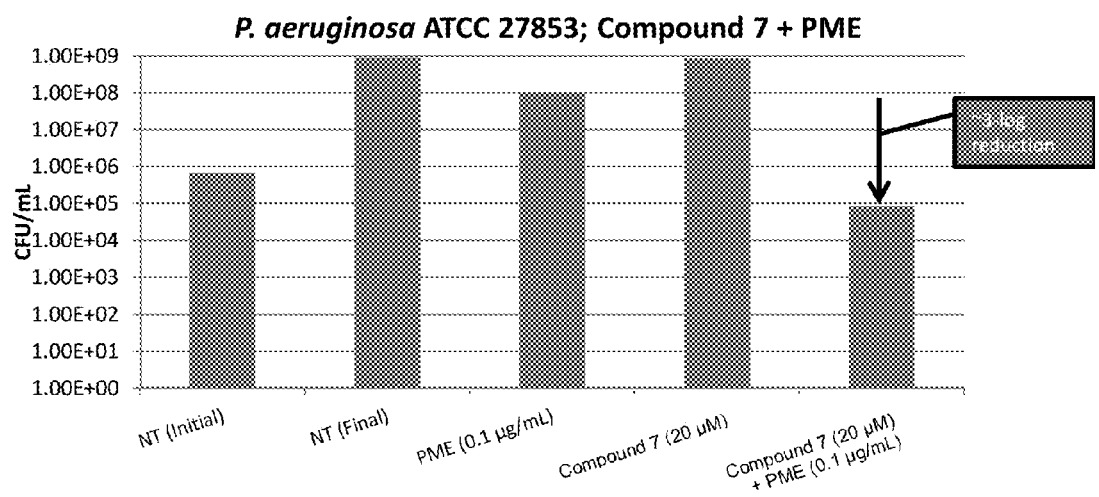
FIG. 27 illustrates the effect of treating P. aeruginosa with compound 7 and polymyxin E.

FIG. 27 is an example of the treatment of *P. aeruginosa* with compound 7 and PME at fixed concentrations. The results indicated that PME was more efficacious in cell killing when co-administered with compound 7. Treatment of cells with 20 µM of compound 7 and 0.1 µg/mL of PME resulted in about a 3-log reduction in the CFU/mL compared to cells that were treated with PME alone.

Figure 28:
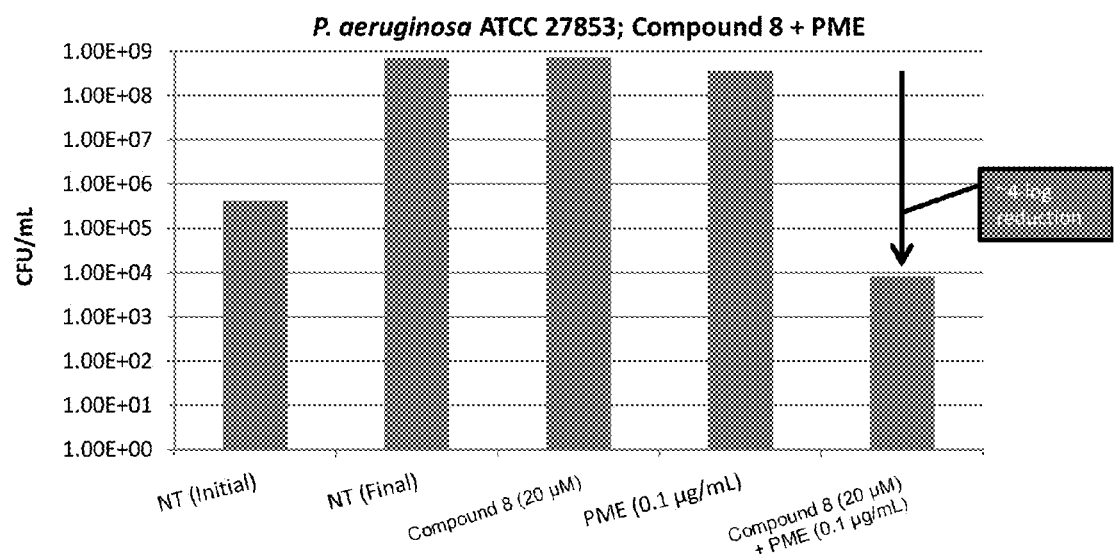
FIG. 28 illustrates the effect of treating P. aeruginosa with compound 8 and polymyxin E.

FIG. 28 is an example of the treatment of *P. aeruginosa* with compound 8 and PME at fixed concentrations. The results indicated that PME was more efficacious in cell killing when co-administered with compound 8. Treatment of cells with 20 µM of compound 8 and 0.1 µg/mL of PME resulted in about a 4-log reduction in the CFU/mL compared to cells that were treated with PME alone.

Figure 29:
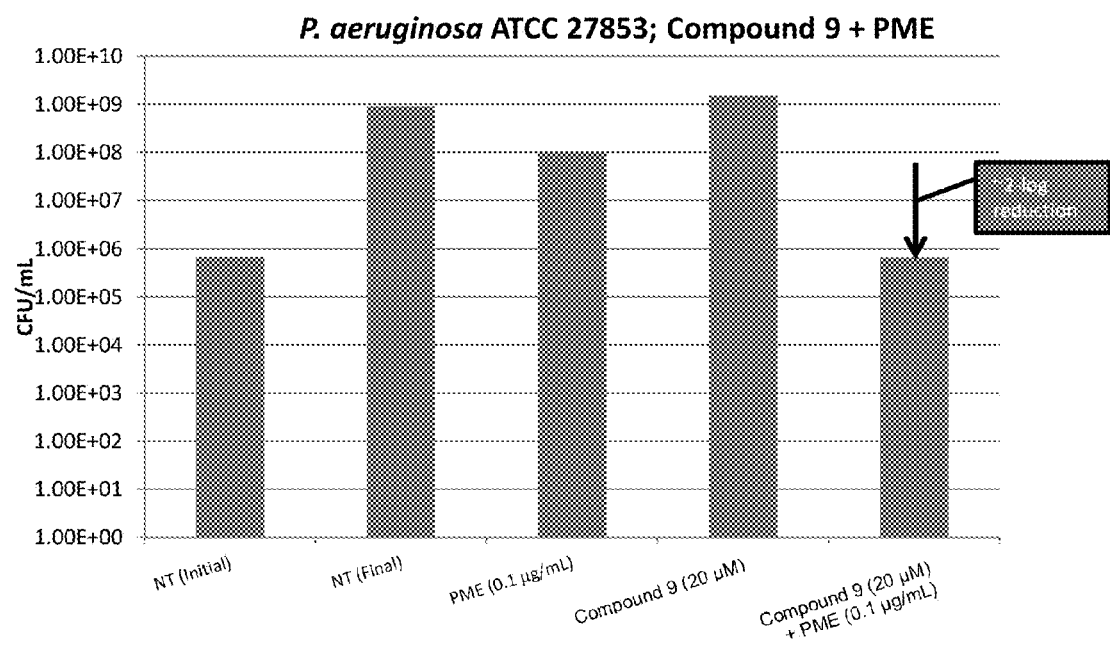
FIG. 29 illustrates the effect of treating P. aeruginosa with compound 9 and polymyxin E.

FIG. 29 is an example of the treatment of *P. aeruginosa* with compound 9 and PME at fixed concentrations. The results indicated that PME was more efficacious in cell killing when co-administered with compound 9. Treatment of cells with 20 µM of compound 9 and 0.1 µg/mL of PME resulted in about a 2-log reduction in the CFU/mL compared to cells that were treated with PME alone.

Figure 30:
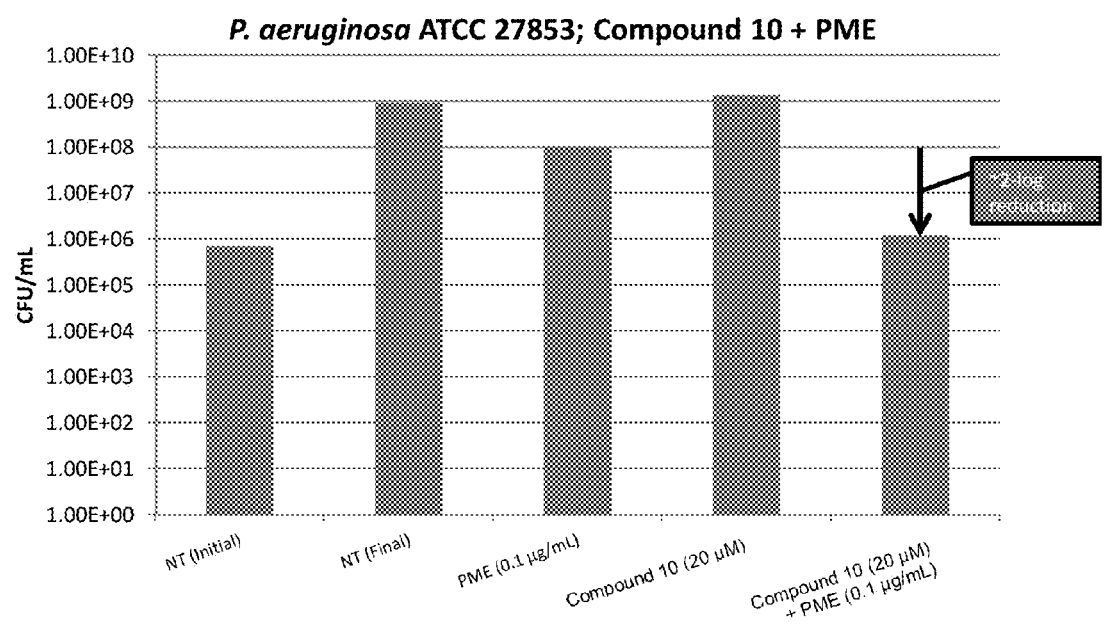
FIG. 30 illustrates the effect of treating P. aeruginosa with compound 10 and polymyxin E.

FIG. 30 is an example of the treatment of *P. aeruginosa* with compound 10 and PME at fixed concentrations. The results indicated that PME was more efficacious in cell killing when co-administered with compound 10. Treatment of cells with 20 µM of compound 10 and 0.1 µg/mL of PME resulted in about a 2-log reduction in the CFU/mL compared to cells that were treated with PME alone.

Figure 31:
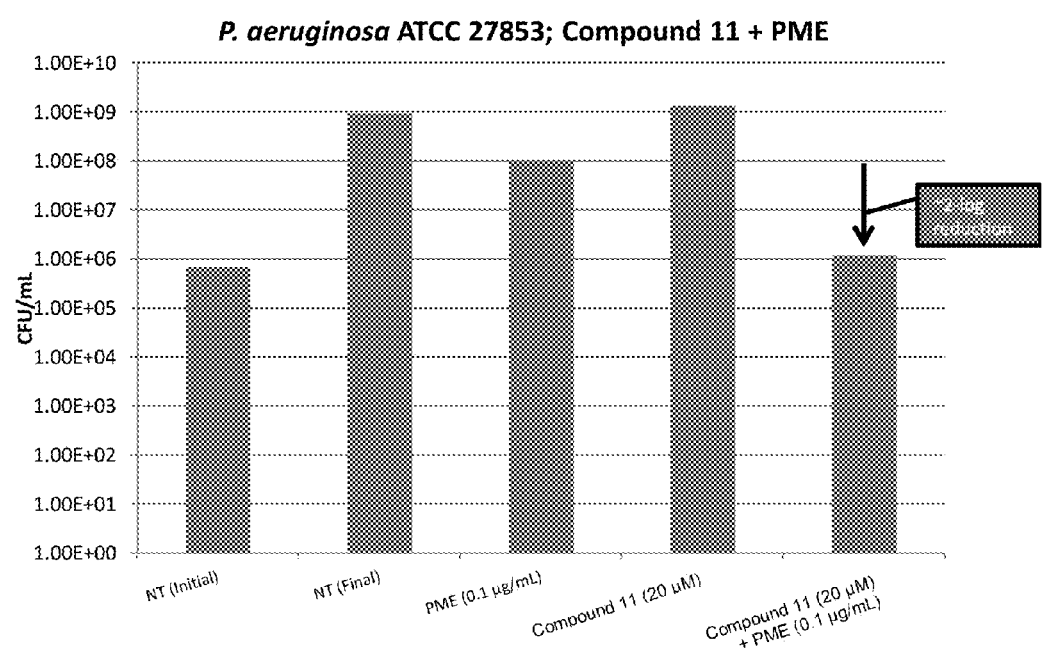
FIG. 31 illustrates the effect of treating P. aeruginosa with compound 11 and polymyxin E.

FIG. 31 is an example of the treatment of *P. aeruginosa* with compound 11 and PME at fixed concentrations. The results indicated that PME was more efficacious in cell killing when co-administered with compound 11. Treatment of cells with 20 µM of compound 11 and 0.1 m/mL of PME resulted in a about 2-log reduction in the CFU/mL compared to cells that were treated with PME alone.

TABLE 19 details the MICs of compounds 1, 7-11, and PME and summarizes the data presented in FIGS. 26-31. Only compound 1 was able to decrease the CFU/mL when used in conjunction with white light to treat *P. aeruginosa*.

TABLE 19

| Compound | MIC | Co-treatment with PME | PDT |
|---|---|---|---|
| 1 | >100 µM | 2-log reduction | ~7-log reduction |
| 7 | >100 µM | 3-log reduction | N/A |
| 8 | >100 µM | 4-log reduction | N/A |
| 9 | >100 µM | 2-log reduction | N/A |
| 10 | >100 µM | 2-log reduction | N/A |
| 11 | >100 µM | 2-log reduction | N/A |
| PME | 2 µg/mL | N/A | N/A |

Example 17: Cell Killing of Gram-Negative *Klebsiella pneumoniae* Using Compounds of the Invention in the Presence or Absence of PMB

*Klebsiella pneumoniae* (CRE, ATCC BAA-1705) was grown in TSB overnight at 37° C. and diluted to about $5 \times 10^5$ CFU/mL using a McFarland Latex Turbidity standard (0.5). One mL of the cell suspension was transferred to a glass culture test tube. PMB was added to the cell suspension resulting in a final concentration of 200 µg/mL of PMB. The cell suspension was incubated at 37° C. on a rotary shaking incubator at 150 rpm for 4 hours. Compounds 1, 7, 8, 9, 10, and 11 were added to the cell suspension, resulting in a concentration of 20 µM for each of the compounds. The cell suspensions containing the compounds were incubated at 37° C. on a rotary shaking incubator at 150 rpm for 4 hours. Each sample was diluted tenfold to a $10^{-5}$ dilution. Ten 10 microliters of each dilution from each sample was dripped onto a TSA plate and allowed to streak down the plate. The agar plates were incubated at 37° C. for 18-24 hours. Colony counts were performed and CFU/mL values were calculated.

TABLE 20 below depicts the ability of the compounds of the invention to kill CRE in the presence of PMB. The results indicate that the CFU of CRE decreased during combination treatment with compounds of the invention and PMB.

TABLE 20

| Compound | No Treatment | PMB @ 0.2 µg/mL | Comp @ 20 mM | PMB + Comp |
|---|---|---|---|---|
| 1 | $6.6 \times 10^8$ CFU/mL | $1.8 \times 10^6$ CFU/mL | $6.4 \times 10^8$ CFU/mL | $8.2 \times 10^3$ CFU/mL |
| 7 | $6.6 \times 10^8$ CFU/mL | $1.8 \times 10^6$ CFU/mL | $6.9 \times 10^8$ CFU/mL | 100 CFU/mL |
| 8 | $6.6 \times 10^8$ CFU/mL | $1.8 \times 10^6$ CFU/mL | $6.6 \times 10^8$ CFU/mL | None Detected |
| 9 | $6.6 \times 10^8$ CFU/mL | $1.8 \times 10^6$ CFU/mL | $6.4 \times 10^8$ CFU/mL | None Detected |
| 10 | $6.6 \times 10^8$ CFU/mL | $1.8 \times 10^6$ CFU/mL | $7.9 \times 10^8$ CFU/mL | None Detected |
| 11 | $6.6 \times 10^8$ CFU/mL | $1.8 \times 10^6$ CFU/mL | $7.8 \times 10^8$ CFU/mL | None Detected |

Figure 32:
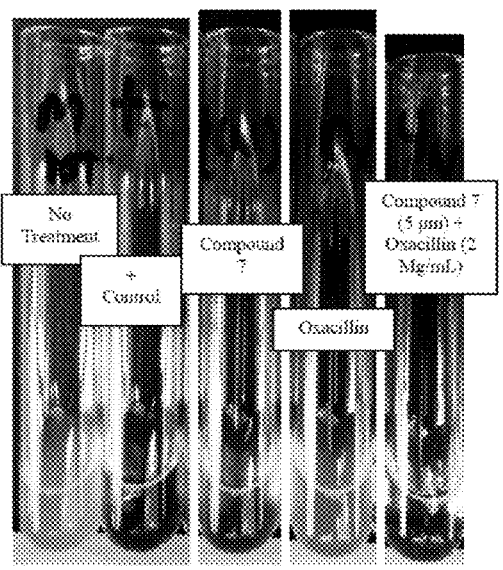
FIG. 32 depicts in image of a turbidity comparison of MRSA isolates treated with compound 7 and/or oxacillin.

Example 18: Turbidity Comparison of MRSA Isolates Treated with Compound 7 and Oxacillin FIG. 32 depicts a turbidity comparison for MRSA (ATCC BAA-44) isolates treated with a positive control (vancomycin), compound 7, oxacillin, and a sample treated with both compound 7 and oxacillin. The results show that the observed turbidity decreased in the following order: no treatment>>oxacillin>>compound 7>>compound 7+oxacillin>positive control.

Figure 33:
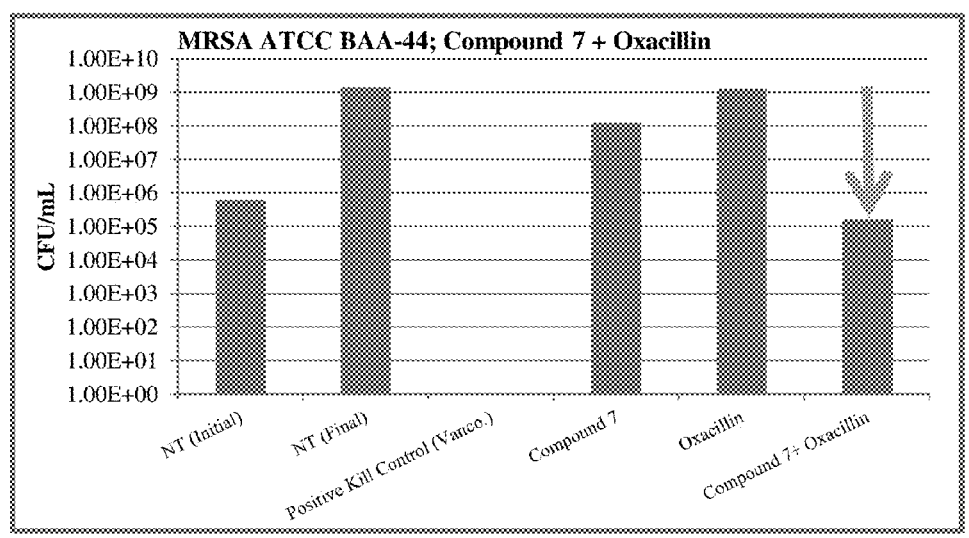
FIG. 33 depicts the quantification of the MRSA isolates shown in FIG. 32 upon being treated with compound 7 and/or oxacillin.

FIG. 33 depicts the corresponding colony concentrations for the MRSA isolates shown in FIG. 32. The arrow in FIG. 33 shows that co-treatment of MRSA with compound 7 and oxacillin was more effective at killing cells than individual treatments with compound 7 or oxacillin.

Example 19: Synergy of Compounds 1 and Compounds 7-11 with Antibiotics Against Gram-Positive *S. aureus*

The synergy of compounds 1 and 7-11 with oxacillin and norfloxacin was tested against MRSA (ATCC BAA-44). An overnight culture of MRSA was first diluted to about $5 \times 10^5$ CFU/mL in TSB. Then, 1 mL of the diluted broth suspension was added to a borosilicate glass culture tube. An appropriate volume of a compound or an antibiotic drug stock was added to the broth suspension and mixed using a vortex mixer. Then an appropriate volume of an antibiotic was added to test synergy with compounds 7-11. The samples were subsequently mixed using a vortex mixer, and the samples were incubated for 18 hours at 37° C. on a rotary shaking incubator. After 18 hours, the test cultures were diluted ten-fold, 10 µL of each dilution was drip-streaked onto a TSA plate, and the samples were incubated for 18 hours at 37° C. Colony counts were then performed and the CFU/mL values were calculated.

Figure 34:
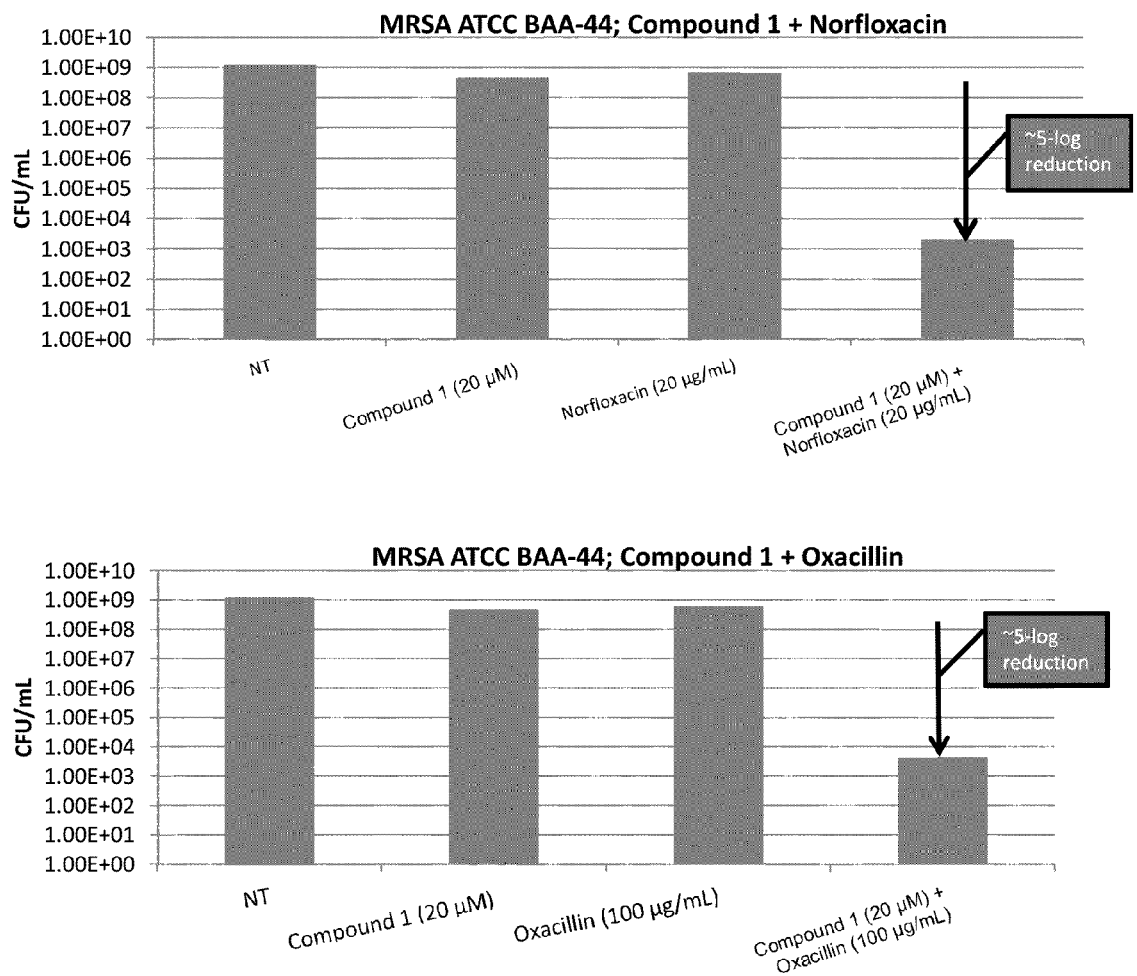
FIG. 34 illustrates the effect of treating MRSA with compound 1 and norfloxacin or oxacillin.

FIG. 34 shows that compound 1 was more effective at killing MRSA when used in conjunction with oxacillin or norfloxacin. The arrows indicate the effect of co-treating cells with compound 1 and an antibiotic in comparison to treatment with compound 1 alone. Cells that received co-treatment with compound 1 and oxacillin or norfloxacin each had about a 5-log reduction in the number of surviving cells (CFU/mL).

Figure 35:
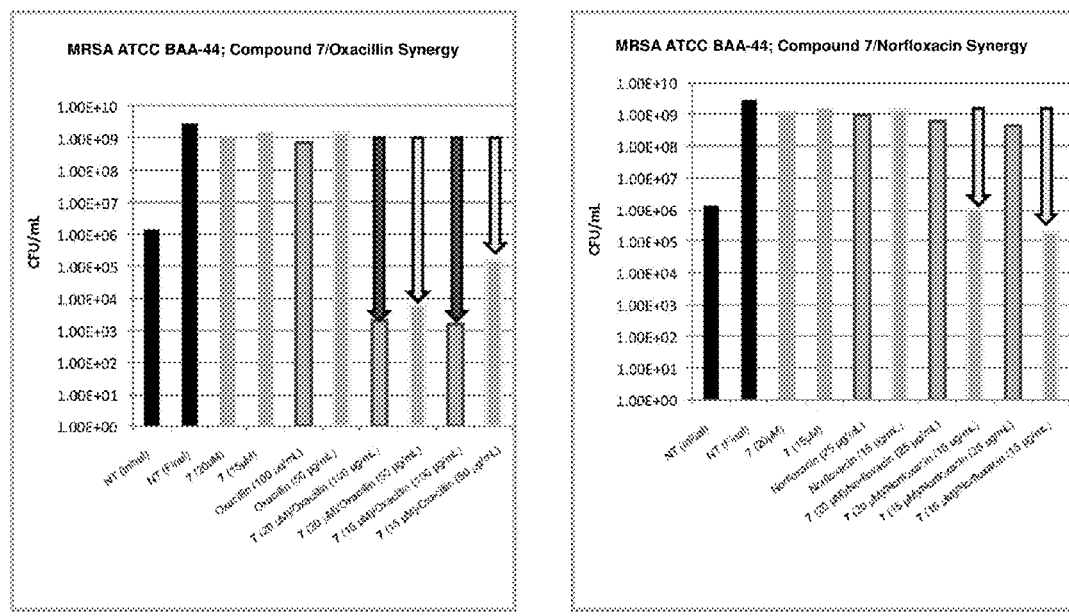
FIG. 35 depicts the synergistic effect of treating MRSA with compound 7 and oxacillin or norfloxacin.

FIG. 35 shows that compound 7 was more effective at killing MRSA when used in conjunction with oxacillin or norfloxacin at two different concentrations. The arrows indicate the synergistic effect of using compound 7 and an antibiotic in comparison to treatment with compound 7 alone. Cells treated with compound 7 and oxacillin or norfloxacin generated MICs that were six-fold and four-fold greater than cells treated with compound 8 alone, respectively.

Figure 36:
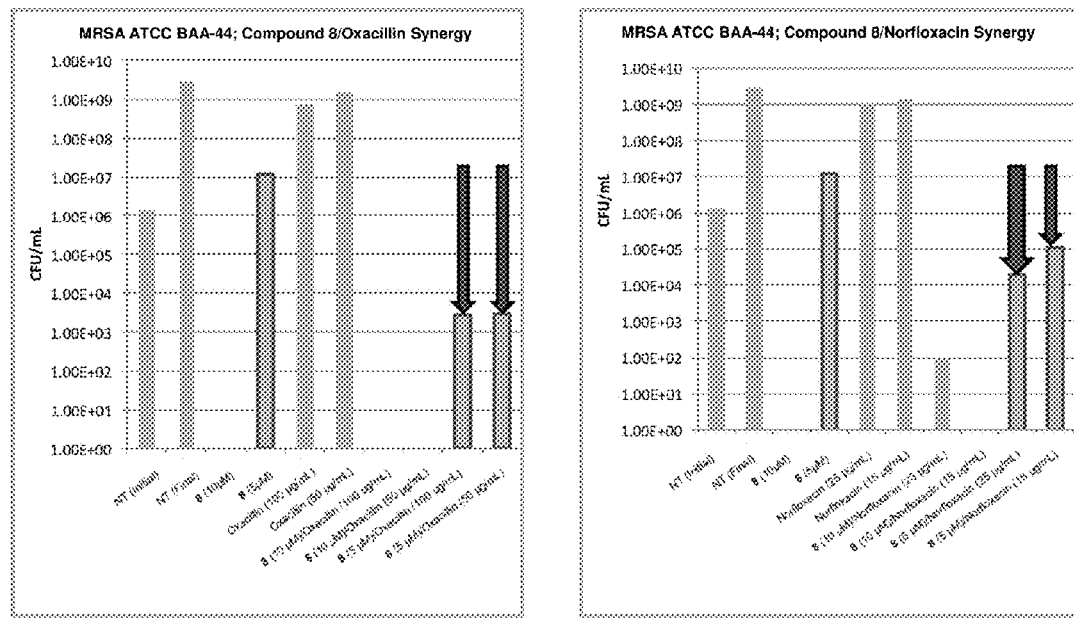
FIG. 36 depicts the synergistic effect of treating MRSA with compound 8 and oxacillin or norfloxacin.

FIG. 36 shows that compound 8 was more effective at killing MRSA when used in conjunction with oxacillin or norfloxacin at two different concentrations. The arrows indicate the synergistic effect of treating cells with compound 8 and an antibiotic in comparison to treatment with compound 8 alone. Cells treated with compound 8 and oxacillin or norfloxacin generated MICs that were three-fold and two-fold greater than cells treated with compound 8 alone, respectively.

Figure 37:
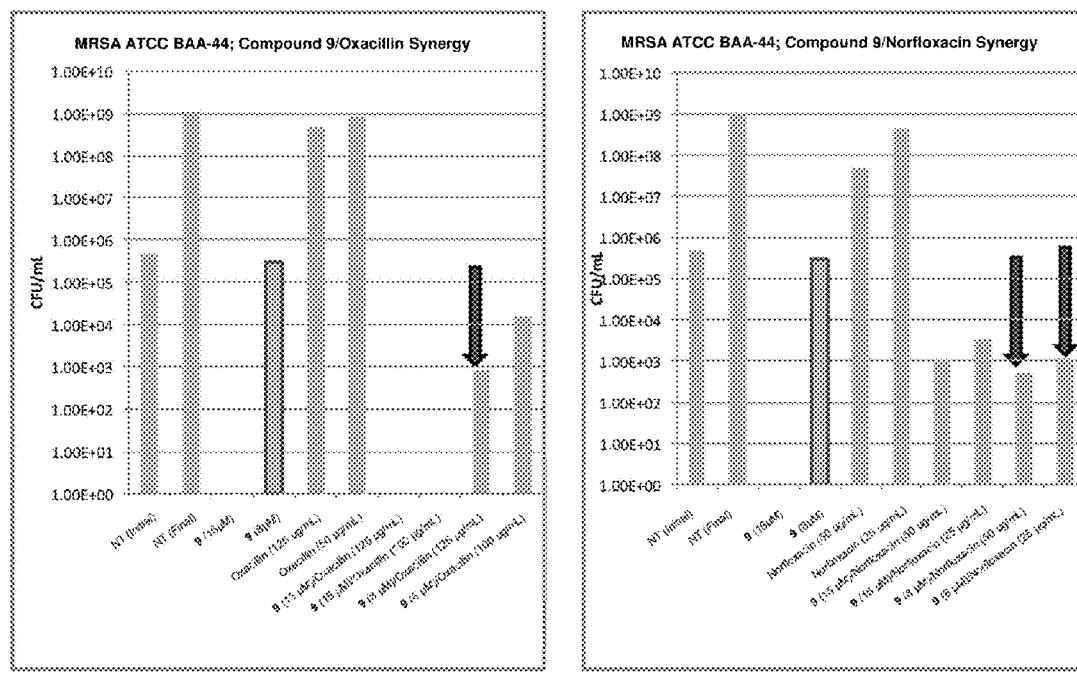
FIG. 37 depicts the synergistic effect of treating MRSA with compound 9 and oxacillin or norfloxacin.

FIG. 37 shows that compound 9 was more effective at killing MRSA when used in conjunction with oxacillin or norfloxacin at varying concentrations. The arrows indicate this synergistic effect in comparison to treatment with compound 9 in the absence of oxacillin or norfloxacin. Cells treated with compound 9 and oxacillin or norfloxacin generated MICs that were two-fold greater than cells treated with compound 9 alone.

Figure 38:
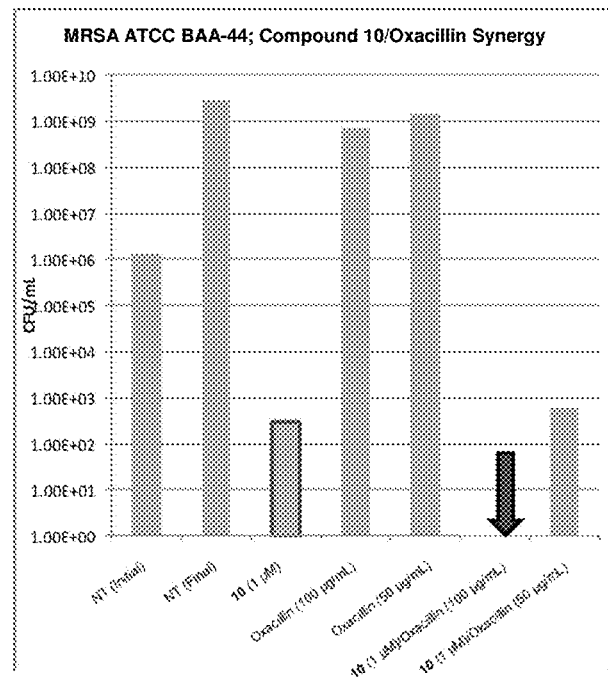
FIG. 38 depicts the synergistic effect of treating MRSA with compound 10 and oxacillin or norfloxacin.

FIG. 38 shows that compound 10 was more effective at killing MRSA when used in conjunction with oxacillin or norfloxacin at varying concentrations. The arrow indicates this synergistic effect in comparison to cell treatment with compound 10 alone. While compound 10 alone was able to effectively kill cells (MIC of 16 µM), cells treated with compound 10 and oxacillin or norfloxacin generated MICs that were eight-fold greater than cells treated with compound 10 alone.

Figure 39:
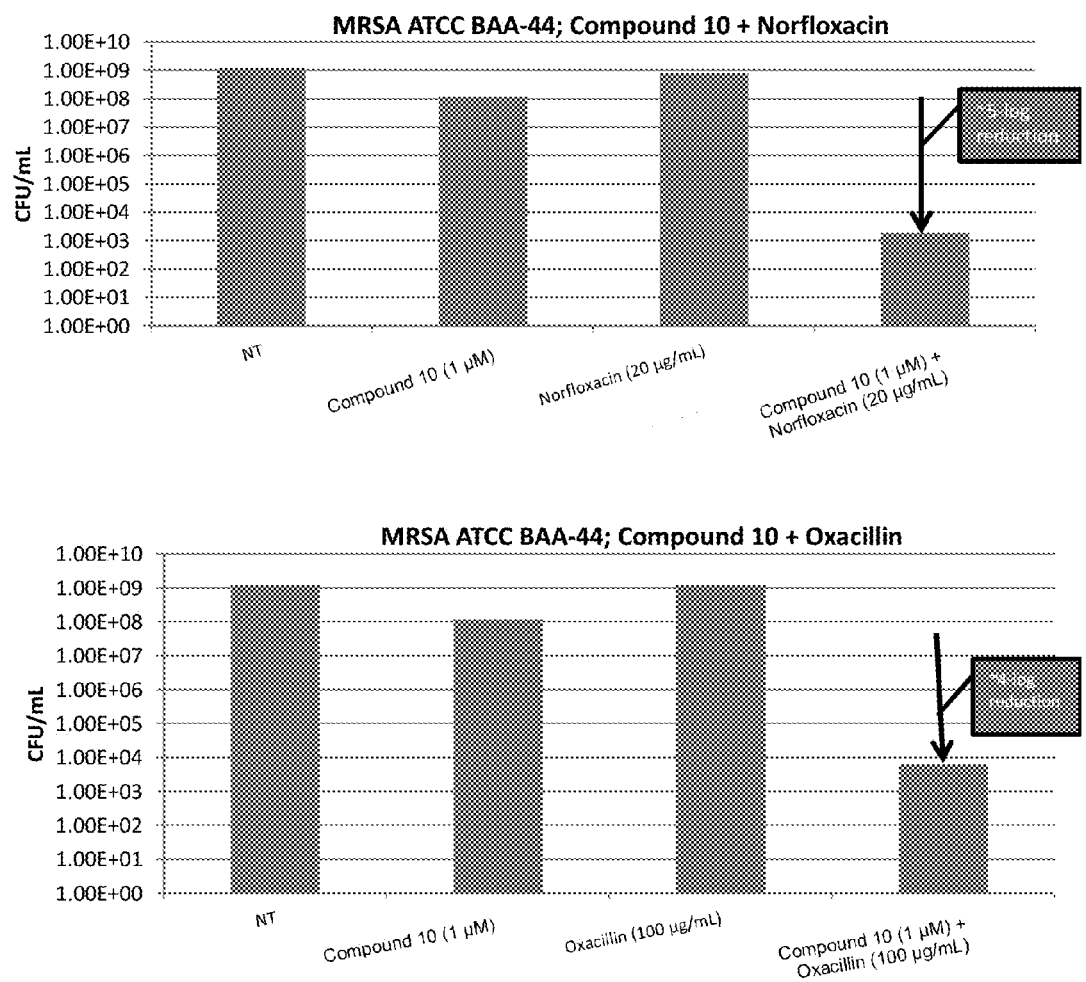
FIG. 39 depicts the synergistic effects of treating MRSA with compound 10 and norfloxacin or oxacillin.

FIG. 39 shows that compound 10 was more effective at killing MRSA when used in conjunction with oxacillin or norfloxacin. The arrows indicate the effect of co-treating cells with compound 1 and oxacillin or norfloxacin in comparison to treatment with compound 10 alone. Cells that received co-treatment with compound 10 and oxacillin or norfloxacin had about a 4-log and about a 5-log reduction in the number of surviving cells (CFU/mL), respectively.

Figure 40:
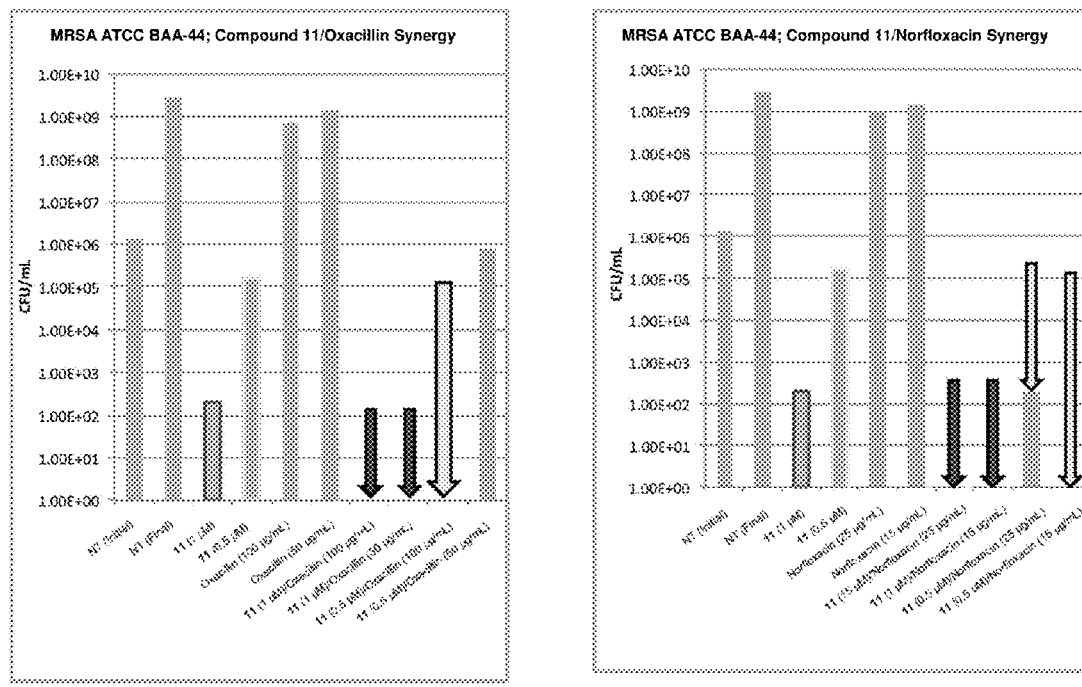
FIG. 40 depicts the synergistic effect of treating MRSA with compound 11 and oxacillin or norfloxacin.

FIG. 40 shows that compound 11 was more effective at killing MRSA when used in conjunction with oxacillin at various concentrations. The dark arrow denotes the synergistic effect in comparison to cell treatment with compound 11 at a concentration of 1 µM in the absence of oxacillin.

Figure 41:
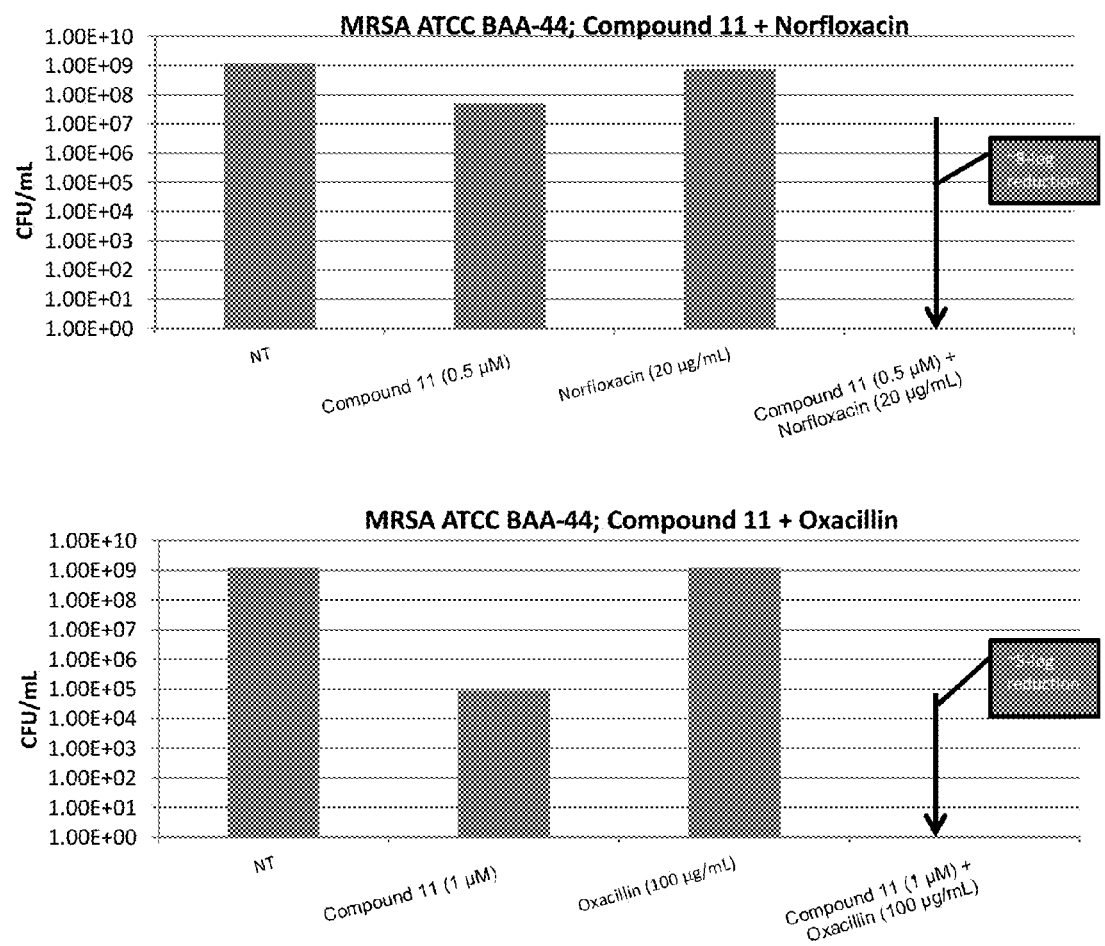
FIG. 41 depicts the synergistic effect of treating MRSA with compound 11 and norfloxacin or oxacillin.

FIG. 41 shows that compound 11 was more effective at killing MRSA when used in conjunction with oxacillin or norfloxacin. The arrows indicate the effect of co-treating cells with compound 11 and oxacillin or norfloxacin in comparison to treatment with compound 11 alone. Cells that received co-treatment with compound 11 and oxacillin or norfloxacin had about a 5-log and about an 8-log reduction in the number of surviving cells (CFU/mL), respectively.

TABLE 21 details the MIC values identified in the MRSA assay of compounds 1, 7, 8, 9, 10, 11, various antibiotics, and light. The results showed that when compounds 1, 7, 8, 9, 10, and 11 were used in conjunction with oxacillin or norfloxacin, their ability to kill MRSA increased by several orders of magnitude compared to treatment with either the drug or compound alone at concentrations well below their respective MICs.

TABLE 21

| | | Orders of Magnitude | |
|---|---|---|---|
| Drug | MRSA MIC | with Oxacillin | with Norfloxacin |
| Compound 1 | 400 µM | >7 | 9 |
| Compound 7 | 100 µM | 6 | 4 |
| Compound 8 | 15 µM | >3 | >2 |
| Compound 9 | 16 µM | >2 | >2 |
| Compound 10 | 16 µM | 8 | 8 |
| Compound 11 | 8 µM | 5 | 5 |
| Dicloxicillin | 500-100 µg/mL | — | — |
| Doxycycline | 3.12 µg/mL | — | — |
| Norfloxacin | 100 µg/mL | — | — |
| Oxacillin | 400 µg/mL | — | — |
| Tetracycline | 3.12 µg/mL | — | — |
| Tobramycin | >5,000 µg/mL | — | — |
| Vancomycin | 3.12 µg/mL | — | — |
| Light | No effect | — | — |

TABLE 22 details the combination effects identified in the MRSA assays of combining compounds 1, 7, 8, 9, 10, and 11 with antibiotics, including dicloxicillin, norfloxacin, oxacillin, tetracycline, tobramycin, vancomycin, and light.

TABLE 22

| (Fraction of MIC) Compound + | (Fraction of MIC) Antibiotic | % Kill | Surviving MRSA |
|---|---|---|---|
| (1/40) Compound 1 | (1/50) Dicloxicillin | 99.99 | $1.00 \times 10^{-8}$ |
| (1/40) Compound 1 | (1/31) Dicloxicillin | 99.99 | $1.00 \times 10^{-4}$ |
| (1/40) Compound 1 | (1/50) Norfloxacin | 99.99 | $1.00 \times 10^{-9}$ |
| (1/40) Compound 1 | (1/4) Oxacillin | 99.99 | $1.00 \times 10^{-7}$ |
| (1/40) Compound 1 | (1/50) Tetracycline | 99.99 | $1.00 \times 10^{-5}$ |
| (1/40) Compound 1 | (1/50) Tobramycin | 99.99 | $1.00 \times 10^{-9}$ |
| (1/40) Compound 1 | (1/6) Vancomycin | 99.99 | $1.00 \times 10^{-9}$ |
| (1/40) Compound 1 | Light | 99.99 | $1.00 \times 10^{-8}$ |
| (1/40) Compound 7 | (1/4) Oxacillin | 99.99 | $1.00 \times 10^{-6}$ |
| (1/4) Compound 7 | (1/2) Norfloxacin | 99.99 | $1.00 \times 10^{-4}$ |

TABLE 22-continued

| (Fraction of MIC) Compound + | (Fraction of MIC) Antibiotic | % Kill | Surviving MRSA |
|---|---|---|---|
| (1/3) Compound 8 | (1/2) Oxacillin | 99.9 | $1.00 \times 10^{-3}$ |
| (1/3) Compound 8 | (1/4) Norfloxacin | 99 | $1.00 \times 10^{-2}$ |
| (1/2) Compound 9 | (1/3) Oxacillin | 99 | $1.00 \times 10^{-2}$ |
| (1/2) Compound 9 | (1/4) Norfloxacin | 99 | $1.00 \times 10^{-2}$ |
| (1/8) Compound 10 | (1/8) Oxacillin | 99.99 | $1.00 \times 10^{-8}$ |
| (1/8) Compound 10 | (1/16) Norfloxacin | 99.99 | $1.00 \times 10^{-8}$ |
| (1/8) Compound 11 | (1/4) Oxacillin | 99.99 | $1.00 \times 10^{-5}$ |
| (1/8) Compound 11 | (1/7) Norfloxacin | 99.99 | $1.00 \times 10^{-5}$ |

Example 20: Synergy of Compounds 7-11 with Antibiotics Against Gram-Positive *Enterococcus faecalis*

TABLE 23 details the MIC values of compounds 1, 7, 8, 9, 10, 11, various antibiotics, and light against VRE.

TABLE 23

| Drug | VRE MIC |
|---|---|
| Compound 1 | >200 μM |
| Compound 7 | >200 μM |
| Compound 8 | 2 μM |
| Compound 9 | >200 μM |
| Compound 10 | 10-20 μM |
| Compound 11 | 20 μM |
| Dicloxicillin | 4 μg/mL |
| Doxycycline | 0.25-0.5 μg/mL |
| Norfloxacin | 2.5 μg/mL |
| Oxacillin | 20-40 μg/mL |
| Tetracycline | 1.25 μg/mL |
| Tobramycin | >200 μg/mL |
| Vancomycin | >40 μg/mL |
| Light | No effect |

Possible synergy of compounds 7-11 with vancomycin, tetracycline, and norfloxacin was tested against VRE (ATCC 51299). For these experiments, overnight cultures of VRE were diluted to about $5 \times 10^5$ CFU/mL in TSB. Then, 1 mL of the diluted broth suspension was added to a borosilicate glass culture tube. After appropriate volumes of the compounds were added to the broth suspensions, the samples were mixed using a vortex mixer, and an appropriate volume of an antibiotic was added to the samples. The samples were mixed using a vortex mixer and incubated for 18 hours at 37° C. on a rotary shaking incubator. After 18 hours, the test cultures were diluted ten-fold, and 10 μL of each dilution was drip-streaked onto a TSA plate and incubated for 18 hours at 37° C. Colony counts were then performed and the CFU/mL values were calculated.

Figure 42:
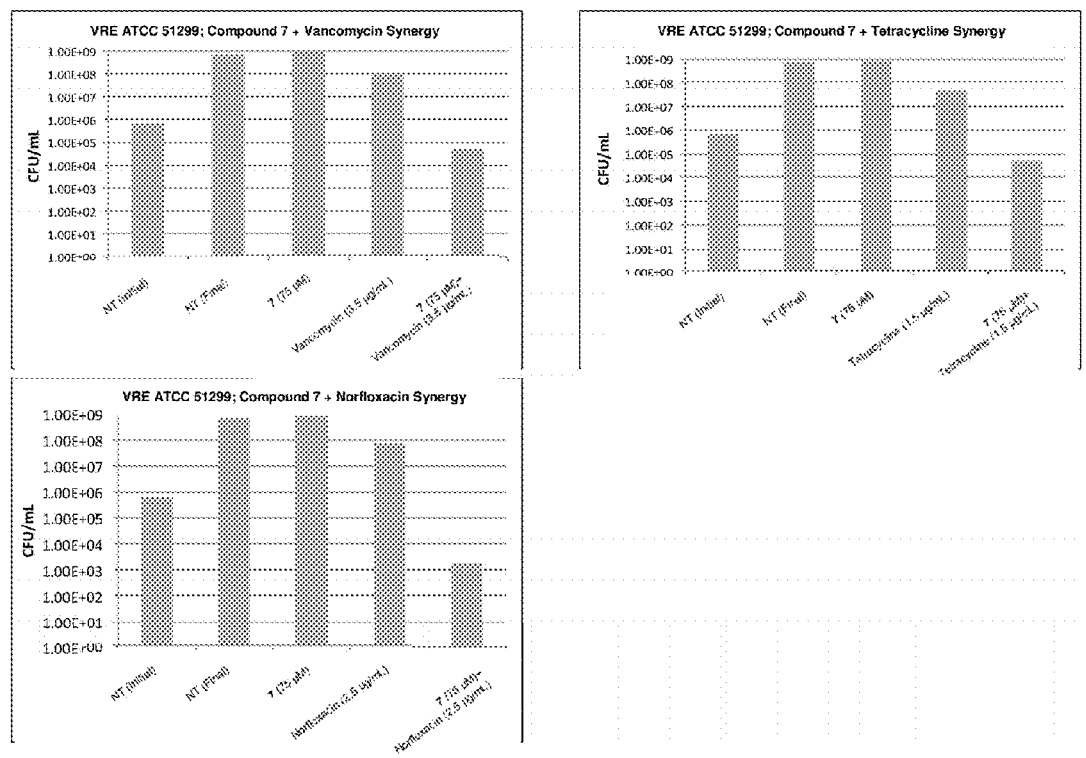
FIG. 42 depicts the synergistic effect of treating VRE with compound 7 with vancomycin, tetracycline or norfloxacin.

FIG. 42 shows that compound 7 was more effective at killing VRE when the cells were treated with 75 μM of compound 7 in conjunction with vancomycin, tetracycline, or norfloxacin compared to treatment with compound 7 or the antibiotics alone.

Figure 43:
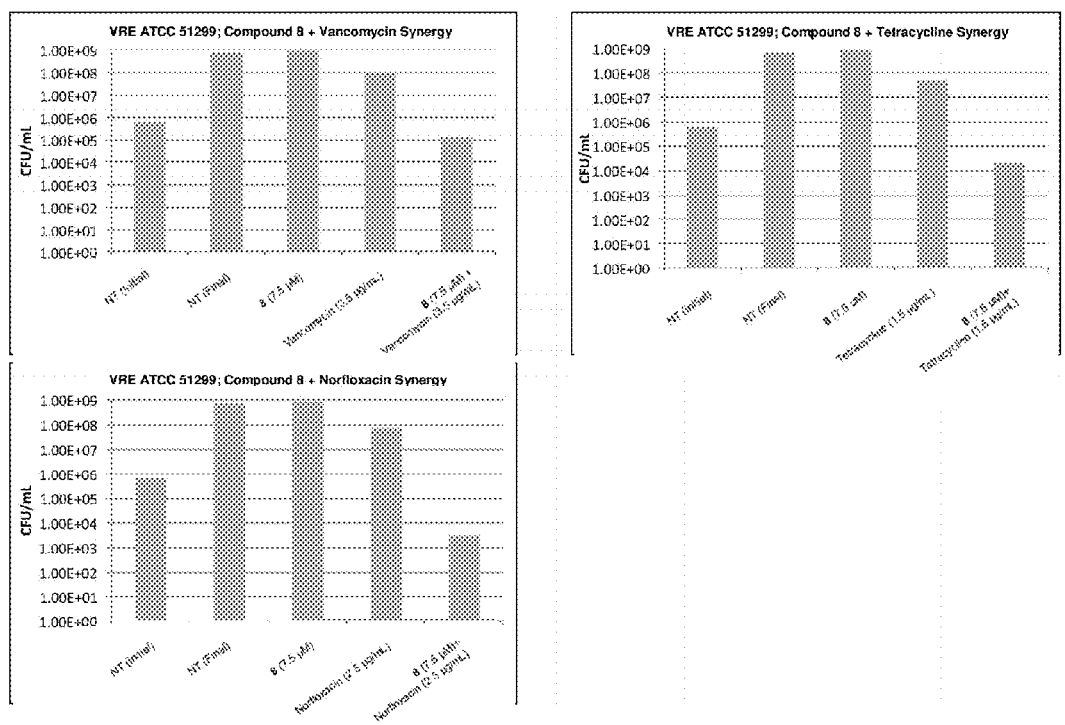
FIG. 43 depicts the synergistic effect of treating VRE with compound 8 with vancomycin, tetracycline or norfloxacin.

FIG. 43 shows that compound 8 was more effective at killing VRE when the cells were treated with 7.5 μM of compound 8 in conjunction with vancomycin, tetracycline, or norfloxacin compared to when the cells were treated with compound 8 or the antibiotics alone.

Figure 44:
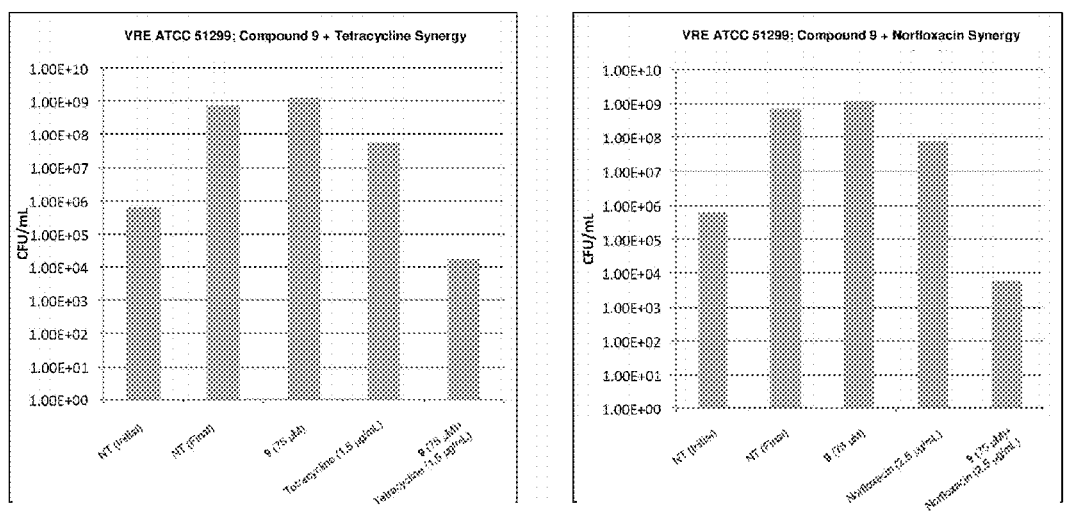
FIG. 44 depicts the synergistic effect of treating VRE with compound 9 with tetracycline or norfloxacin.

FIG. 44 shows that compound 9 was more effective at killing VRE when the cells were treated with 75 μM of compound 9 in conjunction with tetracycline or norfloxacin compared to treatment with compound 9 or the antibiotics alone.

Figure 45:
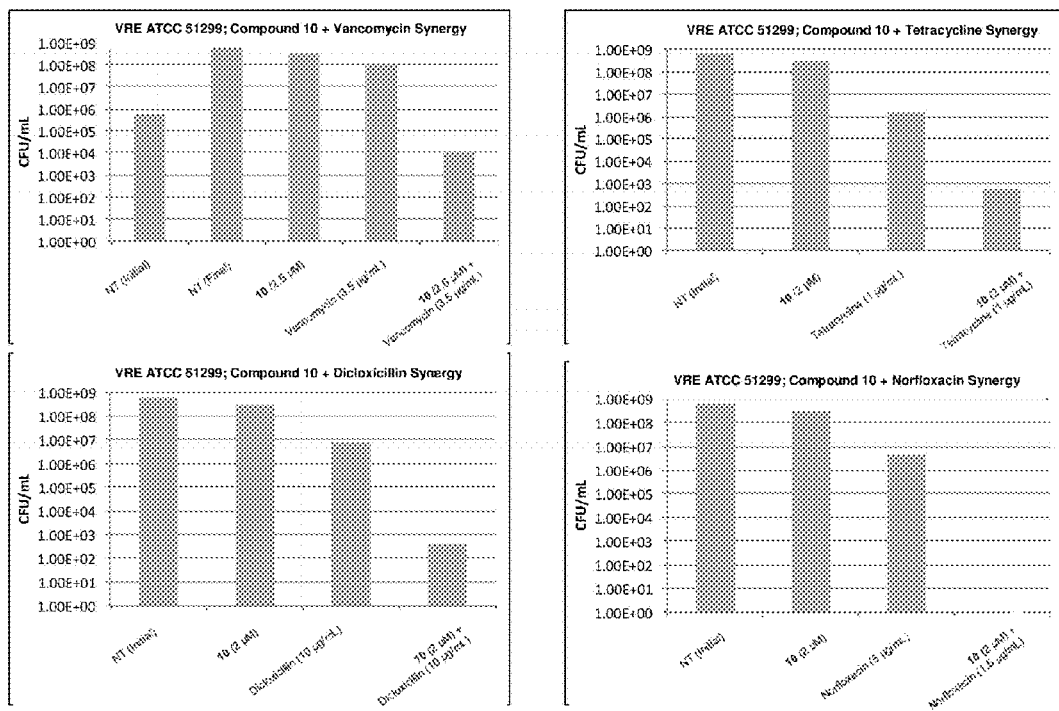
FIG. 45 depicts the synergistic effect of treating VRE with compound 10 with vancomycin, tetracycline, dicloxicillin or norfloxacin.

FIG. 45 shows that compound 10 was more effective at killing VRE when the cells were treated with 2-2.5 μM of compound 10 in conjunction with vancomycin, tetracycline, dicloxicillin, or norfloxacin compared to treatment with compound 10 or the antibiotics alone.

Figure 46:
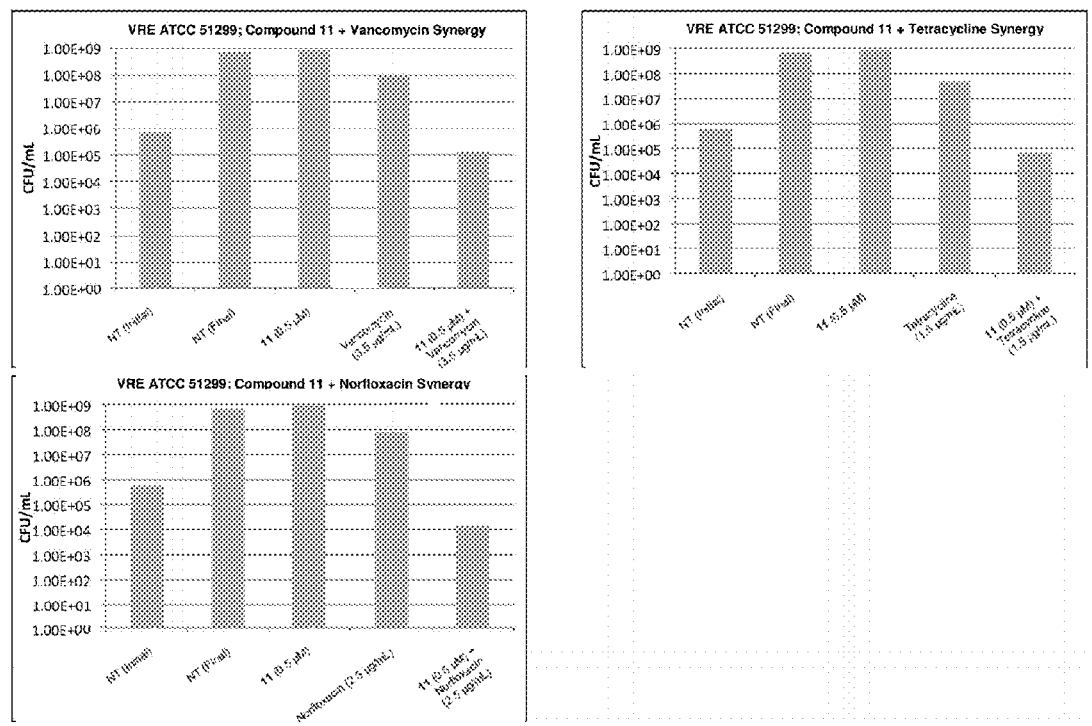
FIG. 46 depicts the synergistic effect of treating VRE with compound 11 with vancomycin, tetracycline or norfloxacin.

FIG. 46 shows that compound 11 was more effective at killing VRE when the cells were treated with 2-2.5 μM of compound 11 in conjunction with vancomycin, tetracycline, or norfloxacin compared to treatment with compound 11 or the antibiotics alone.

TABLE 24 details the MICs of common antibiotics against VRE. In a 12×75 mm borosilicate glass culture tube, 1 mL of cell suspension was added. Then, compound 7 was added to the cells, and the samples were mixed using a vortex mixer. Then, vancomycin (4 μg/mL), norfloxacin (4 μg/mL), tetracycline (4 μg/mL), or gentamycin (4 μg/mL) were added, and the samples were mixed using a vortex mixer. The samples were incubated overnight at 37° C. on a rotary shaking incubator at 100 rpm. Inhibition observed visually compared to each individual treatment was considered synergistic.

The results in TABLE 24 show that in VRE, Compound 7 potentiates the activity of vancomycin. In VRE, which is penicillin G-, ampicillin-, tetracycline- and norfloxacin-sensitive, compound 7 synergizes with vancomycin at a concentration of 4 ug/ml (CLSI vancomycin in vitro susceptibility breakpoint: ≤2 μg/mL). S stands for 'sensitive' and R stands for 'resistant'.

TABLE 24

| Antibiotic | MIC | S/R |
|---|---|---|
| Penicillin G | 2 μg/mL | S |
| Ampicilin | 2-4 μg/mL | S |
| Vancomycin | 64 μg/mL | R |
| Erythromycin | >32 μg/mL | R |
| Tetracycline | <0.5 μg/mL | S |
| Norfloxacin | 1 μg/mL | S |

Example 21: Synergy of Compounds 7-11 with Antibiotics Against Gram-Negative *Klebsiella Pneumoniae* Using PMB The MICs of PMB and compounds 7-11 were determined against *Klebsiella pneumoniae* (CRE, ATCC BAA-1705). Based on the MIC determinations, a sub-inhibitory concentration of PMB (200 ng/mL) was added to the cell suspensions, and the samples were incubated for 3 hours. After the incubation with PMB, each of the compounds was added at a concentration of 20 μM, and the samples were incubated for an additional 18 hours. A sample was taken and diluted ten-fold in media. Ten microliters of each dilution was then drip-streaked onto an agar plate and incubated overnight at 37° C. Colony counts were then performed and the concentrations of cells (CFU/mL) were calculated.

Figure 47:
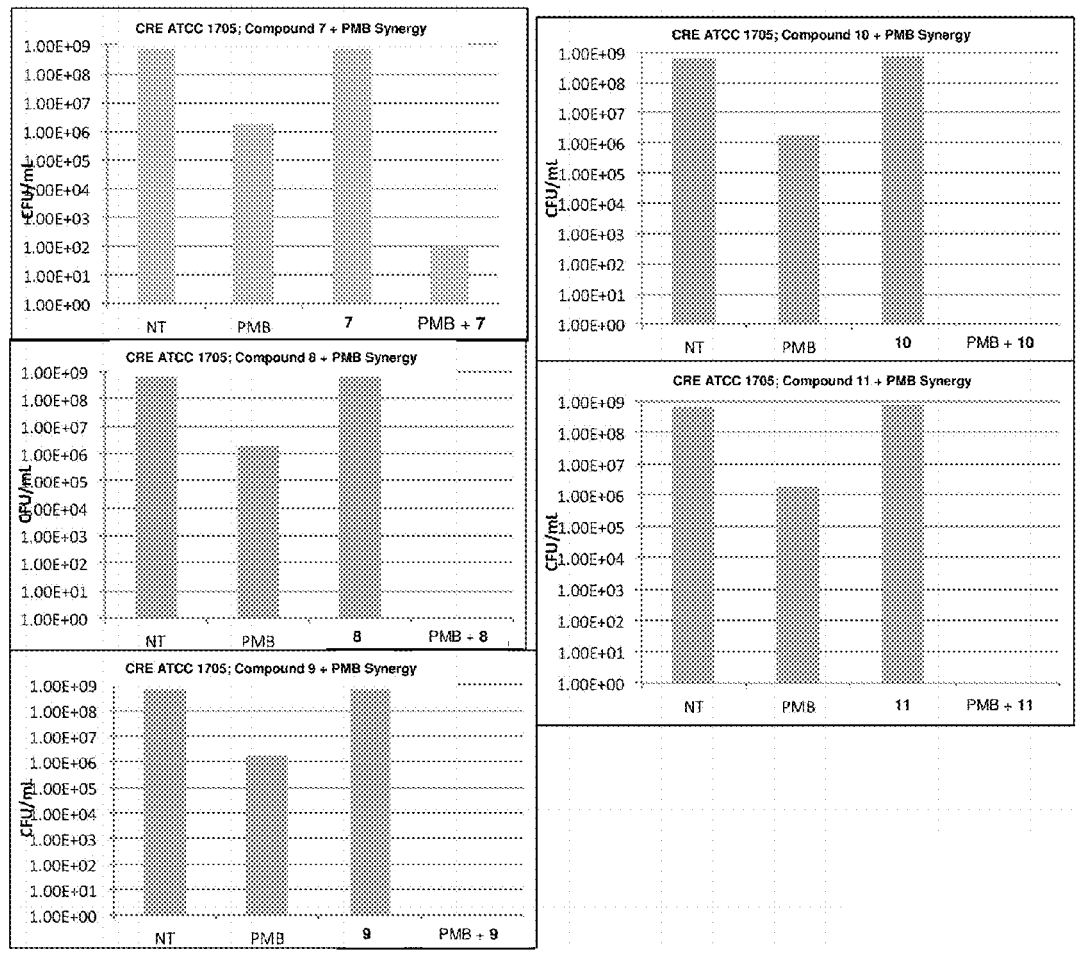
FIG. 47 depicts the synergistic effect of treating CRE with compounds 7-11 with Polymyxin B.

FIG. 47 shows the synergy of compounds 7-11 with PMB against CRE. When used with PMB, compound 7 substantially reduced the number of CRE colonies. Simultaneous treatment of cells with PMB and compounds 8-11 resulted in significant antibacterial activity and reduced the bacterial population to sterility.

Example 22: Synergy of Compound 7 with Antibiotics Against Gram-Negative E. cloacae and K. Pneumoniae Using PMB and PME TABLE 25 details the MICs of PMB and PME against *E. cloacae* and *K. pneumoniae*. The results show that *E. cloacae* and *K. pneumoniae* had identical MICs against PME. In contrast, the MIC of PMB against *K. pneumoniae* was higher than that of *E. cloacae* and had MICs of ≥16 µg/mL and 4 µg/mL, respectively.

TABLE 25

| Antibiotic | E. cloacae ATCC BAA-2341 | K. pneumoniae ATCC BAA-2341 |
| --- | --- | --- |
| PME | 16 µg/mL | 16 µg/mL |
| PMB | 4 µg/mL | ≥16 µg/mL |

TABLE 26 details the combination effects of treating *E. coli*, *E. cloacae*, and *K. pneumoniae* with compound 7 and PMB or PME and the conditions under which the combination effects were determined. The results show that *E. coli* and *K. pneumoniae* exhibited additional inhibition when treated with PMB or PME. *E. cloacae* exhibited additional inhibition when treated with PME.

TABLE 26

| CRE Isolate | Synergy | Conditions |
| --- | --- | --- |
| E. coli ATCC BAA-2340 | Yes | [PMB] = 0.05 µg/mL (Pre-inc. for 2 hrs) + Compound 7 |
| | | [PME] = 0.05 µg/mL (Pre-inc. for 1 hrs) + Compound 7 |
| E. cloacae ATCC BAA-2341 | Yes | [PME] = 0.50 µg/mL (Pre-inc. for 1 hr) + Compound 7 |
| K. pneumoniae ATCC BAA-2342 | Yes | [PMB] = 0.75 µg/mL (Pre-inc. for 2 hrs) + Compound 7 |
| | | [PME] = 0.75 µg/mL (Pre-inc. for 2 hrs) + Compound 7 |

Example 23: Synergy of Compounds 8-11 with Antibiotics Against Gram-Negative *Klebsiella pneumoniae* Using PME TABLE 27 details the individual MIC values of compounds 1, 7, 8, 9, 10, 11, PMB, PME, and light against CRE.

TABLE 27

| Drug | CRE MIC |
| --- | --- |
| Compound 1 | >100 µM |
| Compound 7 | >100 µM |
| Compound 8 | >100 µM |
| Compound 9 | >100 µM |
| Compound 10 | >100 µM |
| Compound 11 | >100 µM |
| PMB | 4 µg/mL |
| PME | 4 µg/mL |
| Light | No effect |

The MICs of PME and compounds 8-11 were determined against *Klebsiella pneumoniae* (CRE, ATCC BAA-1705). Based on the MIC determinations, a sub-inhibitory concentration of PME (200 ng/mL) was added to the cell suspensions, and the samples were incubated for 1 hour. After the incubation with PME, the compounds were added at a concentration of 20 µM, and the samples were further incubated. At specific time points, the samples were taken and diluted ten-fold in media. Ten microliters of each dilution was then drip-streaked onto an agar plate and incubated overnight at 37° C. Colony counts were then performed and the CFU/mL were calculated.

Figure 48:
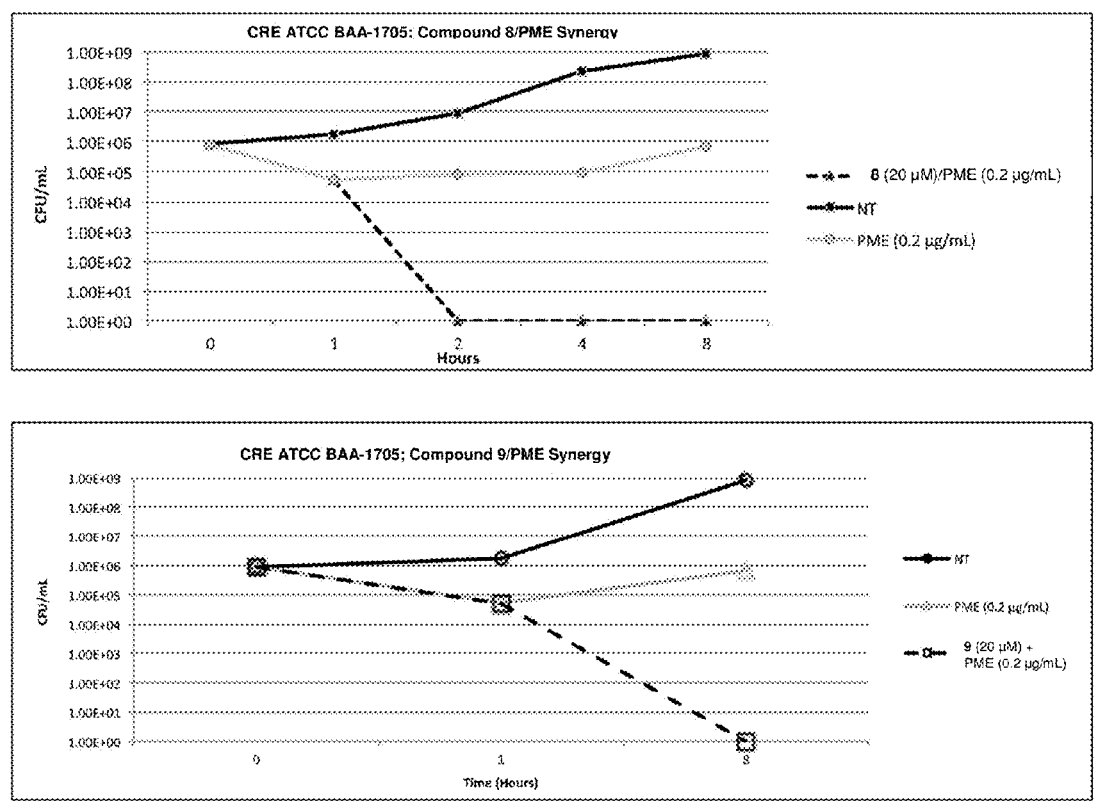
FIG. 48 illustrates the time-dependent effects of treating CRE with compounds 8 or 9 with and without PME.

FIG. 48 shows the time-dependent changes in the colony counts of CRE when the cells were treated with PME, compounds 8 or 9, and PME, or when the cells received no treatment (NT). Both compounds 8 and 9 reduced the CRE colony populations to sterility when the cells were simultaneously treated with PME (0.2 µg/mL). These results demonstrate the synergistic effects of the compounds and PME.

Figure 49:
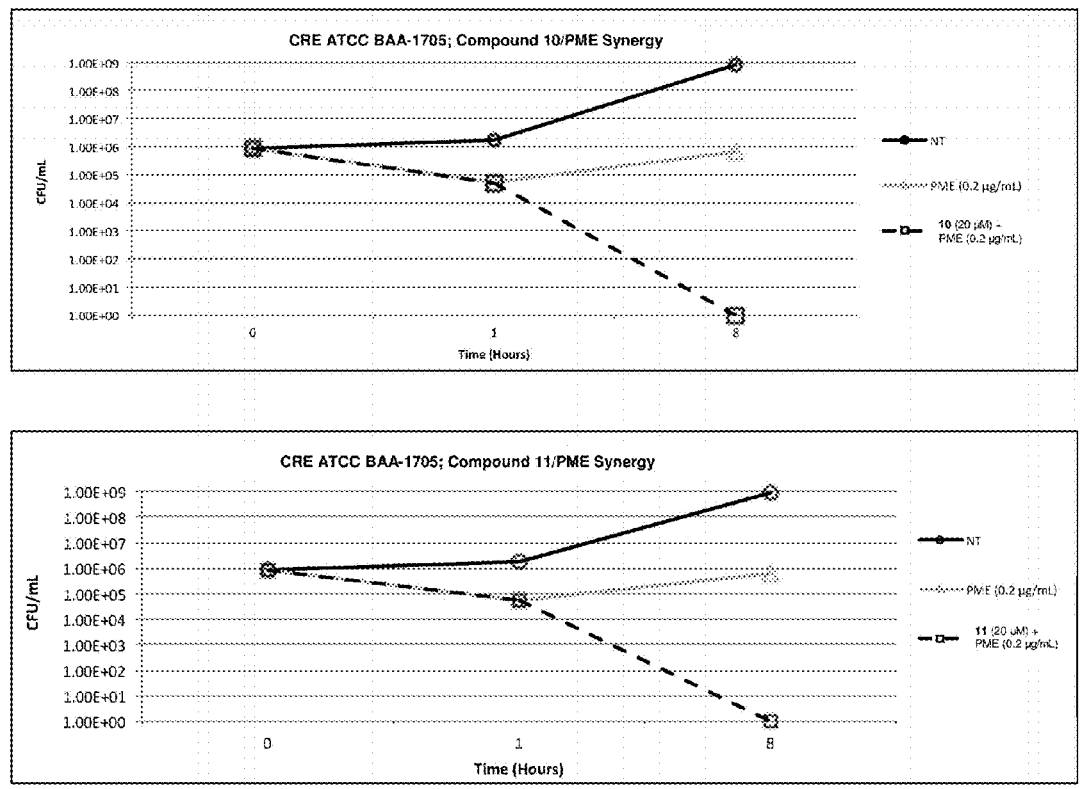
FIG. 49 illustrates the time-dependent effects of treating CRE with compounds 10 or 11 with and without PME.

FIG. 49 shows the time-dependent changes in the colony counts of CRE upon treatment with PME, compounds 10 or 11, and PME, or when the cells received no treatment (NT). Both compounds reduced the CRE colony populations to sterility when the cells were simultaneously treated with PME (0.2 µg/mL). These results demonstrate the synergistic effects of the compounds and PME.

Example 24: Synergy of Compounds 8-11 with Antibiotics Against A. baumannii (ATCC 15151) Using PME TABLE 28 details the individual MIC values of compounds 1, 7, 8, 9, 10, 11, PMB, PME, and light against *A. baumannii*.

TABLE 28

| Drug | A. baumannii MIC |
| --- | --- |
| Compound 1 | >100 µM |
| Compound 7 | >100 µM |
| Compound 8 | >100 µM |
| Compound 9 | >100 µM |
| Compound 10 | >100 µM |
| Compound 11 | >100 µM |
| PMB | 4 µg/mL |
| PME | 0.5 µg/mL |
| Light | No effect |

The MICs of PME and compounds 8-11 were determined against *A. baumannii* (ATCC 15151). Based on the MIC determinations, a sub-inhibitory concentration of PME (200 ng/mL) was added to the cell suspensions, and the resulting samples were incubated for 1 hour. After incubating the cells with PME, a compound (5 µM) was added, and the samples were further incubated at 37° C. At specific time points, samples were taken and diluted ten-fold in media. Ten microliters of each dilution was then drip-streaked onto an agar plate and incubated overnight at 37° C. Colony counts were then performed, and the CFU/mL were calculated.

Figure 50:
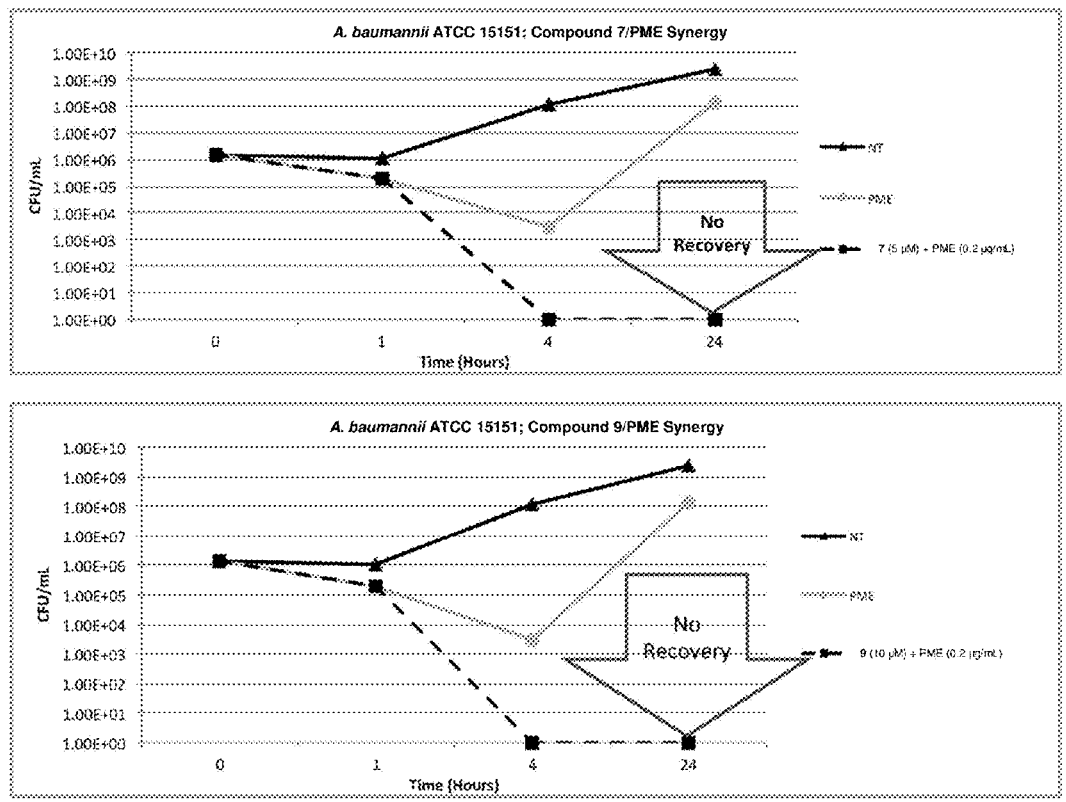
FIG. 50 illustrates changes in MICs of compounds 7 and 9 over time against *A. baumannii* in the presence and absence of PME.

FIG. 50 shows the MICs of compounds 7 and 9 for several time points. When the bacterial colonies were treated with compounds 7 or 9 along with 0.2 µg/mL of PME, the *A. baumannii* colony populations were reduced to sterility. The arrows indicate that the bacterial colonies did not recover with time upon being treated with compounds 7 or 9 and PME.

Figure 51:
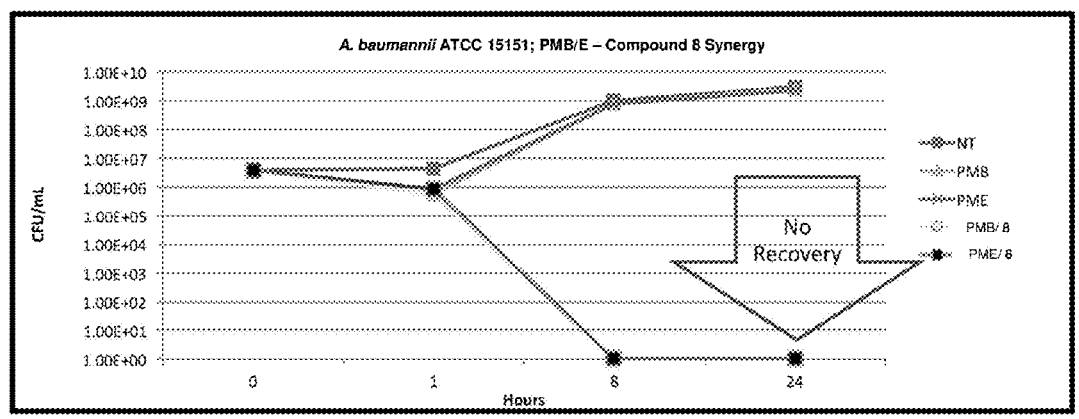
FIG. 51 illustrates changes in MIC of compound 8 over time against *A. baumannii* in the presence and absence of PME and PMB.

FIG. 51 shows the MIC of compound 8 for several time points. When the bacterial colonies were treated with compound 8 along with PME or PMB, the *A. baumannii* colony populations were reduced to sterility. The arrows indicate that the bacterial colonies did not recover with time upon being treated with compound 8 and PME or PMB.

Figure 52:
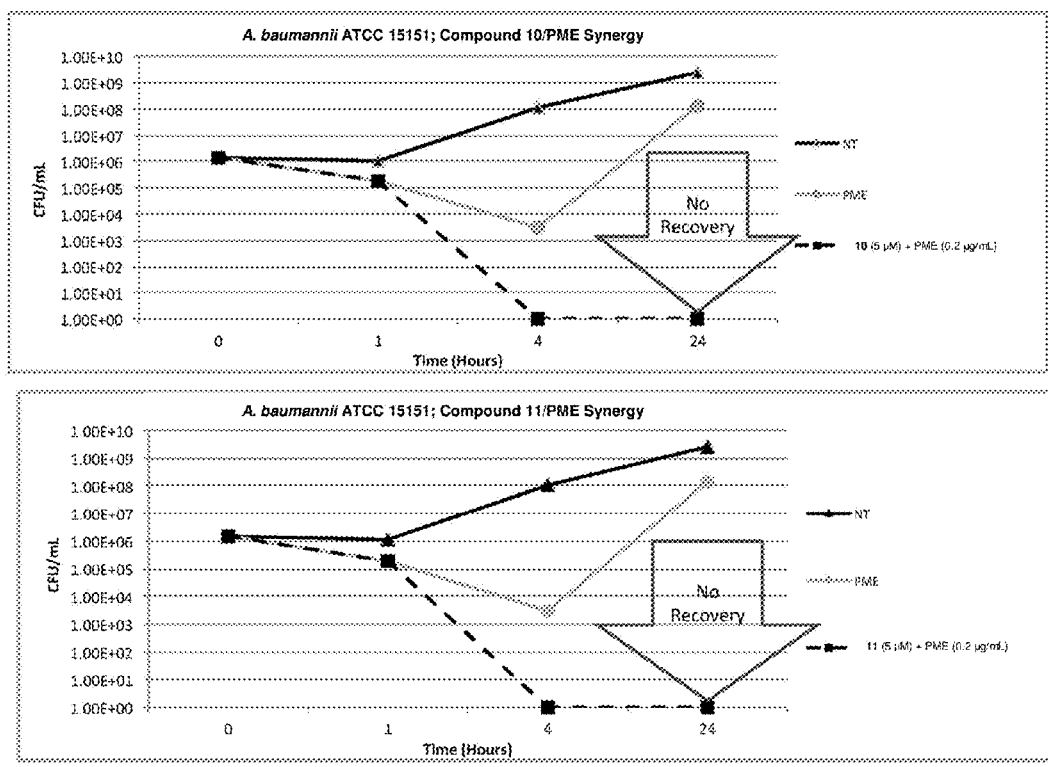
FIG. 52 illustrates changes in MICs of compounds 10 and 11 over time against *A. baumannii* in the presence and absence of PME.

FIG. 52 shows the MICs of compounds 10 and 11 for several time points. When the bacterial colonies were treated with compounds 10 or 11 along with 0.2 μg/mL of PME, the *A. baumannii* colony populations were reduced to sterility. The arrows indicate that the bacterial colonies did not recover with time upon being treated with compounds 10 or 11 and PME.

Example 25: Resensitization of Pathogenic Bacteria to Antibiotics in the Presence of Compound 1 and Compounds 7-11

The data in TABLE 29 demonstrate that the compounds of the invention resensitized pathogenic drug-resistant bacteria to antibiotics. The column on the right shows the order-of-magnitude increase in killing efficacy when the compounds were co-administered with an antibiotic, as compared to the more active of either of the components alone.

The combination effects of compound 1 and compounds 7-11 were quantified in the presence of antibiotics, including PMB, PME, oxacillin, norfloxacin, vancomycin, tetracycline, dicloxacillin, tobramycin, doxycycline, and/or light. In a 96-well microtiter plate, two-fold dilutions were made of each drug (starting with 100 μM) in 100 μL of a cell suspension in TSB. The resulting samples were incubated overnight at 37° C. on a rotary shaking incubator at 100 rpm. The samples were then visually inspected for turbidity. A 20% well volume of MTT reagent (5 mg/mL) was subsequently added, and the samples were incubated for about 20 minutes. The MICs of the compounds of the invention were determined as the concentrations at which full visual inhibition was observed.

TABLE 29

| Compound | Organism | Antibiotic/Second Drug Substance | Log Reduction |
| --- | --- | --- | --- |
| 1 (1 μM) | *E. Coli* | PMB (0.1 μg/mL) | 4 |
| 1 (1 μM) | *E. Coli* | PMB (0.1 μg/mL) + Light (2 min) | 7 |
| 1 (1 μM) | MRSA ATCC BAA-44 | Light (2 min) | 8 |
| 1 (1 μM) | MRSA ATCC BAA-1717 | Light (2 min) | 6 |
| 1 (1 μM) | *S. aureus* ATCC 29213 | Light (2 min) | 6 |
| 1 (1 μM) | VRE | Light (2 min) | 8-9 |
| 1 (1 μM) | *S. pyogenes* ATCC 8133 | Light (2 min) | 6-7 |
| 1 (1 μM) | *S. mutans* Ward's 85W 2357 | Light (2 min) | 5-6 |
| 1 (5 μM) | *A. baumannii* | PMB (0.5 μg/mL) | 8 |
| 1 (5 μM) | *A. baumannii* | PME (0.2 μg/mL) | 8 |
| 1 (5 μM) | CRE | PMB (0.2 μg/mL) + Light (2 min) | 3 |
| 1 (5 μM) | *S. aureus* ATCC 29213 | Tetracycline (0.1 μg/mL) | 5 |
| 1 (5 μM) | *S. aureus* ATCC 29213 | Norfloxacin (0.5 μg/mL) | 6 |
| 1 (10 μM) | MRSA | Vancomycin (0.5 μg/mL) | 9 |
| 1 (10 μM) | MRSA | Tetracycline (0.1 μg/mL) | 5-6 |
| 1 (10 μM) | MRSA | Doxycycline (0.1 μg/mL) | 4 |
| 1 (10 μM) | MRSA | Norfloxacin (20 μg/mL) | 9 |
| 1 (10 μM) | MRSA | Oxacillin (100 μg/mL) | 7-8 |
| 1 (10 μM) | MRSA | Dicloxacillin (1 μg/mL) | 8 |
| 1 (10 μM) | MRSA | Tobramycin (100 μg/mL) | 9 |
| 1 (10 μM) | CRE | PME (0.1 μg/mL) | 9 |
| 1 (10 μM) | CRE | PME (0.2 μg/mL) + Light (2 min) | 9 |
| 1 (20 μM) | *P. aeruginosa* | PME (0.1 μg/mL) | 2 |
| 1 (20 μM) | *P. aeruginosa* | PME (0.1 μg/mL) + Light (2 min) | 8 |
| 7 (5 μM) | *A. baumannii* | PME (0.2 μg/mL) | 8 |
| 7 (15 μM) | MRSA | Oxacillin (100 μg/mL) | 6 |
| 7 (15 μM) | MRSA | Norfloxacin (15 μg/mL) | 4 |
| 7 (15 μM) | MRSA | Oxacillin (100 μg/mL) | 6 |
| 7 (15 μM) | MRSA | Norfloxacin (15 μg/mL) | 4 |
| 7 (20 μM) | *P. aeruginosa* | PME (0.1 μg/mL) | 3 |
| 7 (20 μM) | CRE | PMB (0.2 μg/mL) | 4 |
| 7 (75 μM) | VRE | Norfloxacin (2.5 μg/mL) | 4-5 |
| 7 (75 μM) | VRE | Vancomycin (3.5 μg/mL) | 3-4 |
| 7 (75 μM) | VRE | Tetracycline (1.5 μg/mL) | 3 |
| 8 (5 μM) | MRSA | Oxacillin (50 μg/mL) | 3-4 |
| 8 (5 μM) | MRSA | Norfloxacin (25 μg/mL) | 2-3 |
| 8 (5 μM) | *A. baumannii* | PME (0.05 μg/mL) | 9 |
| 8 (7.5 μM) | VRE | Norfloxacin (2.5 μg/mL) | 4-5 |
| 8 (7.5 μM) | VRE | Vancomycin (3.5 μg/mL) | 3 |
| 8 (7.5 μM) | VRE | Tetracycline (1.5 μg/mL) | 3-4 |
| 8 (20 μM) | CRE | PMB (0.2 μg/mL) | 6 |
| 8 (20 μM) | CRE | PME (0.2 μg/mL) | 6 |
| 8 (20 μM) | *A. baumannii* | PMB (0.2 μg/mL) | 9 |
| 8 (20 μM) | *P. aeruginosa* | PME (0.1 μg/mL) | 4 |
| 9 (5 μM) | *A. baumannii* | PME (0.2 μg/mL) | 8 |
| 9 (8 μM) | MRSA | Oxacillin (125 μg/mL) | 2-3 |
| 9 (8 μM) | MRSA | Norfloxacin (25 μg/mL) | 2-3 |
| 9 (20 μM) | CRE | PMB (0.2 μg/mL) | 6 |

TABLE 29-continued

| Compound | Organism | Antibiotic/Second Drug Substance | Log Reduction |
|---|---|---|---|
| 9 (20 μM) | CRE | PME (0.2 μg/mL) | 6 |
| 9 (20 μM) | P. aeruginosa | PME (0.1 μg/mL) | 2 |
| 9 (75 μM) | VRE | Norfloxacin (2.5 μg/mL) | 4 |
| 9 (75 μM) | VRE | Tetracycline (1.5 μg/mL) | 3-4 |
| 10 (1 μM) | MRSA | Oxacillin (100 μg/mL) | 4-5 |
| 10 (1 μM) | MRSA | Norfloxacin (15 μg/mL) | 5-6 |
| 10 (2 μM) | VRE | Norfloxacin (5 μg/mL) | 5-6 |
| 10 (2 μM) | VRE | Tetracycline (1 μg/mL) | 3-4 |
| 10 (2 μM) | VRE | Dicloxacillin (10 μg/mL) | 5 |
| 10 (2.5 μM) | VRE | Vancomycin (3.5 μg/mL) | 4 |
| 10 (5 μM) | A. baumannii | PME (0.2 μg/mL) | 8 |
| 10 (20 μM) | CRE | PME (0.2 μg/mL) | 6 |
| 10 (20 μM) | CRE | PME (0.2 μg/mL) | 6 |
| 10 (20 μM) | P. aeruginosa | PME (0.1 μg/mL) | 2 |
| 11 (0.5 μM) | MRSA | Oxacillin (100 μg/mL) | 5 |
| 11 (0.5 μM) | MRSA | Norfloxacin (20 μg/mL) | 8 |
| 11 (0.5 μM) | VRE | Norfloxacin (2.5 μg/mL) | 3-4 |
| 11 (0.5 μM) | VRE | Vancomycin (3.5 μg/mL) | 3 |
| 11 (0.5 μM) | VRE | Tetracycline (1.5 μg/mL) | 3 |
| 11 (5 μM) | A. baumannii | PME (0.2 μg/mL) | 8 |
| 11 (20 μM) | CRE | PME (0.2 μg/mL) | 6 |
| 11 (20 μM) | CRE | PME (0.2 μg/mL) | 6 |
| 11 (20 μM) | P. aeruginosa | PME (0.1 μg/mL) | 2 |

Example 26: Synergistic Effects of Treating MRSA Isolates with Compounds 7-11 and Antibiotics TABLES 30-40 show the combination effects of treating various strains of S. aureus (i.e., ATCC 33591, BAA-44; BAA-1707; BAA-1717; BAA-1720; BAA-1747; BAA-1754; BAA-1761; BAA-1763; BAA-1764; BAA-1766) with compounds 7-11 and an antibiotic (i.e., oxacillin, norfloxacin, tetracycline, gentamycin, and vancomycin). The results in TABLES 30-40 show that compounds 7-11 were more effective at killing MRSA isolates when used in conjunction with an antibiotic.

Inhibition resulting from co-treatment of a broth suspension with a compound of the invention and an antibiotic was compared to broth suspensions subjected to each individual treatment. A visual observation of inhibition with the unaided eye upon co-treatment of the broth suspensions, based on turbidity, was considered synergistic. The MICs were read as the lowest concentration of an antimicrobial agent that completely inhibited growth of the organism in the tubes or microdilution wells as detected by the unaided eye.

Exceptions to reading complete inhibition of growth included Gram-positive cocci. For Gram-positive cocci, trailing growth was observed. For these species, the MICs were read at the first spot where trailing was observed, and tiny buttons of growth were ignored.

Exceptions to reading complete inhibition of growth also included trimethoprim and sulfonamides. Antagonists in the medium allowed for some slight growth; thus, the end point was read as the concentration in which there was ≥80% reduction in growth compared to the control. When a single skipped well (i.e., wells that exhibit no growth although growth occurs at higher concentrations) was observed, the highest MIC was read.

A compound of the invention and an antibiotic were considered to have "no synergy" when no change was observed in turbidity between co-treatment of a broth suspension with a compound of the invention and an antibiotic and either of the individual components alone.

MIC interpretive standards were used to classify antibiotics, including oxacillin, norfloxacin, gentamycin, vancomycin, and tetracycline, as "susceptible", "intermediate", or "resistant". Two-fold dilutions of the antibiotics were prepared in a liquid growth medium dispensed in test tubes. For broth dilutions, cation-adjusted Mueller-Hinton broth was used to determine the MICs; cation-adjusted Mueller-Hinton broth supplemented with 2% NaCl was used to determine the MIC of oxacillin. For agar dilutions, Mueller-Hinton agar was used to determine the MICs; Mueller-Hinton agar supplemented with 2% NaCl was used to determine the MIC of oxacillin. The antibiotic-containing tubes were inoculated with a standard bacterial suspension of 5×10$^5$ CFU/mL. Following an overnight incubation (16-20 hrs) at 35±2° C. under ambient air, the tubes were examined for visible bacterial growth based on turbidity. The lowest concentration of antibiotic that prevented growth was determined to be the MIC. An incubation time of 24 hrs was used to determine the MICs of oxacillin and vancomycin.

TABLE 30

MRSA ATCC BAA-1707

| Compound | Oxacillin | Norfloxacin | Tetracycline | Gentamycin | Vancomycin |
|---|---|---|---|---|---|
| 7 | Susceptible | Susceptible | Synergy | Susceptible | Susceptible |
| 8 | Susceptible | Susceptible | No Synergy | Susceptible | Susceptible |
| 9 | Susceptible | Susceptible | No Synergy | Susceptible | Susceptible |
| 10 | Susceptible | Susceptible | Synergy | Susceptible | Susceptible |
| 11 | Susceptible | Susceptible | Synergy | Susceptible | Susceptible |

TABLE 31

MRSA ATCC BAA-1717 Results

| Compound | Oxacillin | Norfloxacin | Tetracycline | Gentamycin | Vancomycin |
|---|---|---|---|---|---|
| 7 | Synergy | Susceptible | Susceptible | Susceptible | Susceptible |
| 8 | Synergy | Susceptible | Susceptible | Susceptible | Susceptible |
| 9 | Synergy | Susceptible | Susceptible | Susceptible | Susceptible |
| 10 | Synergy | Susceptible | Susceptible | Susceptible | Susceptible |
| 11 | Synergy | Susceptible | Susceptible | Susceptible | Susceptible |

TABLE 32

MRSA ATCC BAA-1720 Results

| Compound | Oxacillin | Norfloxacin | Tetracycline | Gentamycin | Vancomycin |
|---|---|---|---|---|---|
| 7 | Synergy | No Synergy | Susceptible | Susceptible | Susceptible |
| 8 | Synergy | No Synergy | Susceptible | Susceptible | Susceptible |
| 9 | Synergy | No Synergy | Susceptible | Susceptible | Susceptible |
| 10 | No Synergy | No Synergy | Susceptible | Susceptible | Susceptible |
| 11 | No Synergy | No Synergy | Susceptible | Susceptible | Susceptible |

TABLE 33

MRSA ATCC BAA-1747 Results

| Compound | Oxacillin | Norfloxacin | Tetracycline | Gentamycin | Vancomycin |
|---|---|---|---|---|---|
| 7 | Susceptible | Susceptible | Susceptible | Susceptible | Susceptible |
| 8 | Susceptible | Susceptible | Susceptible | Susceptible | Susceptible |
| 9 | Susceptible | Susceptible | Susceptible | Susceptible | Susceptible |
| 10 | Susceptible | Susceptible | Susceptible | Susceptible | Susceptible |
| 11 | Susceptible | Susceptible | Susceptible | Susceptible | Susceptible |

TABLE 34

MRSA ATCC BAA-44 Results

| Compound | Oxacillin | Norfloxacin | Tetracycline | Vancomycin |
|---|---|---|---|---|
| 7 | Synergy | No Synergy | Susceptible | Susceptible |
| 8 | No Synergy | No Synergy | Susceptible | Susceptible |
| 9 | No Synergy | No Synergy | Susceptible | Susceptible |
| 10 | No Synergy | No Synergy | Susceptible | Susceptible |
| 11 | Synergy | No Synergy | Susceptible | Susceptible |

TABLE 35

MRSA ATCC 33591 Results

| Compound | Oxacillin | Norfloxacin | Tetracycline | Gentamycin | Vancomycin |
|---|---|---|---|---|---|
| 7 | Synergy | Synergy | Susceptible | Synergy | Susceptible |
| 8 | No Synergy | No Synergy | No Synergy | No Synergy | Susceptible |
| 9 | No Synergy | No Synergy | No Synergy | No Synergy | Susceptible |
| 10 | No Synergy | No Synergy | No Synergy | No Synergy | Susceptible |
| 11 | No Synergy | No Synergy | No Synergy | No Synergy | Susceptible |

TABLE 36

MRSA ATCC BAA-1754 Results

| Compound | Oxacillin | Norfloxacin | Tetracycline | Gentamycin | Vancomycin |
|---|---|---|---|---|---|
| 7 | Synergy | Susceptible | Susceptible | Susceptible | Susceptible |
| 8 | Synergy | Susceptible | Susceptible | Susceptible | Susceptible |
| 9 | No Synergy | Susceptible | Susceptible | Susceptible | Susceptible |
| 10 | No Synergy | Susceptible | Susceptible | Susceptible | Susceptible |
| 11 | No Synergy | Susceptible | Susceptible | Susceptible | Susceptible |

TABLE 37

MRSA ATCC BAA-1761 Results

| Compound | Oxacillin | Norfloxacin | Tetracycline | Gentamycin | Vancomycin |
|---|---|---|---|---|---|
| 7 | Susceptible | No Synergy | Susceptible | Susceptible | Susceptible |
| 8 | Susceptible | No Synergy | Susceptible | Susceptible | Susceptible |
| 9 | Susceptible | No Synergy | Susceptible | Susceptible | Susceptible |
| 10 | Susceptible | No Synergy | Susceptible | Susceptible | Susceptible |
| 11 | Susceptible | No Synergy | Susceptible | Susceptible | Susceptible |

TABLE 38

MRSA ATCC BAA-1763 Results

| Compound | Oxacillin | Norfloxacin | Tetracycline | Gentamycin | Vancomycin |
|---|---|---|---|---|---|
| 7 | Synergy | No Synergy | Susceptible | Susceptible | Susceptible |
| 8 | Synergy | No Synergy | Susceptible | Susceptible | Susceptible |
| 9 | Synergy | No Synergy | Susceptible | Susceptible | Susceptible |
| 10 | No Synergy | No Synergy | Susceptible | Susceptible | Susceptible |
| 11 | No Synergy | No Synergy | Susceptible | Susceptible | Susceptible |

TABLE 39

MRSA ATCC BAA-1764 Results

| Compound | Oxacillin | Norfloxacin | Tetracycline | Gentamycin | Vancomycin |
|---|---|---|---|---|---|
| 7 | Synergy | Susceptible | Susceptible | Susceptible | Susceptible |
| 8 | Synergy | Susceptible | Susceptible | Susceptible | Susceptible |
| 9 | Synergy | Susceptible | Susceptible | Susceptible | Susceptible |
| 10 | No Synergy | Susceptible | Susceptible | Susceptible | Susceptible |
| 11 | No Synergy | Susceptible | Susceptible | Susceptible | Susceptible |

TABLE 40

MRSA ATCC BAA-1766 Results

| Compound | Oxacillin | Norfloxacin | Tetracycline | Gentamycin | Vancomycin |
|---|---|---|---|---|---|
| 7 | Synergy | Susceptible | Susceptible | Susceptible | Susceptible |
| 8 | Synergy | Susceptible | Susceptible | Susceptible | Susceptible |
| 9 | Synergy | Susceptible | Susceptible | Susceptible | Susceptible |
| 10 | No Synergy | Susceptible | Susceptible | Susceptible | Susceptible |
| 11 | No Synergy | Susceptible | Susceptible | Susceptible | Susceptible |

TABLE 41 summarizes the data presented in TABLES 5-17 with respect to compound 7. These data demonstrate that compound 7 reverts a broad spectrum of MRSA strains to antibiotic-sensitive *S. aureus*.

The drug concentrations used to obtain these data were 2.3 μg/mL of compound 7 (⅙ IC$_{50}$ on HeLa cells); 2 μg/mL oxacillin, or 4 μg/mL of norfloxacin, tetracycline, and gentamycin.

TABLE 41

| MRSA Isolate (ATCC) | Oxacillin | Norfloxacin | Tetracycline | Gentamycin |
|---|---|---|---|---|
| 33591 | Synergy | Synergy | — | Synergy |
| BAA-44 | Synergy | No Synergy | — | — |
| BAA-1707 | — | — | Synergy | — |
| BAA-1717 | Synergy | — | — | — |
| BAA-1720 | Synergy | No Synergy | — | — |
| BAA-1747 | — | — | — | — |
| BAA-1754 | Synergy | — | — | — |
| BAA-1761 | — | No Synergy | — | — |
| BAA-1763 | Synergy | No Synergy | — | — |
| BAA-1764 | Synergy | — | — | — |
| BAA-1766 | Synergy | — | — | — |

Figure 53:
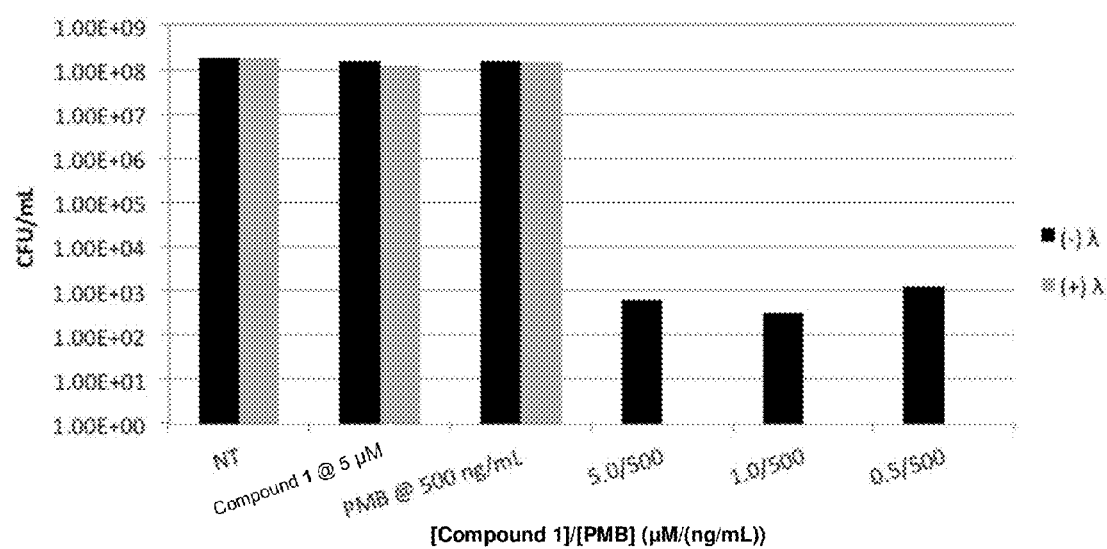
FIG. 53 illustrates the effect of compound 1 and light versus polymyxin B in treatment of *A. baumannii*.

Example 27: Light-Activated Killing of Gram-Negative Organisms with Compound 1 in the Presence of a Non-Toxic Concentration of PMB FIG. 53 is an example of the treatment of *A. baumannii* with compound 1 and PMB at fixed concentrations with and without irradiation using white light (λ). The results indicated that PMB was more efficacious in cell killing when co-administered with compound 1 and light.

Figure 54:
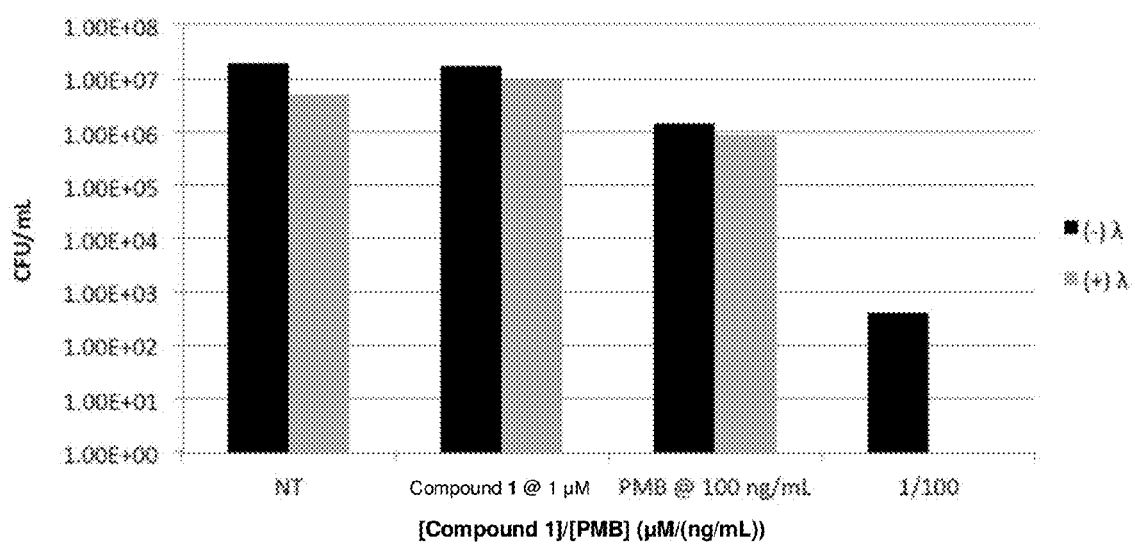
FIG. 54 illustrates the effect of compound 1 and light versus polymyxin B in treatment of *E. coli*.

FIG. 54 is an example of the treatment of *E. coli* with compound 1 and PMB at fixed concentrations with and without irradiation using white light (λ). The results indicated that PMB was more efficacious in cell killing when co-administered with compound 1 and light.

Example 28: Light-Activated Killing of Gram-Negative P. aeruginosa with Compounds of the Invention in the Presence of a Non-Toxic Concentration of PME P. aeruginosa cells were also treated with white light upon being incubated with compound 1 for different durations of time. In a 12×75 mm borosilicate glass culture tube, 1 mL of cell suspension was added. PME was added to the cells, and the samples were mixed using a vortex mixer. The resulting samples were incubated for 1.5 hours at 37° C. on a rotary shaking incubator at 100 rpm. Compound 1 was then added, and the samples were incubated for 30 minutes at 37° C. on a rotary shaking incubator at 100 rpm. The samples were then irradiated with white light using a Lumacare™ LC-122 for 2 minutes (irradiation $\lambda_1$) and incubated overnight at 37° C. The samples were irradiated again with white light using a Lumacare™ LC-122 for 2 minutes (irradiation $\lambda_2$). Ten-fold dilutions were made of each sample, and 10 μL of each dilution was drip-streaked onto an agar plate. The samples were incubated overnight at 37° C., and colony counts were performed to calculate CFU/mL.

Figure 55:
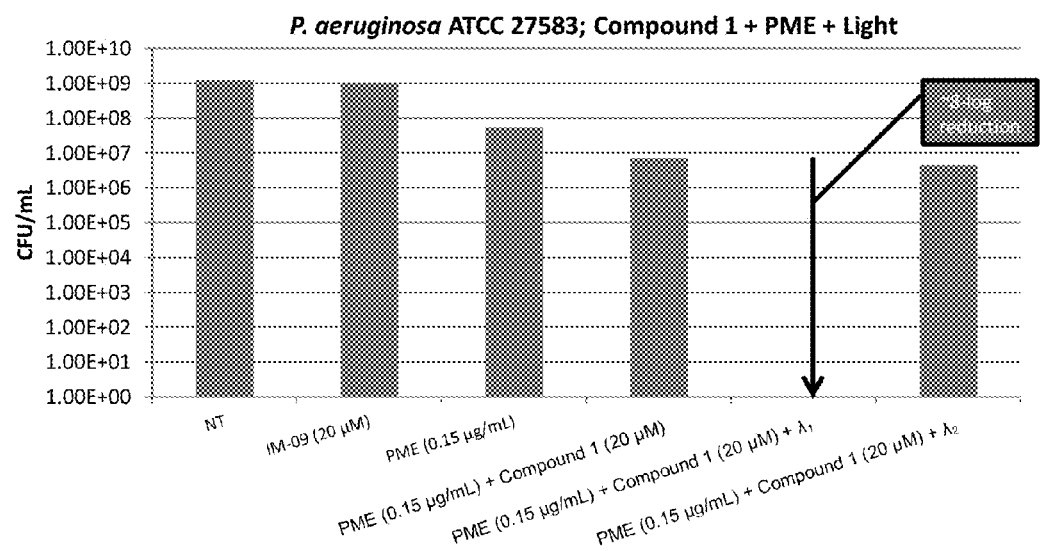
FIG. 55 illustrates the effect of treating *P. aeruginosa* with combinations of compound 1, PME, and light.

FIG. 55 is an illustrative example of the treatment of P. aeruginosa with compound 1, PME, co-treatment with compound 1 and PME, and co-treatment with compound 1, PME, and light ($\lambda_1$ and $\lambda_2$) at fixed concentrations. The results indicated that treatment with light immediately after a 30 minute incubation with compound 1 ($\lambda_1$) resulted in about an 8-log reduction in the CFU/mL compared to cells that received co-treatment with compound 1 and PME. Cells that received treatment with additional irradiation after an overnight incubation with compound 1 ($\lambda_2$) resulted in a negligible reduction in the CFU/mL compared to cells that received co-treatment with compound 1 and PME.

Example 29: Comparison of Compound 1 Administered to HeLa Cells in 0.1% Volume DMSO with Compound 1 Encapsulated in Liposomes To determine if liposomes had an effect on the activity of compound 1, HeLa cells were preincubated either with compound 1 in DMSO or in dipalmitoylphosphatidylcholine (DPPC) liposomes at a 1 μM final concentration of compound 1. An effective period of pre-incubation with the drug in the dark was determined to be about 28 hours for compound 1 in DMSO and 60 hours for liposomal delivery of compound 1. The cells were then irradiated with continuous white light for 2 minutes at a distance of 6.5 cm using a LumaCare™ light source. An MTT assay was carried out to evaluate cell viability 48 hours later.

The results in TABLE 42 indicate that compound 1 was able to kill HeLa cells when in a DMSO solution or encapsulated in liposomes. Additionally, compound 1 in DMSO was more stable at 40° C. compared to the liposomal formulation.

The stability of the formulation was determined using dynamic light scattering (DLS) to measure the mean size and standard deviation, both of which remained consistent. The experiments were repeated after the indicated periods, and the outcome of compound 1 photodynamic therapy was essentially the same in terms of cell killing.

TABLE 42

| Vehicle/ concentration | Compound 1 | Compound 1 + light | Compound 1 pre-incubation to max killing | Stability at 40° C. |
|---|---|---|---|---|
| Compound 1 (1 μM) in DMSO | 6% killing | 77% killing | 28 hours | >2 months |
| Compound 1 (1 μM) in liposomes | 9% killing | 56% killing | 60 hours | >2 weeks |

Example 30: Production of Singlet Oxygen Using a Compound of the Invention

Figure 56:
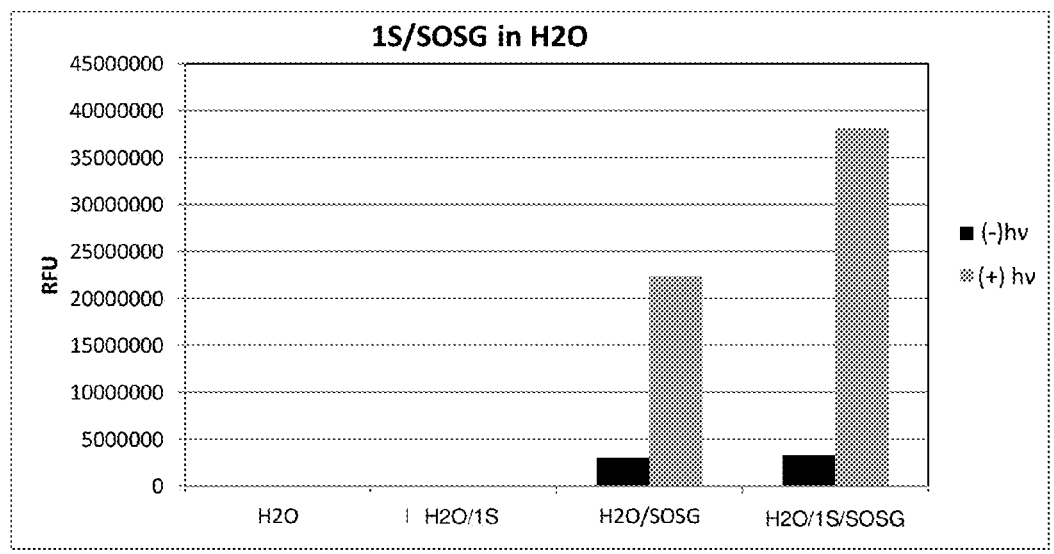
FIG. 56 illustrates production of singlet oxygen using compound 1.

FIG. 56 depicts the ability of a compound of the invention to be a photodynamic agent via the production of singlet oxygen species in vitro. The production of singlet oxygen upon irradiation with light (hv) was detected using Singlet Oxygen Sensor Green (SOSG). 20 μM of each 1-Sol and SOSG were prepared in water and allowed to equilibrate at room temperature for one hour. The samples were read with a UV/Vis plate spectrophotometer using excitation and emission wavelengths of 500 nm and 540 nm, respectively, before and after three minutes of irradiation with non-coherent light (400-700 nm) for three minutes at a 3 cm distance using a Lumacare™ LC-122. The results indicated that the addition of compound 1-Sol increased the production of singlet oxygen as measured by the increase in relative fluorescence units (RFU) of SOSG.

Example 31: Suppression of the Evolution of Resistance in Drug Sensitive S. aureus (ATCC 29213)

The MICs of antibiotics and compounds 7-11 were determined against S. aureus (ATCC 29213). In a 96-well microtiter plate, 100 μL of a cell suspension (about 5×10⁵ CFU/mL in TSB media) were diluted two-fold in triplicate with compounds 7-11 or an antibiotic. Each mixture was incubated at 37° C. on a rotary shaking incubator for about 16 hours. MTT was then added to assess the viability of the cells (at 10% well volume). To evaluate the cells for their evolution of resistance, sub-inhibitory concentrations (0.5 MIC; 0.25 MIC) of each compound and antibiotic were incubated with cells overnight (18-24 hrs) at 37° C. on a rotary shaking incubator at 100 rpm. The cells were then streaked onto a TSA plate and incubated overnight at 37° C. These steps were repeated to reach a total of 30 exposures.

TABLE 43 details the individual MIC values of compounds 1, 7, 8, 9, 10, 11, various antibiotics, and light against S. aureus.

TABLE 43

| Drug | S. aureus MIC |
|---|---|
| Compound 1 | 100 μM |
| Compound 7 | 32 μM |
| Compound 8 | 8 μM |
| Compound 9 | 16 μM |
| Compound 10 | 32-64 μM |
| Compound 11 | 32-64 μM |
| Dicloxicillin | 50-100 μg/mL |
| Doxycycline | 3.12 μg/mL |
| Norfloxacin | 1.25-2.5 μg/mL |
| Oxacillin | 0.5 μg/mL |

TABLE 43-continued

| Drug | S. aureus MIC |
|---|---|
| Tetracycline | 2.5 μg/mL |
| Tobramycin | 0.25 μg/mL |
| Vancomycin | 2 μg/mL |
| Light | No effect |

The ability of S. aureus to develop resistance against compounds 7-11 was tested using oxacillin and norfloxacin as controls. TABLE 22 shows the MIC values for compounds 7-11 and antibiotics (i.e., oxacillin and norfloxacin) after serial passaging at sub-inhibitory concentrations. The results show that no evolution of resistance was observed even after a month of continuous sub-lethal exposure to compounds 7-11. Sensitivity to most compounds remained the same or decreased.

Figure 57:
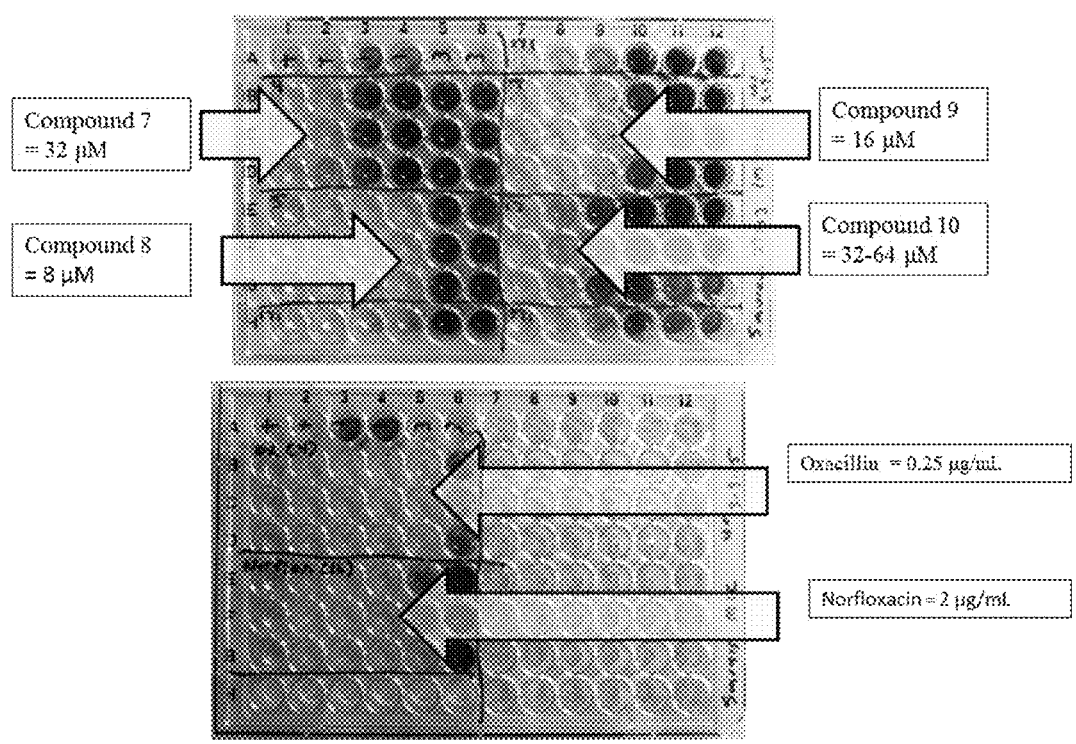
FIG. 57 displays an image of minimum inhibitory concentration measurements of compounds 7-10 against *S. aureus*.
Figure 58:
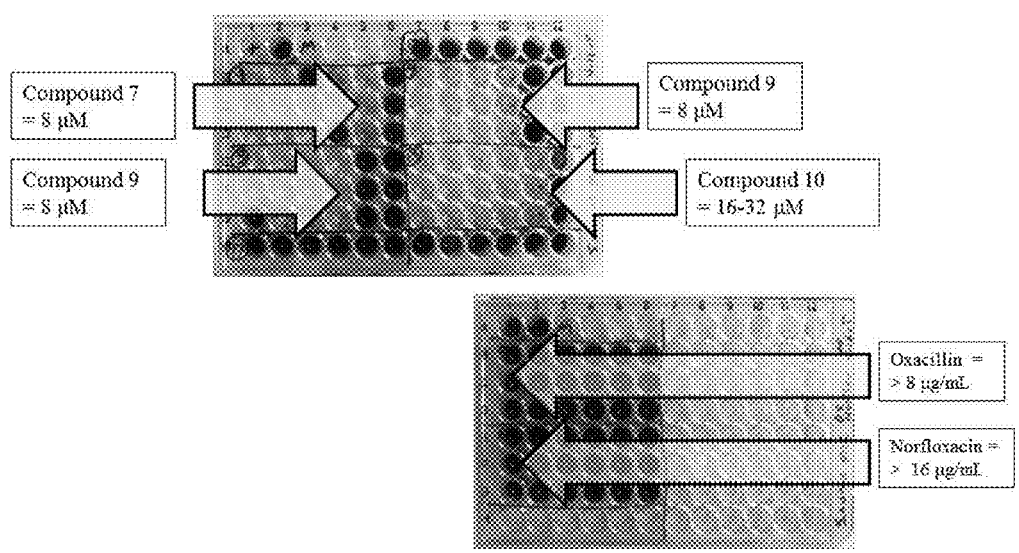
FIG. 58 displays an image of final minimum inhibitory concentration measurements of compounds 7-10 when used to treat *S. aureus* upon receiving 30 exposures.

FIG. 57 and FIG. 58 are the corresponding images to TABLE 44.

TABLE 44

| Compound | Initial MIC (μM) Mar. 10, 2015 | Final MIC (μM) Apr. 16, 2015 | Resistance Evolved |
|---|---|---|---|
| 7 | 32 | 8 | No |
| 8 | 8 | 8 | No |
| 9 | 16 | 8 | No |
| 10 | 32-64 | 16-32 | No |
| 11 | 32-64 | >256 | Yes |
| Oxacillin | 0.25 | >8 | Yes |
| Norfloxacin | 2 | >16 | Yes |

Example 32: Summary of the Synergistic Activities of Compounds of the Invention TABLE 45 summarizes the synergistic activities of the seven classes of clinically used antibiotics and compounds of the invention against a variety of different drug-resistant bacteria.

TABLE 45

| Bacterial Isolate | β-lactama Oxacillin | Fluoroquinolones Norfloxacin | Glycopeptides Vancomycin | Tetracyclines Tetracycline | Aminoglycosides Gentamycin | Macrolides Erythromycin | Polypeptides Polymyxin E | Polymyxin B |
|---|---|---|---|---|---|---|---|---|
| MRSA ATCC 33591 | Synergy (7) | Synergy (7) | — | — | Synergy (7) | — | — | — |
| MRSA ATCC BAA-44 | Synergy* (7, 8, 9, 10 and 11) | Synergy (7, 8, 9, 10 and 11) | Synergy (7) | Synergy† (1) | Synergy‡ (7) | Synergy (1) | — | — |
| MRSA ATCC BAA-1707 | — | — | — | Synergy (7) | — | — | — | — |
| MRSA ATCC BAA-1717 | Synergy (7) | — | — | — | — | — | — | — |
| MRSA ATCC BAA-1720 | Synergy (7) | — | — | — | — | — | — | — |
| MRSA ATCC BAA-1747 | Synergy (7) | — | — | — | — | — | — | — |
| MRSA ATCC BAA-1754 | Synergy (7) | — | — | — | — | — | — | — |
| MRSA ATCC BAA-1761 | — | — | — | — | — | — | — | — |
| MRSA ATCC BAA-1763 | Synergy (7) | — | — | — | — | — | — | — |
| MRSA ATCC BAA-1764 | Synergy (7) | — | — | — | — | — | — | — |
| MRSA ATCC BAA-1766 | Synergy (7) | — | — | — | — | — | — | — |
| VRE ATCC 51299 | Synergy (10: dicloxicillin) | Synergy (7, 8, 9, 10 and 11) | Synergy (7, 8, 9, 10 and 11) | Synergy (7, 8, 9, 10 and 11) | — | — | — | — |
| P. aeruginosa ATCC 27853 | — | — | — | — | — | — | Synergy (7, 8, 9, 10 and 11) | Synergy (7, 8, 9, 10 and 11) |
| CRE ATCC 1705 | — | — | — | — | — | — | Synergy (7, 8, 9, 10 and 11) | Synergy (7, 8, 9, 10 and 11) |
| CRE ATCC 2340 | — | — | — | — | — | — | Synergy (7, 8, 9, 10 and 11) | Synergy (7, 8, 9, 10 and 11) |
| CRE ATCC 2341 | — | — | — | — | — | — | Synergy (7, 8, 9, 10 and 11) | Synergy (7, 8, 9, 10 and 11) |
| CRE ATCC 2342 | — | — | — | — | — | — | Synergy (7, 8, 9, 10 and 11) | Synergy (7, 8, 9, 10 and 11) |
| A. baumannii ATCC 15151 | — | — | — | — | — | — | Synergy (7, 8, 9, 10 and 11) | Synergy Synergy (7, 8, 9, 10 and 11)) |

*indicated ampicillin, dicloxicillin and Penicillin G;
†includes doxycycline;
‡includes tobramycin
"—" indicates either existing synergy or TBD

EMBODIMENTS

The following non-limiting embodiments provide illustrative examples of the invention, but do not limit the scope of the invention.

Embodiment 1

A method of treating a condition, the method comprising administering to a subject in need thereof a therapeutically-effective amount of a compound that binds a biological structure, thereby decreasing drug resistance in a cell, wherein the compound is more therapeutically-effective in the presence of light than in the dark.

Embodiment 2

The method of embodiment 1, wherein the subject is human.

Embodiment 3

The method of any one of embodiments 1-2, further comprising irradiating the compound after administration to the subject.

Embodiment 4

The method of embodiment 3, wherein the compound is irradiated with light having a wavelength of about 200 to about 800 nm.

Embodiment 5

The method of any one of embodiments 1-4, wherein the condition is caused by a microbe.

Embodiment 6

The method of embodiment 5, wherein the microbe is a bacterium.

Embodiment 7

The method of embodiment 5, wherein the microbe is a Gram-positive bacterium.

Embodiment 8

The method of embodiment 5, wherein the microbe is a Gram-negative bacterium.

Embodiment 9

The method of embodiment 5, wherein the microbe is a drug-resistant bacterium.

Embodiment 10

The method of embodiment 5, wherein the microbe is methicillin-resistant *Staphylococcus aureus*.

Embodiment 11

The method of embodiment 5, wherein the microbe is *Acinetobacter baumannii*.

Embodiment 12

The method of embodiment 5, wherein the microbe is *Escherichia coli*.

Embodiment 13

The method of any one of embodiments 1-12, wherein the biological structure is an efflux pump.

Embodiment 14

The method of any one of embodiments 1-13, wherein the compound lessens an activity of a drug resistance mechanism in the microbe.

Embodiment 15

The method of any one of embodiments 1-14, wherein the method further comprises administering to the subject a therapeutically-effective amount of a second compound.

Embodiment 16

The method of embodiment 15, wherein the compound increases an activity of the second compound.

Embodiment 17

The method of any one of embodiments 15-16, wherein the second compound is an antibiotic.

Embodiment 18

The method of embodiment 17, wherein the antibiotic is polymyxin B or a pharmaceutically-acceptable salt thereof.

Embodiment 19

The method of any one of embodiments 15-18, wherein the compound and the second compound are administered in a common unit dosage form.

Embodiment 20

The method of any one of embodiments 1-19, wherein the administration is oral.

Embodiment 21

The method of any one of embodiments 1-19, wherein the administration is intravenous.

Embodiment 22

The method of any one of embodiments 1-19, wherein the administration is subcutaneous.

Embodiment 23

The method of any one of embodiments 1-19, wherein the administration is topical.

Embodiment 24

The method of any one of embodiments 1-23, wherein the administration occurs via an oily carrier.

Embodiment 25

The method of any one of embodiments 1-24, wherein the therapeutically-effective amount is from about 5 mg/kg to about 50 mg/kg.

Embodiment 26

The method of any one of embodiments 1-25, wherein the compound is a compound of formula:

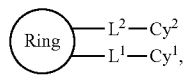

wherein:
RING is a ring system;
$Cy^1$ is a cyclic group;
$Cy^2$ is a cyclic group;
$L^1$ is a linking group; and
$L^2$ is independently a linking group, or a pharmaceutically-acceptable salt thereof.

Embodiment 27

The method of any one of embodiments 1-26, wherein the compound is a compound of formula:

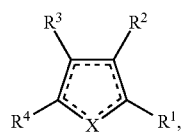

wherein:
X is N, NH, S, or O;
each ===== is independently a single bond or a double bond;
$R^1$ is H or -$L^1$-$Cy^1$;
$R^2$ is H or -$L^2$-$Cy^2$;
$R^3$ is H or -$L^3$-$Cy^3$ and $R^4$ is H or -$L^4$-$Cy^4$, or $R^3$ and $R^4$ together with the atoms to which $R^3$ and $R^4$ are bound form a ring;
each of $L^1$, $L^2$, $L^3$, and $L^4$ is independently a linking group; and
each of $Cy^1$, $Cy^2$, $Cy^3$, and $Cy^4$ is independently a cyclic group, or a pharmaceutically-acceptable salt thereof.

Embodiment 28

The method of embodiment 27, wherein the compound is a compound of formula:

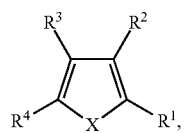

Embodiment 29

The method of any one of embodiments 1-28, wherein the compound is a compound of formula:

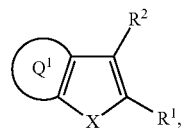

wherein:
X is NH, S, or O;
$Q^1$ is a ring system;
$R^1$ is H or -$L^1$-$Cy^1$;
$R^2$ is H or -$L^2$-$Cy^2$;
each of $L^1$ and $L^2$ is independently a linking group; and
each of $Cy^1$ and $Cy^2$ is independently a cyclic group, or a pharmaceutically-acceptable salt thereof.

Embodiment 30

The method of any one of embodiments 1-29, wherein the compound is a compound of formula:

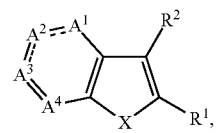

wherein:
X is NH, S, or O;
each ===== is independently a single bond or a double bond;
$R^1$ is H or -$L^1$-$Cy^1$;
$R^2$ is H or -$L^2$-$Cy^2$;
$A^1$ is $C(R^{1a})$, $C(R^{1a})(R^{1b})$, N, or $N(R^{1a})$;
$A^2$ is $C(R^{2a})$, $C(R^{2a})(R^{2b})$, N, or $N(R^{2a})$;
$A^3$ is $C(R^{3a})$, $C(R^{3a})(R^{3b})$, N, or $N(R^{3a})$;
$A^4$ is $C(R^{4a})$, $C(R^{4a})(R^{4b})$, N, or $N(R^{4a})$;
each $R^{1a}$, $R^{1b}$, $R^{2a}$, $R^{2b}$, $R^{3a}$, $R^{3b}$, $R^{4a}$, and $R^{4b}$ is independently: halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted, or H, or $R^{1a}$ and $R^{1b}$ together form a carbonyl, a thiocarbonyl, an imine, or an olefin, or $R^{2a}$ and $R^{2b}$ together form a carbonyl, a thiocarbonyl, an imine, or an olefin, or $R^{3a}$ and $R^{3b}$ together form a carbonyl, a thiocarbonyl, an imine, or an olefin, or $R^{4a}$ and $R^{4b}$ together form a carbonyl, a thiocarbonyl, an imine, or an olefin;
each of $L^1$ and $L^2$ is independently a linking group; and
each of $Cy^1$ and $Cy^2$ is independently a cyclic group, or a pharmaceutically-acceptable salt thereof.

Embodiment 31

The method of embodiment 30, wherein the compound is a compound of formula:

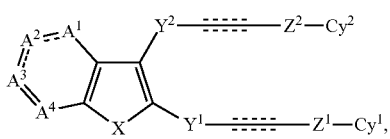

wherein:
    each ≡≡≡ is independently a single, double, or triple bond; and
    each $Y^1$, $Y^2$, $Z^1$, and $Z^2$ is independently: a bond, an alkylene group, an alkenylene group, an alkynylene group, an amino linkage, and ether linkage, a thioether linkage, an ester linkage, a thioester linkage, an amide linkage, a carbamate linkage, a carbonate linkage, a ureido linkage, a sulfoxide linkage, a sulfone linkage, a sulfonamide linkage, or an imine linkage.

Embodiment 32

The method of embodiment 31, wherein the compound is a compound of formula:

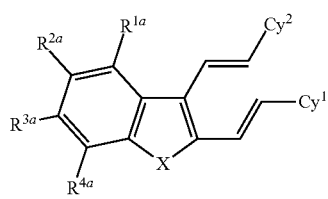

wherein: each $R^{1a}$, $R^{1b}$, $R^{2a}$, $R^{2b}$, $R^{3a}$, $R^{3b}$, $R^{4a}$, and $R^{4b}$ is independently: halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted, or H.

Embodiment 33

The method of embodiment 32, wherein: X is NH, $Cy^1$ is aryl that is unsubstituted or substituted, and $Cy^2$ is aryl that is unsubstituted or substituted.

Embodiment 34

The method of embodiment 32, wherein: X is NH, $Cy^1$ is phenyl that is unsubstituted or substituted, and $Cy^2$ is phenyl that is unsubstituted or substituted.

Embodiment 35

The method of embodiment 32, wherein each $R^{1a}$, $R^{2a}$, $R^{3a}$, and $R^{4a}$ is independently: F, Cl, Br, I, hydroxyl, sulfhydryl, nitro, nitroso, an acyl group, an acyloxy group, alkyl, alkenyl, alkynyl, an alkoxy group, an ether group, a carboxylic acid group, an ester group, an amine group, an amide group, a carbonate group, or a carbamate group, any of which is substituted or unsubstituted, or H.

Embodiment 36

The method of embodiment 32, wherein each $R^{1a}$, $R^{2a}$, $R^{3a}$, and $R^{4a}$ is H.

Embodiment 37

The method of any one of embodiments 1-36, wherein the compound is:

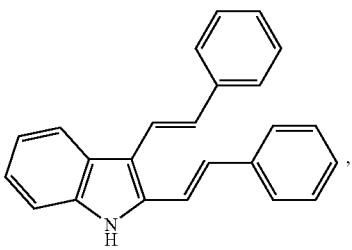 [SMILES: C(=C\c1[nH]c2ccccc2c1/C=C/c1ccccc1)/c1ccccc1]

or a pharmaceutically-acceptable salt thereof.

Embodiment 38

The method of any one of embodiments 1-36, wherein the compound is:

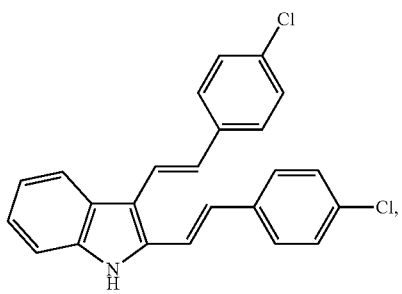

or a pharmaceutically-acceptable salt thereof.

Embodiment 39

The method of any one of embodiments 1-36, wherein the compound is:

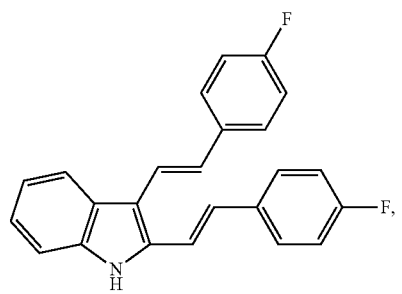 [SMILES: Fc1ccc(/C=C/c2[nH]c3ccccc3c2/C=C/c2ccc(F)cc2)cc1]

or a pharmaceutically-acceptable salt thereof.

Embodiment 40

The method of any one of embodiments 1-36, wherein the compound is:

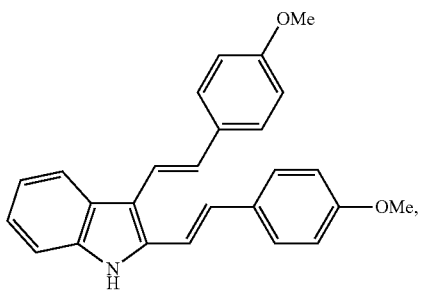 [SMILES: COc1ccc(/C=C/c2[nH]c3ccccc3c2/C=C/c2ccc(OC)cc2)cc1]

or a pharmaceutically-acceptable salt thereof.

Embodiment 41

A pharmaceutical composition comprising, in a unit dosage form:
a) a therapeutically-effective amount of a compound of formula:

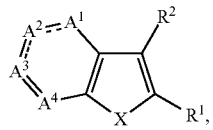

wherein:
X is NH, S, or O;
each ==== is independently a single bond or a double bond;
$R^1$ is -$L^1$-$Cy^1$;
$R^2$ is -$L^2$-$Cy^2$;
$A^1$ is $C(R^{1a})$, $C(R^{1a})(R^{1b})$, N, or $N(R^{1a})$;
$A^2$ is $C(R^{2a})$, $C(R^{2a})(R^{2b})$, N, or $N(R^{2a})$;
$A^3$ is $C(R^{3a})$, $C(R^{3a})(R^{3b})$, N, or $N(R^{3a})$;
$A^4$ is $C(R^{4a})$, $C(R^{4a})(R^{4b})$, N, or $N(R^{4a})$;
each $R^{1a}$, $R^{1b}$, $R^{2a}$, $R^{2b}$, $R^{3a}$, $R^{3b}$, $R^{4a}$, and $R^{4b}$ is independently: halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted, or H, or $R^{1a}$ and $R^{1b}$ together form a carbonyl, a thiocarbonyl, an imine, or an olefin, or $R^{2a}$ and $R^{2b}$ together form a carbonyl, a thiocarbonyl, an imine, or an olefin, or $R^{3a}$ and $R^{3b}$ together form a carbonyl, a thiocarbonyl, an imine, or an olefin, or $R^{4a}$ and $R^{4b}$ together form a carbonyl, a thiocarbonyl, an imine, or an olefin;
each of $L^1$ and $L^2$ is independently a linking group; and
each of $Cy^1$ and $Cy^2$ is independently a cyclic group, or a pharmaceutically-acceptable salt thereof; and
b) a pharmaceutically-acceptable excipient.

Embodiment 42

The pharmaceutical composition of embodiment 41, wherein the compound is a compound of formula:

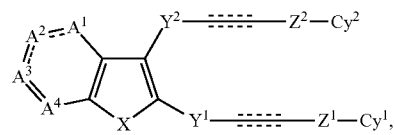

wherein:
each ==== is independently a single, double, or triple bond; and
each $Y^1$, $Y^2$, $Z^1$, and $Z^2$ is independently: a bond, an alkylene group, an alkenylene group, an alkynylene group, an amino linkage, and ether linkage, a thioether linkage, an ester linkage, a thioester linkage, an amide linkage, a carbamate linkage, a carbonate linkage, a ureido linkage, a sulfoxide linkage, a sulfone linkage, a sulfonamide linkage, or an imine linkage.

Embodiment 43

The pharmaceutical composition of any one of embodiments 41-42, wherein the compound is a compound of formula:

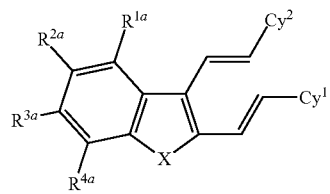

wherein: each $R^{1a}$, $R^{1b}$, $R^{2a}$, $R^{2b}$, $R^{3a}$, $R^{3b}$, $R^{4a}$, and $R^{4b}$ is independently: halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted, or H.

Embodiment 44

The pharmaceutical composition of embodiment 43, wherein: X is NH, $Cy^1$ is aryl that is unsubstituted or substituted, and $Cy^2$ is aryl that is unsubstituted or substituted.

Embodiment 45

The pharmaceutical composition of embodiment 43, wherein: X is NH, $Cy^1$ is phenyl that is unsubstituted or substituted, and $Cy^2$ is phenyl that is unsubstituted or substituted.

Embodiment 46

The pharmaceutical composition of embodiment 43, wherein each $R^{1a}$, $R^{2a}$, $R^{3a}$, and $R^{4a}$ is independently: F, Cl, Br, I, hydroxyl, sulfhydryl, nitro, nitroso, an acyl group, an acyloxy group, alkyl, alkenyl, alkynyl, an alkoxy group, an ether group, a carboxylic acid group, an ester group, an amine group, an amide group, a carbonate group, or a carbamate group, any of which is substituted or unsubstituted, or H.

Embodiment 47

The pharmaceutical composition of embodiment 43, wherein each $R^{1a}$, $R^{2a}$, $R^{3a}$, and $R^{4a}$ is H.

Embodiment 48

The pharmaceutical composition of any one of embodiments 41-47, wherein the compound is:

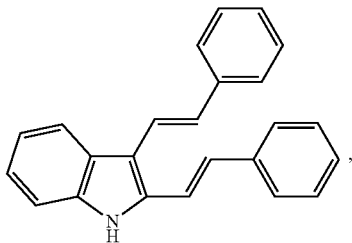 [SMILES: C(=C\c1[nH]c2ccccc2c1/C=C/c1ccccc1)/c1ccccc1]

or a pharmaceutically-acceptable salt thereof.

Embodiment 49

The pharmaceutical composition of any one of embodiments 41-47, wherein the compound is:

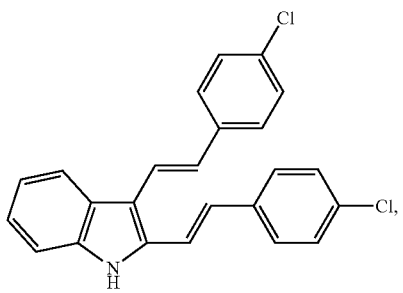

or a pharmaceutically-acceptable salt thereof.

Embodiment 50

The pharmaceutical composition of any one of embodiments 41-47, wherein the compound is:

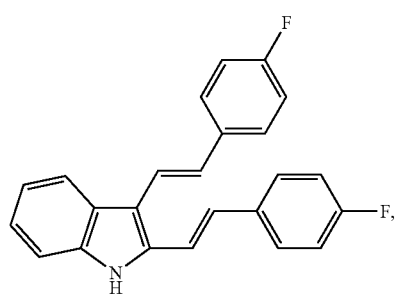 [SMILES: Fc1ccc(/C=C/c2[nH]c3ccccc3c2/C=C/c2ccc(F)cc2)cc1]

or a pharmaceutically-acceptable salt thereof.

Embodiment 51

The pharmaceutical composition of any one of embodiments 41-47, wherein the compound is:

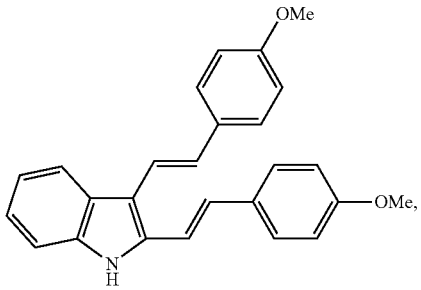 [SMILES: COc1ccc(/C=C/c2[nH]c3ccccc3c2/C=C/c2ccc(OC)cc2)cc1]

or a pharmaceutically-acceptable salt thereof.

Embodiment 52

The pharmaceutical composition of any one of embodiments 41-51, further comprising an antibiotic.

Embodiment 53

The pharmaceutical composition of embodiment 52, wherein the antibiotic is polymyxin B or a pharmaceutically-acceptable salt thereof.

Embodiment 54

The pharmaceutical composition of any one of embodiments 41-53, wherein the therapeutically-effective amount is from about 5 mg/kg to about 50 mg/kg.

Embodiment 55

The pharmaceutical composition of any one of embodiments 41-54, wherein the pharmaceutically-acceptable excipient is an oily carrier.

Embodiment 56

A method of treating a condition, the method comprising administering to a subject in need thereof a therapeutically-effective amount of a compound of formula:

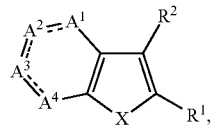

wherein:
X is NH, S, or O;
each ===== is independently a single bond or a double bond;
$R^1$ is -$L^1$-$Cy^1$;
$R^2$ is -$L^2$-$Cy^2$;
$A^1$ is $C(R^{1a})$, $C(R^{1a})(R^{1b})$, N, or $N(R^{1a})$;
$A^2$ is $C(R^{2a})$, $C(R^{2a})(R^{2b})$, N, or $N(R^{2a})$;
$A^3$ is $C(R^{3a})$, $C(R^{3a})(R^{3b})$, N, or $N(R^{3a})$;
$A^4$ is $C(R^{4a})$, $C(R^{4a})(R^{4b})$, N, or $N(R^{4a})$;
each $R^{1a}$, $R^{1b}$, $R^{2a}$, $R^{2b}$, $R^{3a}$, $R^{3b}$, $R^{4a}$, and $R^{4b}$ is independently: halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted, or H, or $R^{1a}$ and $R^{1b}$ together form a carbonyl, a thiocarbonyl, an imine, or an olefin, or $R^{2a}$ and $R^{2b}$ together form a carbonyl, a thiocarbonyl, an imine, or an olefin, or $R^{3a}$ and $R^{3b}$ together form a carbonyl, a thiocarbonyl, an imine, or an olefin, or $R^{4a}$ and $R^{4b}$ together form a carbonyl, a thiocarbonyl, an imine, or an olefin;

each of $L^1$ and $L^2$ is independently a linking group; and
each of $Cy^1$ and $Cy^2$ is independently a cyclic group, or a pharmaceutically-acceptable salt thereof.

Embodiment 57

The method of embodiment 56, wherein the compound is a compound of formula:

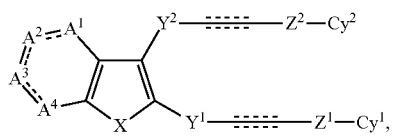

wherein:
each ≡≡≡ is independently a single, double, or triple bond; and
each $Y^1$, $Y^2$, $Z^1$, and $Z^2$ is independently: a bond, an alkylene group, an alkenylene group, an alkynylene group, an amino linkage, and ether linkage, a thioether linkage, an ester linkage, a thioester linkage, an amide linkage, a carbamate linkage, a carbonate linkage, a ureido linkage, a sulfoxide linkage, a sulfone linkage, a sulfonamide linkage, or an imine linkage.

Embodiment 58

The method of any one of embodiments 56-57, wherein the compound is a compound of formula:

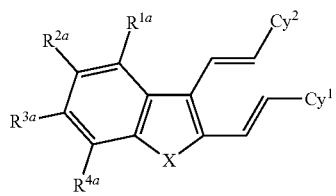

wherein: each $R^{1a}$, $R^{1b}$, $R^{2a}$, $R^{2b}$, $R^{3a}$, $R^{3b}$, $R^{4a}$, and $R^{4b}$ is independently: halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted, or H.

Embodiment 59

The method of embodiment 58, wherein: X is NH, $Cy^1$ is aryl that is unsubstituted or substituted, and $Cy^2$ is aryl that is unsubstituted or substituted.

Embodiment 60

The method of embodiment 58, wherein: X is NH, $Cy^1$ is phenyl that is unsubstituted or substituted, and $Cy^2$ is phenyl that is unsubstituted or substituted.

Embodiment 61

The method of embodiment 58, wherein each $R^{1a}$, $R^{2a}$, $R^{3a}$, and $R^{4a}$ is independently: F, Cl, Br, I, hydroxyl, sulfhydryl, nitro, nitroso, an acyl group, an acyloxy group, alkyl, alkenyl, alkynyl, an alkoxy group, an ether group, a carboxylic acid group, an ester group, an amine group, an amide group, a carbonate group, or a carbamate group, any of which is substituted or unsubstituted, or H.

Embodiment 62

The method of embodiment 58, wherein each $R^{1a}$, $R^{2a}$, $R^{3a}$, and $R^{4a}$ is H.

Embodiment 63

The method of any one of embodiments 56-62, wherein the compound is:

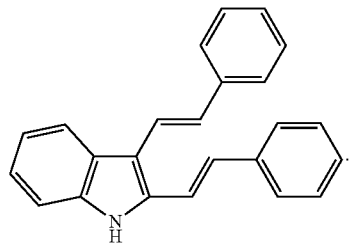 [SMILES: C(=C\c1[nH]c2ccccc2c1/C=C/c1ccccc1)/c1ccccc1]

Embodiment 64

The method of any one of embodiments 56-62 wherein the compound is:

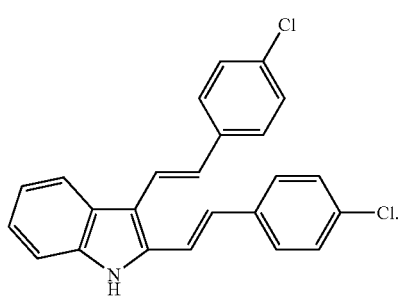 [SMILES: Clc1ccc(/C=C/c2[nH]c3ccccc3c2/C=C/c2ccc(Cl)cc2)cc1]

Embodiment 65

The method of any one of embodiments 56-62, wherein the compound is:

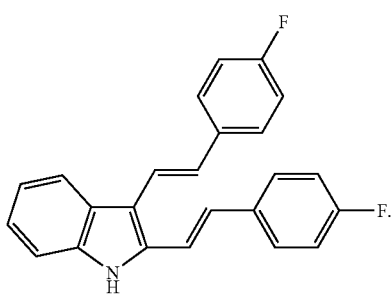 [SMILES: Fc1ccc(/C=C/c2[nH]c3ccccc3c2/C=C/c2ccc(F)cc2)cc1]

Embodiment 66

The method of any one of embodiments 56-62, wherein the compound is:

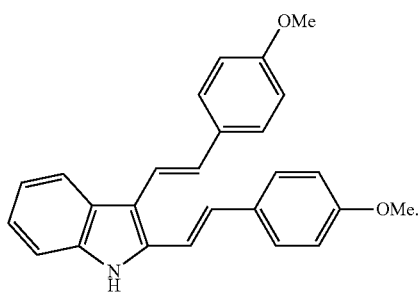 [SMILES: COc1ccc(/C=C/c2[nH]c3ccccc3c2/C=C/c2ccc(OC)cc2)cc1]

Embodiment 67

The method of any one of embodiments 56-66, wherein the therapeutically-effective amount is from about 5 mg/kg to about 50 mg/kg.

Embodiment 68

The method of any one of embodiments 56-67, wherein the subject is human.

Embodiment 69

The method of any one of embodiments 56-68, further comprising irradiating the compound after administration to the subject.

Embodiment 70

The method of embodiment 69, wherein the compound is irradiated with light having a wavelength of about 200 to about 800 nm.

Embodiment 71

The method of any one of embodiments 56-70, wherein the administration is oral.

Embodiment 72

The method of any one of embodiments 56-70, wherein the administration is intravenous.

Embodiment 73

The method of any one of embodiments 56-70, wherein the administration is subcutaneous.

Embodiment 74

The method of any one of embodiments 56-70, wherein the administration is topical.

Embodiment 75

The method of any one of embodiments 56-74, wherein the administration occurs via an oily carrier.

Embodiment 76

The method of any one of embodiments 56-75, wherein the condition is a cancer.

Embodiment 77

A method of reducing drug resistance in a cell, the method comprising contacting the cell with a therapeutically-effective amount of a compound that binds a biological structure that reduces a drug resistance mechanism in the cell, wherein the compound is more therapeutically-effective in the presence of light than in the dark.

Embodiment 78

A method of increasing the activity of a therapeutic first compound in a cell, the method comprising contacting the cell with a therapeutically-effective amount of the therapeutic first compound and a therapeutically-effective amount of a second compound, wherein the therapeutic first compound has a therapeutic effect that is greater than the therapeutic effect in absence of the second compound, wherein the second compound is more effective in the presence of light than in the dark.

Embodiment 80

A method of treating a condition, the method comprising administering to a subject in need thereof a therapeutically-effective amount of a compound that binds a biological structure, thereby decreasing drug resistance in a cell, and a therapeutically-effective amount of a second agent.

Embodiment 81

The method of embodiment 80, wherein the subject is human.

Embodiment 82

The method of any one of embodiments 80-81, wherein the compound that binds the biological structure is more effective in the presence of light than in the dark.

Embodiment 83

The method of embodiment 82, further comprising irradiating the compound with light having a wavelength of about 200 to about 800 nm.

Embodiment 84

The method of any one of embodiments 80-84, wherein the condition is caused by a microbe.

Embodiment 85

The method of embodiment 84, wherein the microbe is a bacterium.

Embodiment 86

The method of embodiment 84, wherein the microbe is Gram-positive bacterium.

Embodiment 87

The method of embodiment 84, wherein the microbe is Gram-negative bacterium.

Embodiment 88

The method of embodiment 84, wherein the microbe is drug-resistant bacterium.

Embodiment 89

The method of embodiment 84, wherein the microbe is methicillin-resistant *Staphylococcus aureus*.

Embodiment 90

The method of embodiment 84, wherein the microbe is *Acinetobacter baumannii*.

Embodiment 91

The method of embodiment 84, wherein the microbe is *Escherichia coli*.

Embodiment 92

The method of any one of embodiments 80-91, wherein the biological structure is an efflux pump.

Embodiment 93

The method of any one of embodiments 80-92, wherein the compound lessens an activity of a drug resistance mechanism in the microbe.

Embodiment 94

The method of any one of embodiments 80-93, wherein the second agent is an antibiotic.

Embodiment 95

The method of any one of embodiment 94, wherein the antibiotic is polymyxin B or a pharmaceutically-acceptable salt thereof.

Embodiment 96

The method of any one of embodiments 94-95, wherein the compound and the second agent are administered in a common unit dosage form.

Embodiment 97

The method of any one of embodiments 80-96, wherein the administration is oral.

Embodiment 98

The method of any one of embodiments 80-96, wherein the administration is intravenous.

Embodiment 99

The method of any one of embodiments 80-96, wherein the administration is subcutaneous.

Embodiment 100

The method of any one of embodiments 80-96, wherein the administration is topical.

Embodiment 101

The method of any one of embodiments 80-100, wherein the administration occurs via an oily carrier.

Embodiment 102

The method of any one of embodiments 80-101, wherein the therapeutically-effective amount of the compound is from about 5 mg/kg to about 50 mg/kg.

Embodiment 103

The method of any one of embodiments 80-95, wherein the method further comprises irradiating the compound that binds a biological structure and the antibiotic.

Embodiment 104

The method of any one of embodiment 80-95, wherein the compound is a compound of formula:

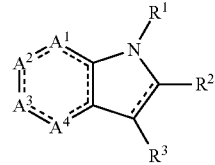

wherein:
$R^1$ is hydrogen or an ester group;
$R^2$ is hydrogen, halogen, or $L^1$-$Ar^1$;
$R^3$ is hydrogen, halogen, or $L^2$-$Ar^2$;
or $R^2$ and $R^3$ together with the atoms to which $R^2$ and $R^3$ are bound form a substituted or unsubstituted ring;
each $L^1$ and $L^2$ is independently a linking group or a bond;
$Ar^1$ is a substituted or unsubstituted aryl group;
$Ar^2$ is a substituted or unsubstituted aryl group wherein $Ar^2$ is not substituted with an amide, amine, nitro, imine, or ester group;
each $A^1$, $A^2$, $A^3$, and $A^4$ is independently $C(R^{1a})$, $C(R^{1a})(R^{1b})$, N, or $N(R^{1a})$;
each $R^{1a}$ and $R^{1b}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted; and each === is independently a single or double bond, or a pharmaceutically-acceptable salt thereof, wherein the compound is not:

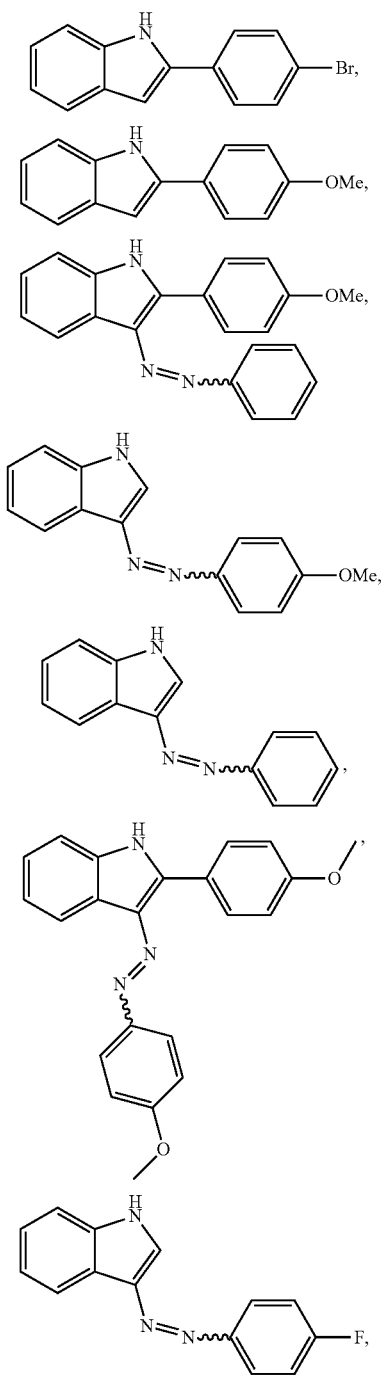

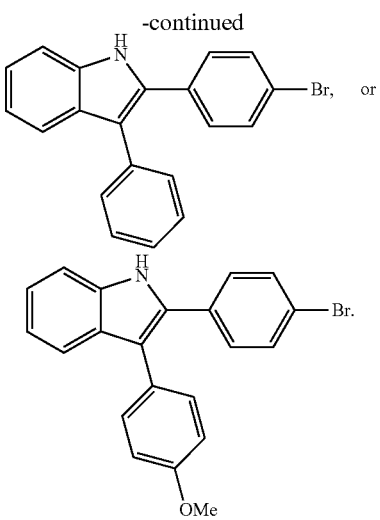

Embodiment 105

The method of embodiment 104, wherein when $Ar^1$ is phenyl brominated at one position, then $Ar^2$ is substituted on at least one position.

Embodiment 106

The method of embodiment 104, wherein when $Ar^1$ is phenyl substituted with one methoxy group, then $Ar^2$ is substituted on at least one position.

Embodiment 107

The method of embodiment 104, wherein $Ar^1$ is substituted, and $Ar^2$ is substituted.

Embodiment 108

The method of embodiment 104, wherein $Ar^1$ is unsubstituted, and $Ar^2$ is unsubstituted.

Embodiment 109

The method of embodiment 104, wherein both $L^1$ and $L^2$ are independently

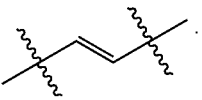 [SMILES: */C=C/*]

Embodiment 110

The method of embodiment 109, wherein both $Ar^1$ and $Ar^2$ are independently substituted with hydrogen, halogen, or alkyloxy.

Embodiment 111

The method of embodiment 104, wherein each linking group is independently alkylene, alkenylene, O, S, $SO_2$, CO, $N_2$, or a bond.

Embodiment 112

The method of embodiment 104, wherein each === is independently chosen to provide an aromatic system.

Embodiment 113

The method of any one of embodiments 80-112, wherein the compound is:

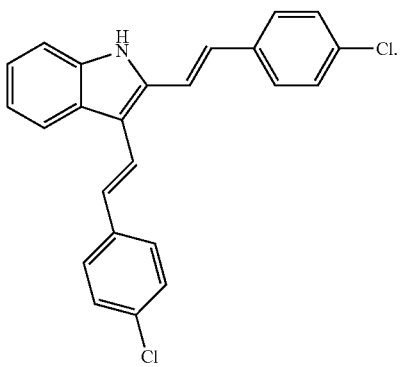 [SMILES: Clc1ccc(/C=C/c2[nH]c3ccccc3c2/C=C/c2ccc(Cl)cc2)cc1]

Embodiment 114

The method of any one of embodiments 80-112, wherein the compound is:

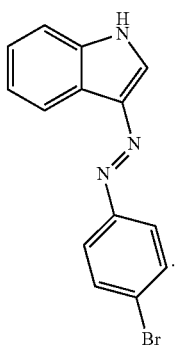 [SMILES: Brc1ccc(/N=N/c2c[nH]c3ccccc23)cc1]

Embodiment 115

The method of any one of embodiments 80-112, wherein the compound is:

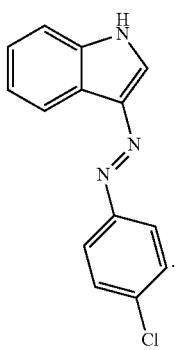 [SMILES: Clc1ccc(/N=N/c2c[nH]c3ccccc23)cc1]

Embodiment 116

The method of any one of embodiments 80-112, wherein the compound is:

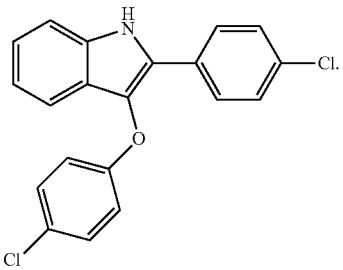 [SMILES: Clc1ccc(Oc2c(-c3ccc(Cl)cc3)[nH]c3ccccc23)cc1]

Embodiment 117

The method of any one of embodiments 80-112, wherein the compound is:

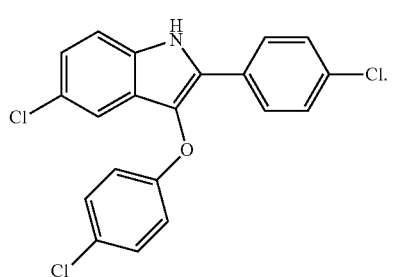 [SMILES: Clc1ccc(Oc2c(-c3ccc(Cl)cc3)[nH]c3ccc(Cl)cc23)cc1]

Embodiment 120

A compound of the formula:

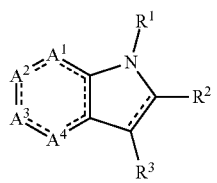

wherein:
$R^1$ is hydrogen or an ester group;
$R^2$ is hydrogen, halogen, or $L^1$-$Ar^1$;
$R^3$ is hydrogen, halogen, or $L^2$-$Ar^2$;
or $R^2$ and $R^3$ together with the atoms to which $R^2$ and $R^3$ are bound form a substituted or unsubstituted ring;
each $L^1$ and $L^2$ is independently a linking group or a bond;
$Ar^1$ is a substituted or unsubstituted aryl group;
$Ar^2$ is a substituted or unsubstituted aryl group wherein $Ar^2$ is not substituted with an amide, amine, nitro, imine, or ester group;
each $A^1$, $A^2$, $A^3$, and $A^4$ is independently $C(R^{1a})$, $C(R^{1a})(R^{1b})$, N, or $N(R^{1a})$;
each $R^{1a}$ and $R^{1b}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted; and each === is independently a single or double bond, or a pharmaceutically-acceptable salt thereof, wherein the compound is not:

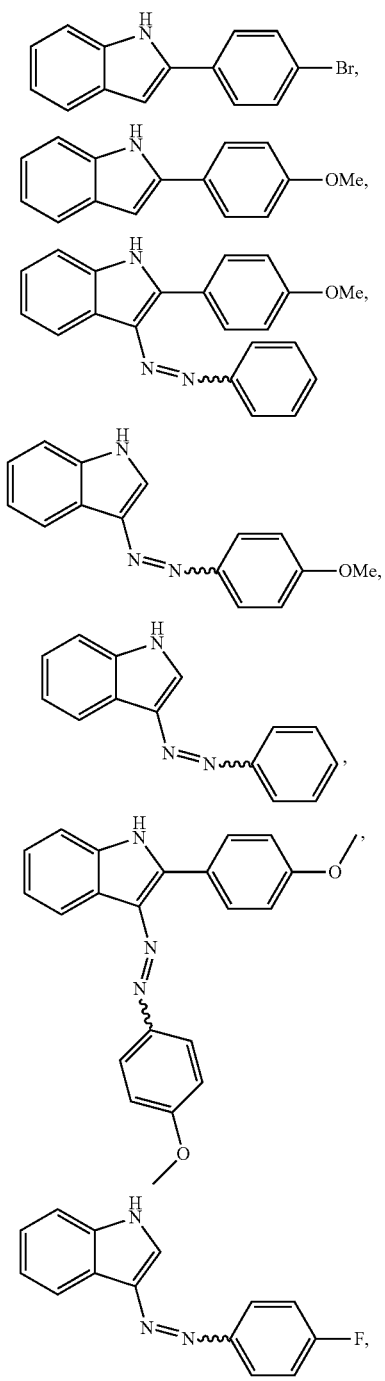

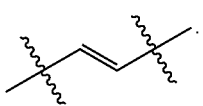 [SMILES: */C=C/*]

Embodiment 121

The compound of embodiment 120, wherein when $Ar^1$ is phenyl brominated at one position, then $Ar^2$ is substituted on at least one position.

Embodiment 122

The compound of embodiment 120, wherein when $Ar^1$ is phenyl substituted with one methoxy group, then $Ar^2$ is substituted on at least one position.

Embodiment 123

The compound of embodiment 120, wherein $Ar^1$ is substituted, and $Ar^2$ is substituted.

Embodiment 124

The compound of embodiment 120, wherein $Ar^1$ is unsubstituted, and $Ar^2$ is unsubstituted.

Embodiment 125

The compound of embodiment 120, wherein both $L^1$ and $L^2$ are independently

Embodiment 126

The compound of embodiment 125, wherein both $Ar^1$ and $Ar^2$ are independently substituted with hydrogen, halogen, or alkyloxy.

Embodiment 127

The compound of embodiment 120, wherein each linking group is independently alkylene, alkenylene, O, S, $SO_2$, CO, $N_2$, or a bond.

Embodiment 128

The compound of embodiment 120, wherein each ==== is independently chosen to provide an aromatic system.

Embodiment 129

The compound of embodiment 120-128, wherein the compound is:

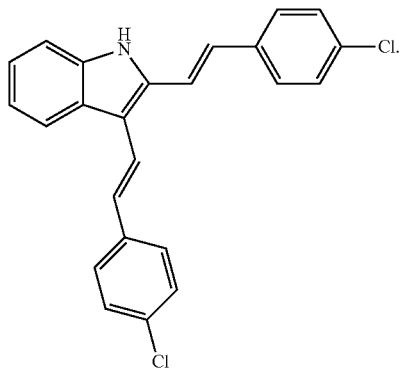 [SMILES: Clc1ccc(/C=C/c2[nH]c3ccccc3c2/C=C/c2ccc(Cl)cc2)cc1]

Embodiment 130

The compound of embodiment 120-128, wherein the compound is:

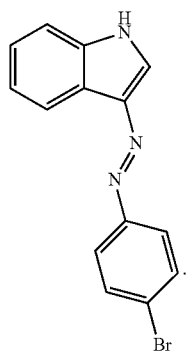 [SMILES: Brc1ccc(/N=N/c2c[nH]c3ccccc23)cc1]

Embodiment 131

The compound of embodiment 120-128, wherein the compound is:

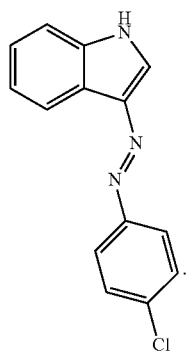

Embodiment 132

The compound of embodiment 120-128, wherein the compound is:

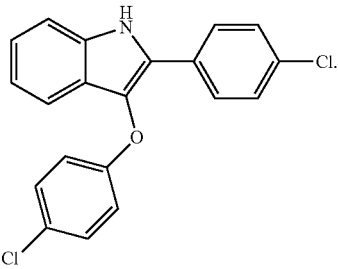 [SMILES: Clc1ccc(Oc2c(-c3ccc(Cl)cc3)[nH]c3ccccc23)cc1]

Embodiment 133

The compound of embodiment 120-128, wherein the compound is:

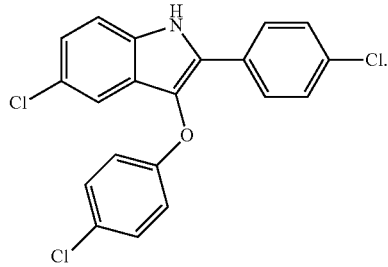 [SMILES: Clc1ccc(Oc2c(-c3ccc(Cl)cc3)[nH]c3ccc(Cl)cc23)cc1]

Embodiment 140

The method of any one of embodiments 1-25, wherein the compound is a compound of the formula:

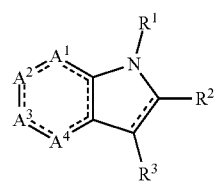

wherein:
  $R^1$ is hydrogen or an ester group;
  $R^2$ is hydrogen, halogen, or $L^1$-$Ar^1$;
  $R^3$ is hydrogen, halogen, or $L^2$-$Ar^2$;
  or $R^2$ and $R^3$ together with the atoms to which $R^2$ and $R^3$ are bound form a substituted or unsubstituted ring;
  each $L^1$ and $L^2$ is independently a linking group or a bond;
  each $Ar^1$ is independently a substituted or unsubstituted aryl group wherein $Ar^2$ is not substituted with an amide, amine, nitro, imine, or an ester group;
  each $Ar^2$ is independently a substituted or unsubstituted aryl group wherein $Ar^2$ is not substituted with an amide, amine, nitro, imine, or an ester group;
  each $A^1$, $A^2$, $A^3$, and $A^4$ is independently $C(R^{1a})$, $C(R^{1a})(R^{1b})$, N, or $N(R^{1a})$;
  each $R^{1a}$ and $R^{1b}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted; and each ═══ is independently a single or double bond, or a pharmaceutically-acceptable salt thereof, wherein the compound is not:

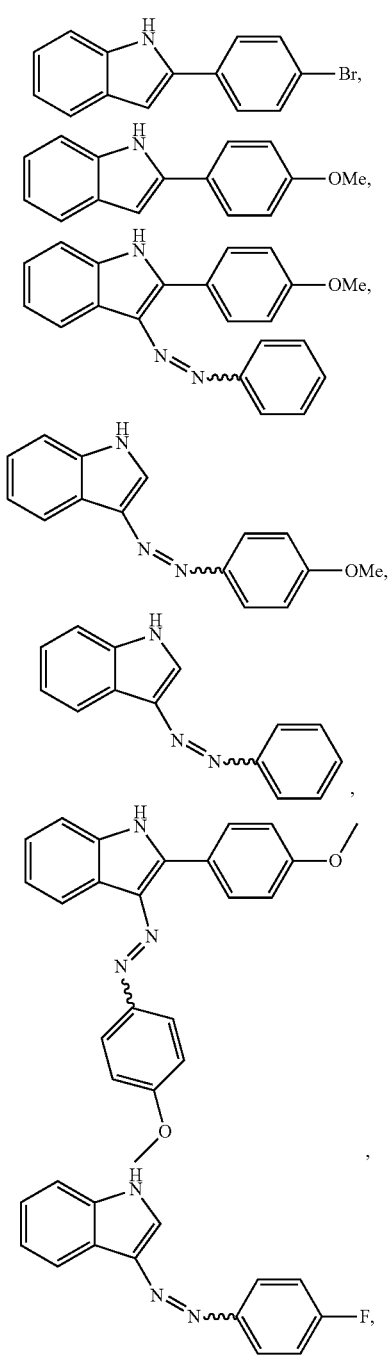

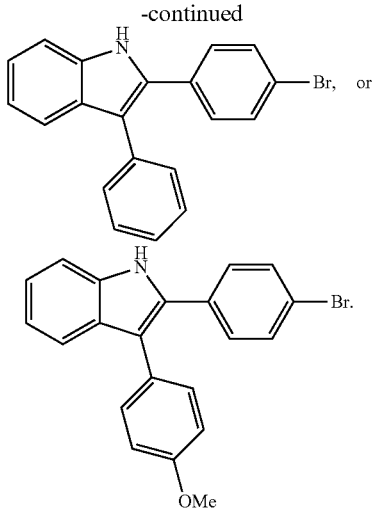

Embodiment 141

The compound of embodiment 140, wherein when $Ar^1$ is phenyl brominated at one position, then $Ar^2$ is substituted on at least one position.

Embodiment 142

The compound of embodiment 140, wherein when $Ar^1$ is phenyl substituted with one methoxy group, then $Ar^2$ is substituted on at least one position.

Embodiment 143

The compound of embodiment 140, wherein $Ar^1$ is substituted, and $Ar^2$ is substituted.

Embodiment 144

The compound of embodiment 140, wherein $Ar^1$ is unsubstituted, and $Ar^2$ is unsubstituted.

Embodiment 145

The compound of embodiment 134, wherein both $L^1$ and $L^2$ are independently

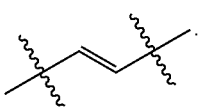 [SMILES: */C=C/*]

Embodiment 146

The compound of embodiment 139, wherein both $Ar^1$ and $Ar^2$ are independently substituted with hydrogen, halogen, or alkyloxy.

Embodiment 147

The compound of embodiment 134, wherein each linking group is independently alkylene, alkenylene, O, S, $SO_2$, CO, $N_2$, or a bond.

Embodiment 148

The compound of embodiment 134, wherein each ==== is independently chosen to provide an aromatic system.

Embodiment 149

The compound of any one of embodiments 140-149, wherein the compound is:

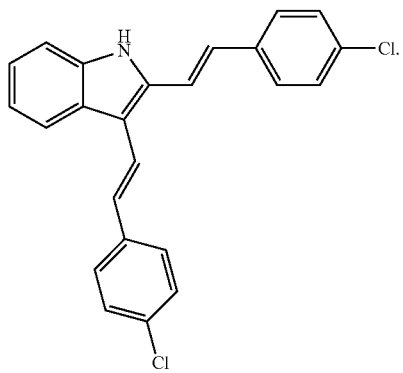 [SMILES: Clc1ccc(/C=C/c2[nH]c3ccccc3c2/C=C/c2ccc(Cl)cc2)cc1]

Embodiment 150

The compound of any one of embodiments 140-149, wherein the compound is:

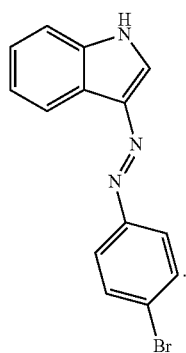 [SMILES: Brc1ccc(/N=N/c2c[nH]c3ccccc23)cc1]

Embodiment 151

The compound of any one of embodiments 140-149, wherein the compound is:

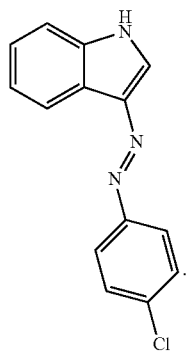

Embodiment 152

The compound of any one of embodiments 140-149, wherein the compound is:

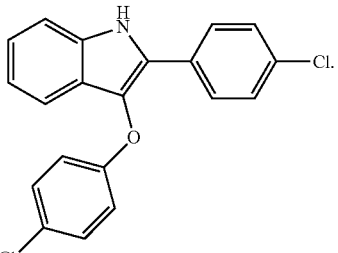

Embodiment 153

The compound of any one of embodiments 140-149, wherein the compound is:

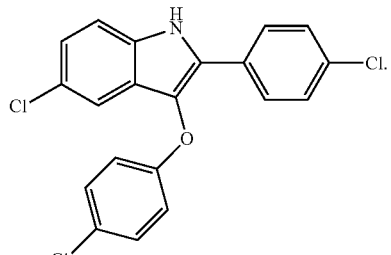

What is claimed is:

1. A method of treating an infection, the method comprising administering to a subject in need thereof a therapeutically-effective amount of a compound that binds a cellular target that is associated with a drug resistance mechanism, thereby decreasing drug resistance in a cell, and a therapeutically-effective amount of an antibiotic, wherein the antibiotic is polymyxin B, polymyxin E, norfloxacin, oxacillin, dicloxacillin, tetracycline, tobramycin, or vancomycin, or a pharmaceutically acceptable salt of any of the foregoing, wherein the compound is of the formula:

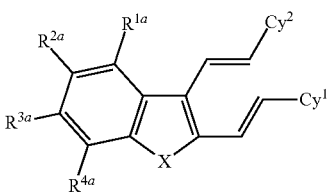

wherein:
X is NH;
each $Cy^1$ and $Cy^2$ is independently a substituted or unsubstituted phenyl group; and
each $R^{1a}$, $R^{2a}$, $R^{3a}$, and $R^{4a}$ is independently hydrogen.

2. The method of claim 1, wherein the subject is human.

3. The method of claim 1, wherein the compound that binds the cellular target is more effective in the presence of light than in the dark.

4. The method of claim 3, further comprising irradiating the compound with light having a wavelength of about 200 to about 800 nm.

5. The method of claim 1, wherein the infection is caused by a microbe.

6. The method of claim 5, wherein the microbe is a bacterium.

7. The method of claim 5, wherein the microbe is Gram-positive bacterium.

8. The method of claim 5, wherein the microbe is Gram-negative bacterium.

9. The method of claim 5, wherein the microbe is drug-resistant bacterium.

10. The method of claim 5, wherein the microbe is methicillin-resistant *Staphylococcus aureus*.

11. The method of claim 5, wherein the microbe is *Acinetobacter baumannii*.

12. The method of claim 5, wherein the microbe is *Escherichia coli*.

13. The method of claim 1, wherein the cellular target that is associated with a drug resistance mechanism is an efflux pump.

14. The method of claim 5, wherein the compound lessens an activity of a drug resistance mechanism in the microbe.

15. The method of claim 1, wherein the compound and the antibiotic are administered in a common unit dosage form.

16. The method of claim 1, wherein the administration of the compound is oral.

17. The method of claim 1, wherein the administration of the compound is intravenous.

18. The method of claim 1, wherein the administration of the compound is subcutaneous.

19. The method of claim 1, wherein the administration of the compound is topical.

20. The method of claim 1, wherein the administration of the compound occurs via an oily carrier.

21. The method of claim 1, wherein the therapeutically-effective amount of the compound is from about 5 mg/kg to about 50 mg/kg.

22. The method of claim 1, wherein the method further comprises irradiating the compound that binds the cellular target and the antibiotic.

23. The method of claim 1, wherein the compound is:

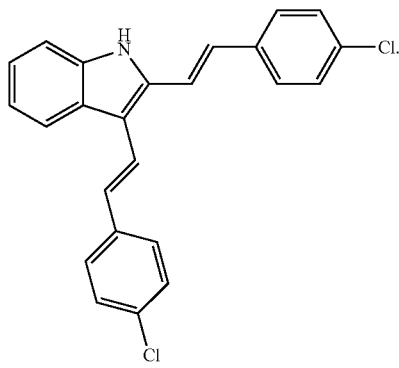 [SMILES: Clc1ccc(/C=C/c2[nH]c3ccccc3c2/C=C/c2ccc(Cl)cc2)cc1]

24. The method of claim 1, wherein each $Cy^1$ and $Cy^2$ is independently a substituted phenyl group.

25. The method of claim 24, wherein each substituted phenyl group is independently substituted with alkyl, alkoxy, or halogen.

26. The method of claim 24, wherein each substituted phenyl group is independently substituted with halogen.

27. The method of claim 24, wherein each substituted phenyl group is independently substituted with a chloro group.

28. The method of claim 24, wherein each substituted phenyl group is independently substituted with more than one chloro group.

29. The method of claim 24, wherein each substituted phenyl group is independently substituted with a fluoro group.

30. The method of claim 24, wherein each substituted phenyl group is independently substituted with a bromo group.

31. The method of claim 24, wherein each substituted phenyl group is independently substituted with an alkoxy group.

32. The method of claim 24, wherein each substituted phenyl group is independently substituted with a methoxy group.

33. The method of claim 1, wherein each $Cy^1$ and $Cy^2$ is independently an unsubstituted phenyl group.

34. The method of claim 1, wherein the antibiotic is polymyxin B or a pharmaceutically-acceptable salt thereof.

35. The method of claim 1, wherein the antibiotic is polymyxin E or a pharmaceutically-acceptable salt thereof.

36. The method of claim 1, wherein the antibiotic is norfloxacin or a pharmaceutically-acceptable salt thereof.

37. The method of claim 1, wherein the antibiotic is oxacillin or a pharmaceutically-acceptable salt thereof.

38. The method of claim 1, wherein the antibiotic is dicloxacillin or a pharmaceutically-acceptable salt thereof.

39. The method of claim 1, wherein the antibiotic is tetracycline or a pharmaceutically-acceptable salt thereof.

40. The method of claim 1, wherein the antibiotic is tobramycin or a pharmaceutically-acceptable salt thereof.

41. The method of claim 1, wherein the antibiotic is vancomycin or a pharmaceutically-acceptable salt thereof.

* * * * *